United States Patent
Kralj

(10) Patent No.: US 11,072,783 B2
(45) Date of Patent: Jul. 27, 2021

(54) COMPOSITIONS AND METHODS COMPRISING THE USE OF EXIGUOBACTERIUM ACETYLICUM AND BACILLUS COAGLUANS ALPHA-GLUCANOTRANSFERASE ENZYMES

(71) Applicant: DUPONT NUTRITION BIOSCIENCES APS, Copenhagen K (DK)

(72) Inventor: Slavko Kralj, Oegstgeest (NL)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 280 days.

(21) Appl. No.: 15/760,055

(22) PCT Filed: Oct. 6, 2016

(86) PCT No.: PCT/US2016/055849
§ 371 (c)(1),
(2) Date: Mar. 14, 2018

(87) PCT Pub. No.: WO2017/062687
PCT Pub. Date: Apr. 13, 2017

(65) Prior Publication Data
US 2018/0265852 A1    Sep. 20, 2018

Related U.S. Application Data

(60) Provisional application No. 62/238,054, filed on Oct. 6, 2015.

(51) Int. Cl.
*C12N 9/10* (2006.01)
*C12P 19/02* (2006.01)
*A23L 33/10* (2016.01)
*A23L 2/52* (2006.01)
*C12P 19/00* (2006.01)
*A61K 38/00* (2006.01)

(52) U.S. Cl.
CPC .............. *C12N 9/1051* (2013.01); *A23L 2/52* (2013.01); *A23L 33/10* (2016.08); *C12N 9/1074* (2013.01); *C12P 19/00* (2013.01); *C12Y 204/01025* (2013.01); *A23V 2002/00* (2013.01); *A61K 38/00* (2013.01)

(58) Field of Classification Search
CPC .................................................... C12N 9/1051
See application file for complete search history.

(56) References Cited

U.S. PATENT DOCUMENTS 6,617,143 B1 * 9/2003 Fukuyama ............... C11D 3/38
435/183

OTHER PUBLICATIONS

WP_029342707.1.2014.*
(Continued)

*Primary Examiner* — Yong D Pak

(57) ABSTRACT

An isolated and/or purified α-glucanotransferase from *Exiguobacterium Acetylicum*, recombinantly engineered variants thereof, active fragments thereof, synthetic nucleic acids encoding the α-glucanotransferase and variants thereof, host cells comprising the synthetic nucleic acids, and compositions comprising the α-glucanotransferase are provided. Methods of using the compositions include the manufacture of oligosaccharides.

12 Claims, 16 Drawing Sheets

Specification includes a Sequence Listing.

(56) References Cited

OTHER PUBLICATIONS

F7Z222_BACC6. 2011.*
AJH79253.1 2015.*
Studer. Residue mutations and their impact on protein structure and function: detecting beneficial and pathogenic changes. Biochem. J. (2013) 449, 581-594.*
Liebl. Purification and characterization of a novel thermostable 4-a-glucanotransferase of Thermotoga maritima cloned in *Escherichia coli*. Eur. J. Biochem. 207, 81-88 (1992).*
Takaha. The Functions of 4-α-glucanotransferases and their use for the Production of Cyclic Glucans. Bio/ec/lllology and Generic Engineering Rel•jews—vol. 16. Apr. 1999.*

* cited by examiner

| Bacterial Strain | Enzyme | Preferred Substrate | GH70 Sub Family | Main α-linkages introduced in glucan | | 1 | 2 |
|---|---|---|---|---|---|---|---|
| Lb. reuteri 121 | GTFA | Sucrose | GH70_1 | 1→4 / 1→6 | 1503 | GLQVMADWPDQ | |
| Lb. reuteri ATCC 55730 | GTFO | Sucrose | GH70_1 | 1→4 | 1503 | GLQVMADWPDQ | |
| Lb. reuteri 180 | GTF180 | Sucrose | GH70_1 | 1→6 | 1498 | GLQATADWPDQ | |
| Lb. reuteri ML1 | GTFML1 | Sucrose | GH70_1 | 1→3 | 1498 | GIQAMADWPDQ | |
| L. citreum NRRL B-1299 | DSRE CD2 | Sucrose/dextran | GH70_2 | 1→2 | 2683 | NMQVMADVVDNQ | |
| L. citreum NRRL B-1299 | BRSA | Sucrose/dextran | GH70_2 | 1→2 | 1146 | GMQVMADVVANQ | |
| Lb. reuteri 121 | 4,6α-GTB | MOS | GH70_3 | 1→6 | 1473 | GLKVQEDIVMNQ | |
| Lb. reuteri ML1 | 4,6α-GTML4 | MOS | GH70_3 | 1→6 | 1474 | GLKVQEDIVMNQ | |
| Lb. reuteri DSM 20016A | 4,6α-GTW | MOS | GH70_3 | 1→6 | 1211 | GLKVQEDLVMNQ | |
| E. acetylicum DSM20416 | α-GT-E | MOS | GH70_4 | 1→6 | 133 | NIKVQMDLVPNQ | |
| B. coagluans 2-6 | α-GT-S | MOS | GH70_4 | ND | 135 | GLKVQEDLVPNQ | |
| B. coagluans 2022696 | α-GT-L | MOS | GH70_4 | ND | 104 | GLKVQEDLVPNQ | |

FIG. 3B

| | II | | III | | IV | |
|---|---|---|---|---|---|---|
| | 3 4 | | 5 | | 6 7 | |
| 1018 | FDSVRVDAPDNIDADLMNI | 1056 | HINILEDWNHADP | 1126 | YSFVRAHD---NNSQ |
| 1018 | FDSVRVDAPDNIDADLMNI | 1056 | HINILEDWNSSDP | 1126 | YSFIRAHD---NNSQ |
| 1019 | FDGIRVDAVDNVDDLLSI | 1058 | HINILEDWGWDDP | 1129 | YNFVRAHD---SNAQ |
| 1019 | FDSIRVDAVDNVDADLLDI | 1058 | HINILEDWGGQDP | 1125 | YSFIRAHD---NGSQ |
| 2204 | FDSIRIDAVDFIHNDTIQR | 2243 | HISLVEAGLDAGT | 2315 | YSIIHAHD---KGVQ |
| 666 | FDSIRIDAVDFVSNDLIQR | 705 | HISLVEAGLDAGT | 777 | YSIIHAHD---KDIQ |
| 1009 | FDGFRVDAADNIDADVLDQ | 1048 | HLSYNEGYHSGAA | 1118 | WSFVTNHDQRKNLIN |
| 1010 | FDGFRVDAADNIDADVLDQ | 1048 | HLSYNEGYHSGAA | 1118 | WSFVTNHDQRKNLIN |
| 746 | FDGFRVDAADNIDADVLDQ | 786 | HLVYNEGYHSGAA | 856 | WSFVTNHDQRKNVIN |
| 401 | FDGFRIDAASHYDTAILKA | 433 | YLSYIESYKTEQN | 501 | WSFVNNHDQEKNRVN |
| 404 | FDGFRIDAAGHYDKVLLD | 438 | HLSYIESYQSAGT | 507 | WSFVNNHDQEKNRVN |
| 394 | FDGFRIDAASHYDKQVLLD | 428 | HLSYIETYESAGT | 497 | WSFVNNHDQEKNRVN |

*FIG. 3B Continued*

COMPOSITIONS AND METHODS COMPRISING THE USE OF EXIGUOBACTERIUM ACETYLICUM AND BACILLUS COAGLUANS ALPHA-GLUCANOTRANSFERASE ENZYMES

CROSS-REFERENCE TO RELATED APPLICATIONS

This application claims priority under 35 USC § 371 as a national phase of International Patent Application No. PCT/US2016/055849 (filed Oct. 6, 2016; and published on Apr. 13, 2017 as Publication No. WO2017062687A1), which claims priority to and the benefit of U.S. Provisional Application Ser. No. 62/238,054 (filed Oct. 6, 2015), titled 'COMPOSITIONS AND METHODS COMPRISING THE USE OF *EXIGUOBACTERIUM ACETYLICUM* AND *BACILLUS COAGLUANS* α-GLUCANOTRANSFERASE ENZYMES', which is hereby incorporated by reference in its entirety.

FIELD

An isolated and/or purified α-glucanotransferase from *Exiguobacterium Acetylicum*, recombinantly engineered variants thereof, active fragments thereof, synthetic nucleic acids encoding the α-glucanotransferase and variants thereof, host cells comprising the synthetic nucleic acids, and compositions comprising the α-glucanotransferase are provided. Methods of using the compositions include the manufacture of oligosaccharides.

SEQUENCE LISTING

A Sequence Listing, comprising SEQ ID NOs: 1-13, is attached and incorporated herein by reference in its entirety.

BACKGROUND (Glucooligosaccharides (GOS) of the isomaltooligosaccharide type (IMO), are gaining increased attention due to their beneficial health effects [VitaFiber™-IMO] (1) IMO are glucooligosaccharides composed of glucose units with α-(1→6) glycosidic linkages but depending on the way of IMO manufacturing they may contain in addition to the α-1,6 linked glucose units also additional glycosidic linkages such as α-1,3 and α-1,4. Isomaltooligosaccharides can be generated enzymatically by different enzymes. Commercial IMO are predominantly obtained from fungal glycosyltransferases using maltodextrins, derived from starch hydrolysis, as feedstock (2). Another approach to obtain IMO is hydrolysis of dextran by dextranase (3).

Glucansucrases (GTFs) are extracellular enzymes that historically are known for their ability to synthesize a variety of α-glucan polysaccharides such as dextran, mutan, alternan and reuteran from sucrose (4)(5) and in the presence of appropriate acceptors various oligosaccharides can be synthesized such as the panose oligosaccharide series and isomaltooligosaccharide series (6)(7)(8).

Together with amylases of GH13 the glucansucrase of GH70 belong to clan GH-H, containing a $(\beta/\alpha)_8$ barrel structure. However, GH70 enzymes have a $(\beta/\alpha)_8$ catalytic domain which is circularly permuted (9). Also, the four conserved regions (regions I to IV) identified in members of the α-amylase family GH13 are present in GH70 enzymes, but as consequence of this circular permutation, region I occurs C-terminally to regions II to IV in GH70 enzymes.

GH70 members can be divided in three distinct subfamilies as has been done for the large GH13 family (10), of which all three subfamilies are found in lactic acid bacteria only (FIG. 1A):
1) The common GH70 GTFs using sucrose as substrate, synthesizing α-glucan polymers, (4)(5)
2) Branching GH70 GTFs using sucrose as donor and dextran as acceptor introducing α-1,2 and α-1,3 branches in the dextran backbone (CBM11 pers. comm. M. Remaud-Simeon), (11)(12)
3) 4,6-α-GTs using MOS and starch as substrate introducing α-(1→6) glycosidic bonds, (13)(14)(15)

GH70 subfamily 1, are the common GH70 enzymes using sucrose to synthesize various α-glucan polymers. Depending on the enzyme glucans with various linkage types, branching and molecular masses are synthesized (4)(5). GH70 subfamily 2 have the capability to modify dextran backbones by introducing α-1,2 and α-1,3 branches (11) (12). GH70 subfamily 3 (4,6-α-GT enzymes) synthesize from MOS, linear IMO-MALT which are composed of α-(1→6) linked glucose moiety coupled to an α-glycon of α-(1→4) linked glucose units (15) (16) (17) [See also PCT Publication No. WO 2010/128859 directed to poly- and oligosaccharides and their nutritional effects].

SUMMARY

*Exiguobacterium acetylicum* harbours an α-glucanotransferase (α-GT-α) that efficiently synthesizes a broad range of glucooligosaccharides containing α-1,4 and α-1,6 glucosidic linkages from MOS, maltodextrins and starch. The isolated and/or purified α-glucanotransferases, recombinantly engineered variants thereof, active fragments thereof, synthetic nucleic acids encoding the α-glucanotransferases, its variants, or its active fragments, host cells comprising the synthetic nucleic acids, and compositions comprising the α-glucanotransferases are provided. Methods of using the compositions include the manufacture of glucooligosaccharides.

| GLOSSARY: | |
|---|---|
| BLAST | Basic Local Alignment Search Tool |
| CAZy | carbohydrate active enzymes database |
| EDTA | ethylenediaminetetraacetic acid |
| MOS | malto-oligosaccharide(s) |
| IMO | Isomaltooligosaccharides |
| GH70 | family 70 of glycoside hyrolases |
| GPC | gel permeation chromatography |
| HOD signal | an NMR signal from water in which one proton is exchanged for a deuterium |
| HPAEC | high performance anion-exchange chromatography |
| HPLC | high performance liquid chromatography |
| HPSEC | high performance size exclusion chromatography |
| HSQC | heteronuclear single quantum coherence |
| α-GT-E | putative α-glucanotransferase from *Exigobacterium acetylicum* |
| MALLS | multi angle laser light scattering |
| NMR | nuclear magnetic resonance |
| RI | refractive index |
| SEC | size-exclusion chromatography |
| TLC | thin layer chromatography |
| universal buffer | mixture of acetic acid, boric acid and phosphoric acid |

BRIEF DESCRIPTION OF THE FIGURES

FIG. 3B. Amino acid sequence alignment of conserved regions (I, II, III, IV) in the catalytic domains of GH70 from subfamilies 1, 2, 3 and 4. GH70_1: glucansucrase enzymes (GTFA, GTFO, GTF180 and GTFML1), GH70_2: branching sucrases (DSRE CD2 and BRSA), GH70_3: 4,6-α-glucanotransferase (4,6-α-GT-B, 4,6-α-GT-W and 4,6-α-GT-ML4) and GH70_4: α-glucanotransferase enzymes (α-GT-E of *E. acetylicum* DSM20416, α-GT-S of *B. coagulans* 2-6 and α-GT-L of *B. coagulans* 2022696). The seven strictly conserved amino acid residues, with important contributions to the −1 and +1 subsites in the different GH70 subfamilies are shown in light grey. The three catalytic residues are shown in bold. ND: not determined. Sequence identification numbers corresponding to the amino acid sequences in the figure are shown as follows (respectively, strain, enzyme, conserved region I, II, III, IV): Lb. *reuteri* 121, GTFA, SEQ ID NO:14, SEQ ID NO:15, SEQ ID NO:16, SEQ ID NO:17; Lb. *reuteri* ATCC 55370, GTFO, SEQ ID NO:18, SEQ ID NO:19, SEQ ID NO:20, SEQ ID NO:21; Lb. *reuteri* 180, GTF180, SEQ ID NO:22, SEQ ID NO:23, SEQ ID NO:24, SEQ ID NO:25; Lb. *reuteri* ML1, GTFML1, SEQ ID NO:26, SEQ ID NO:27, SEQ ID NO:28, SEQ ID NO:29; *L. citreum* NRRL B-1299, DSRE CD2, SEQ ID NO:30, SEQ ID NO:31, SEQ ID NO:32, SEQ ID NO:33; *L. citreum* NRRL B-1299, BRSA, SEQ ID NO:34, SEQ ID NO:35, SEQ ID NO:36, SEQ ID NO:37; Lb. *reuteri* 121, 4,6α-GTB, SEQ ID NO:38, SEQ ID NO:39, SEQ ID NO:40, SEQ ID NO:41; Lb. *reuteri* ML1, 4,6α-GTML4, SEQ ID NO:42, SEQ ID NO:43, SEQ ID NO:44, SEQ ID NO:45; Lb. *reuteri* DSM 20016[4], 4,6α-GTW, SEQ ID NO:46, SEQ ID NO:47, SEQ ID NO:48, SEQ ID NO:49; *E. acetylicum* DSM20416, α-GT-E, SEQ ID NO:50, SEQ ID NO:51, SEQ ID NO:52, SEQ ID NO:53; *B. coagulans* 2-6, α-GT-S, SEQ ID NO:54, SEQ ID NO:55, SEQ ID NO:56, SEQ ID NO:57; *B. coagulans* 2022696, α-GT-L, SEQ ID NO:58, SEQ ID NO:59, SEQ ID NO:60, SEQ ID NO:61.

DETAILED DISCLOSURE

Figure 3A:
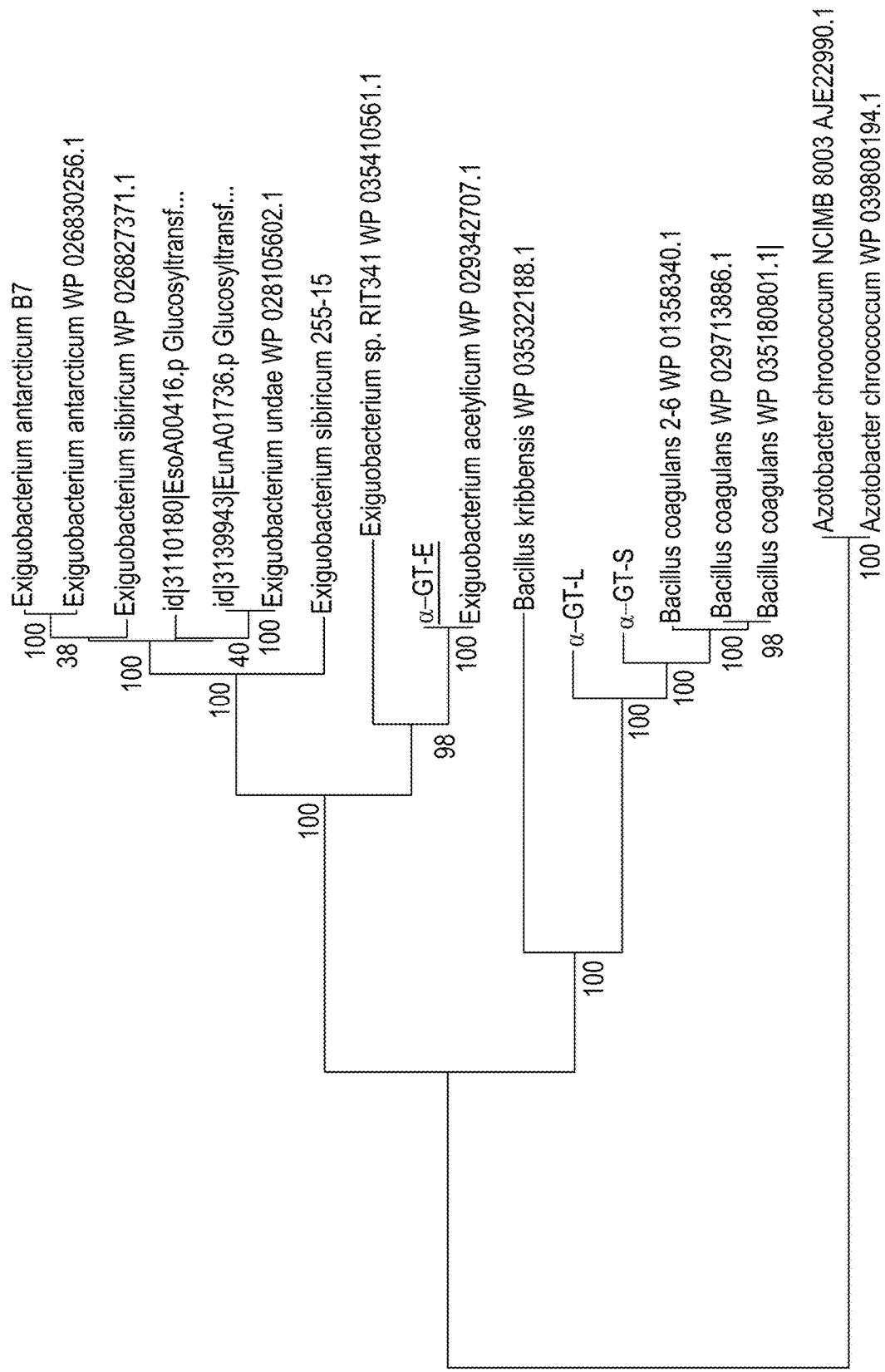
FIG. 3A. Unrooted phylogenetic tree of (putative) GH70 subfamily 4 α-GT proteins (without circularly permuted $(\beta/\alpha)_8$ barrel). Alignments and dendrogram construction were done with MEGA4 using the neighbor joining method. Bootstrap values (in percentage) are indicated at the branching points. The scale bar corresponds to a genetic distance of 0.1 substitution per position (10% amino acid sequence difference). Black: putative α-GTs from public database; grey: putative α-GTs from DuPont database.
Figure 4A:
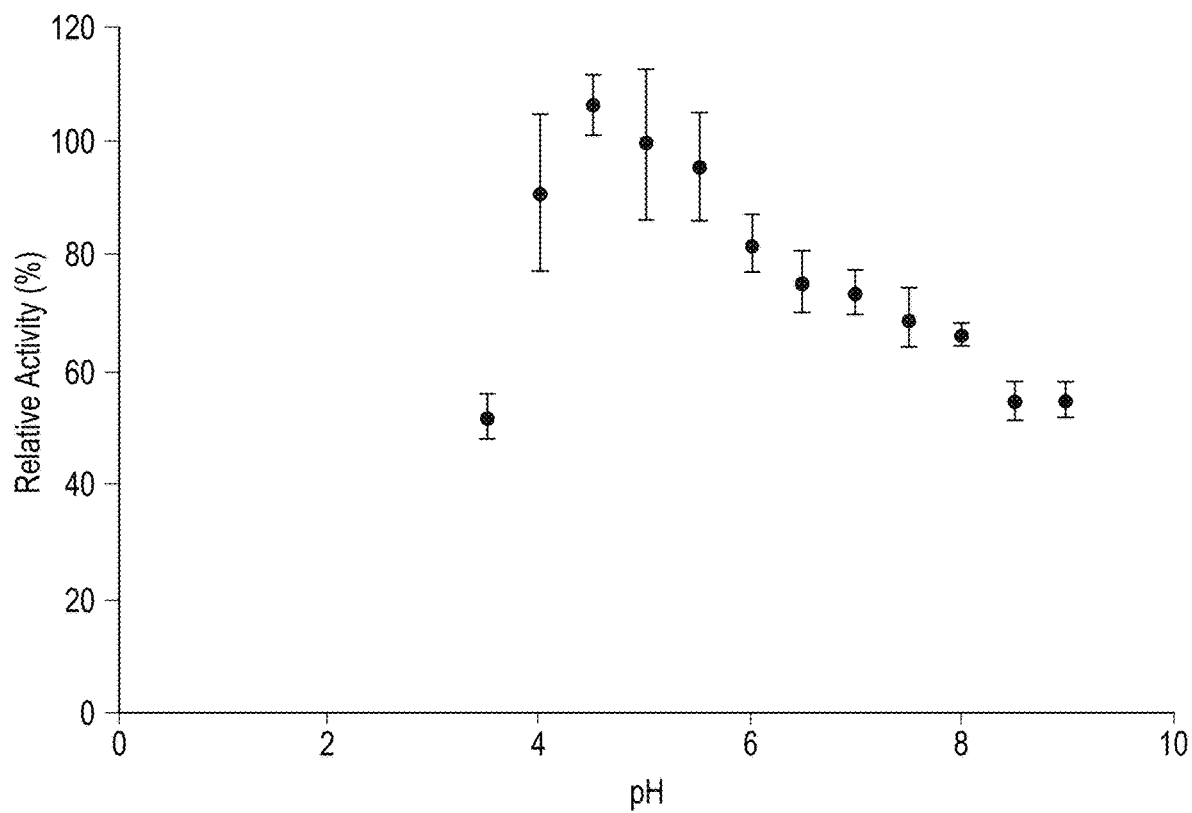
FIG. 4. The effect of pH on α-GT-E activity (A). Enzyme activity was determined at 37° C. in the presence of 1 mM $CaCl_2$ by measuring the amount of reducing sugars released by PABAH in 30 min from 1% zulkowsky starch by 0.0375 g/l α-GTE enzyme in 186 mM universal buffer containing 1 mM $CaCl_2$. The effect of temperature (B) was determined in 186 mM universal buffer pH 5.0 supplemented with 1 mM $CaCl_2$ (means±S.E.M.; n=3).
Figure 4B:
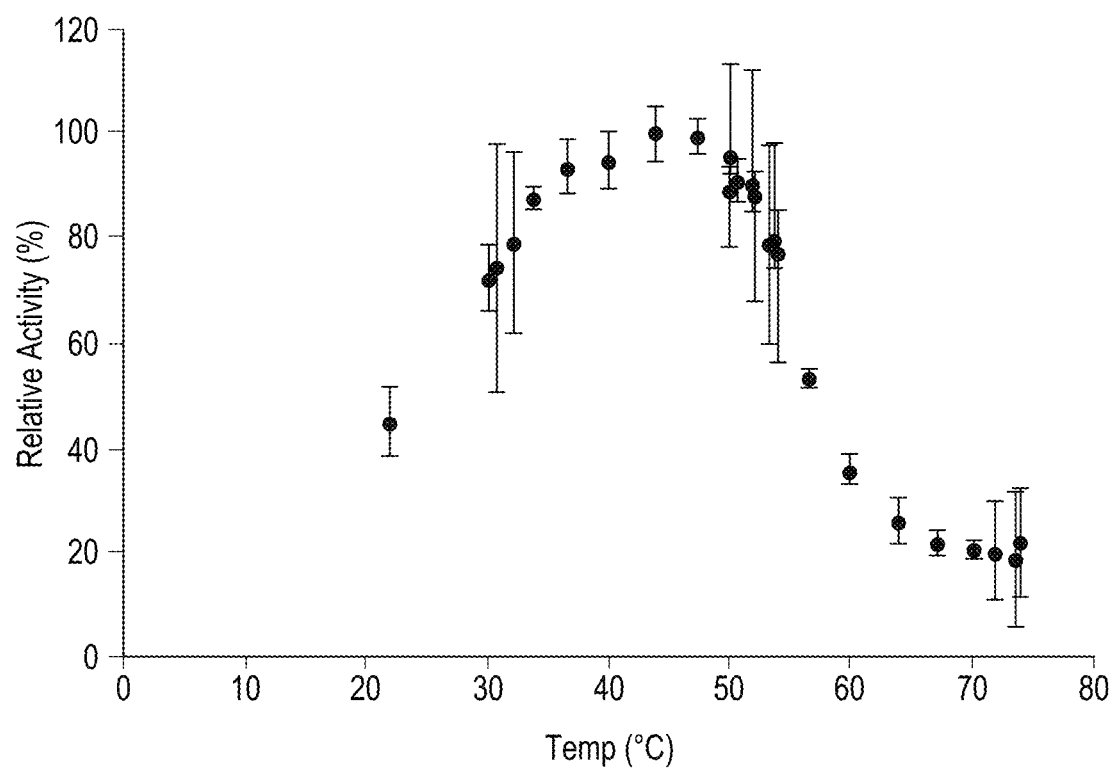
Figure 5:
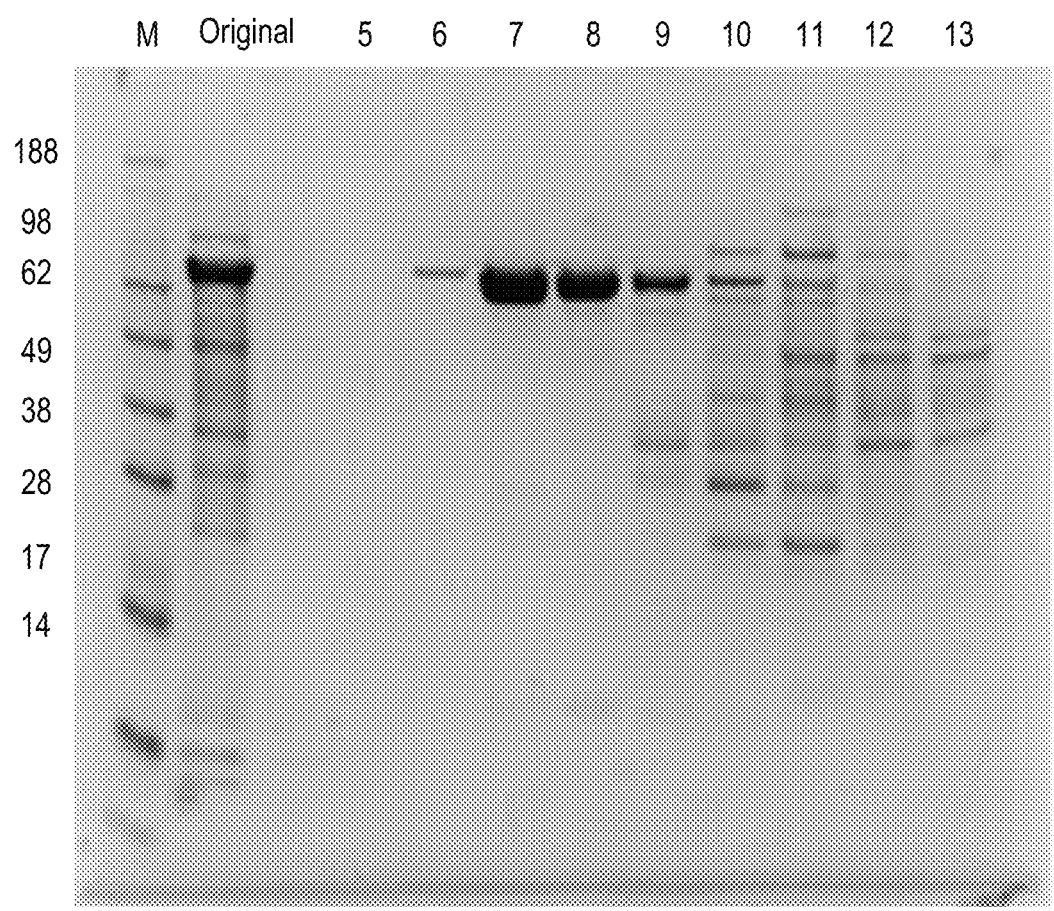
FIG. 5. SDS-PAGE of α-GT-E showing supernatant (original) and fractions (5-13) after anion purification.
Figure 6:
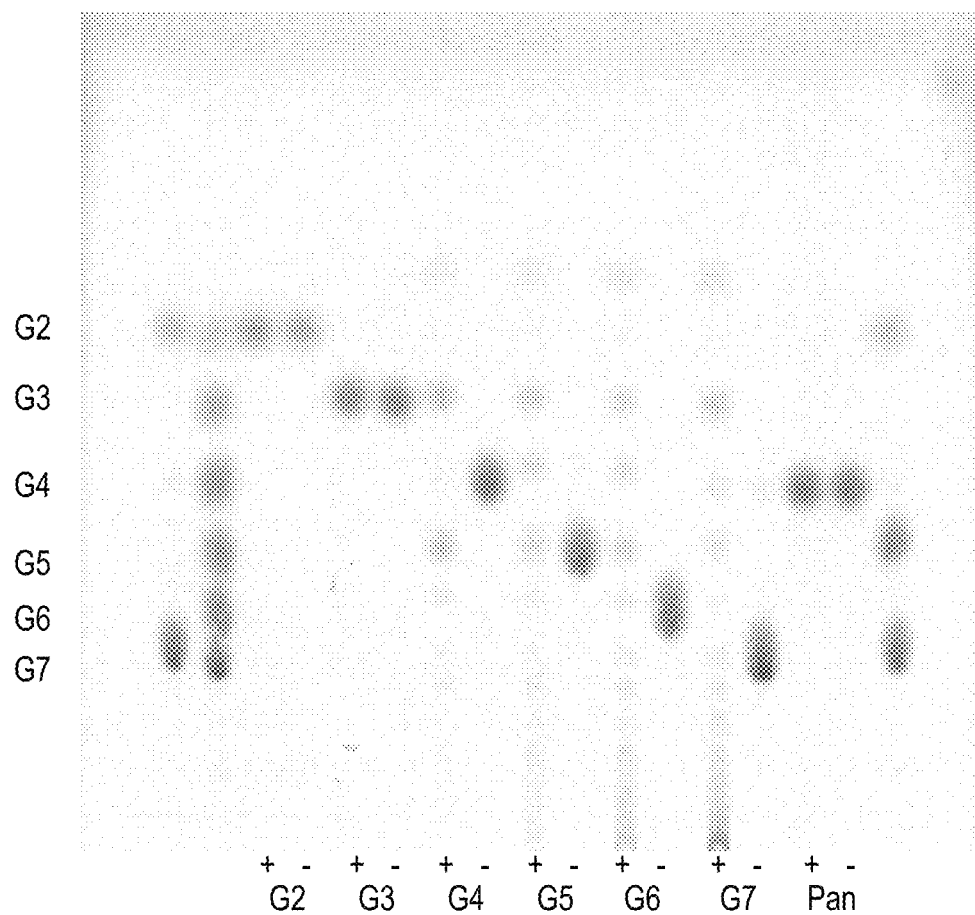
FIG. 6. TLC analysis of the reaction products of 0.0375 g/l α-GT-E incubated for h in 10 mM sodium acetate buffer, pH 5.0, containing 1 mM $CaCl_2$, with 20 mM malto-oligosaccharides. G2, maltose; G3, maltotriose; G4, maltotetraose; G5, maltopentaose; G6, maltohexaose; G7, maltoheptaose and pan; panose.
Figure 8:
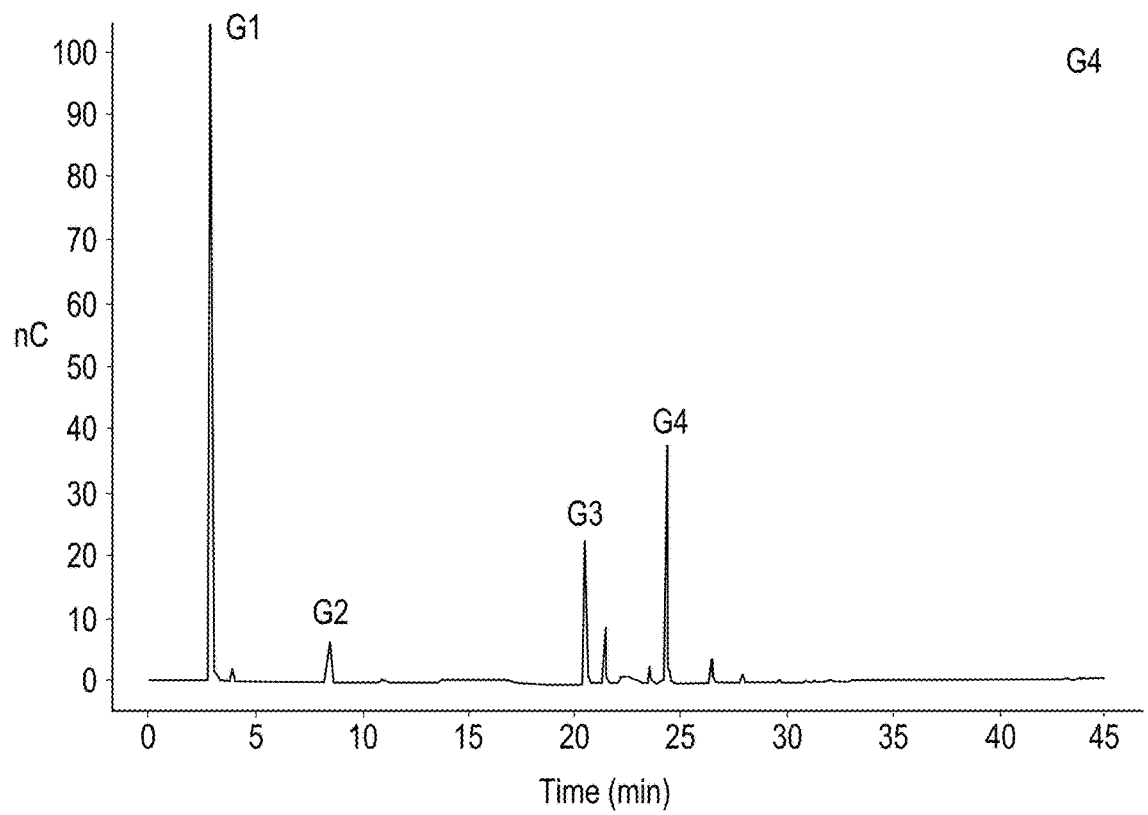
FIG. 8. HPAEC analysis of the reaction products of 0.0375 g/l α-GT-E incubated for 24 h in 50 mM sodium acetate buffer, pH 5.0, 45° C. containing 1 mM $CaCl_2$, with 20 mM maltotetraose (G4), maltopentaose (G5), maltohexaose (G6) and maltoheptaose (G7).
Figure 8:
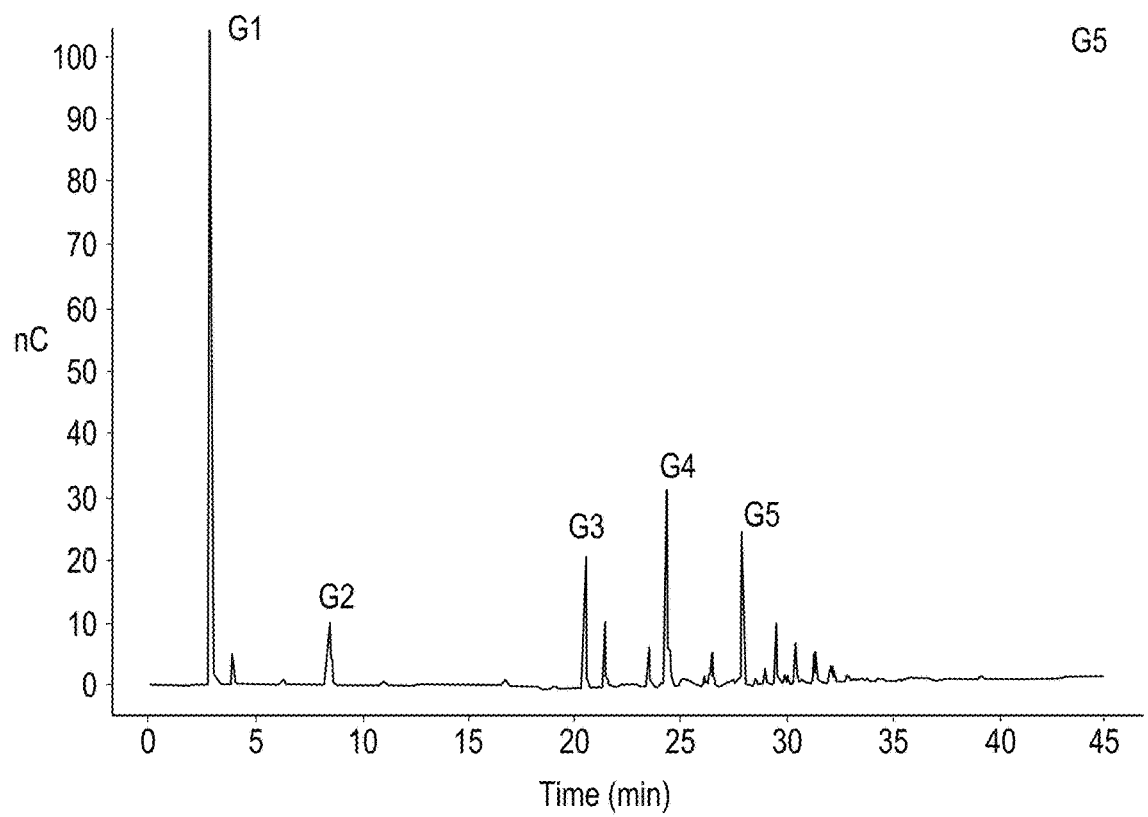
Figure 8:
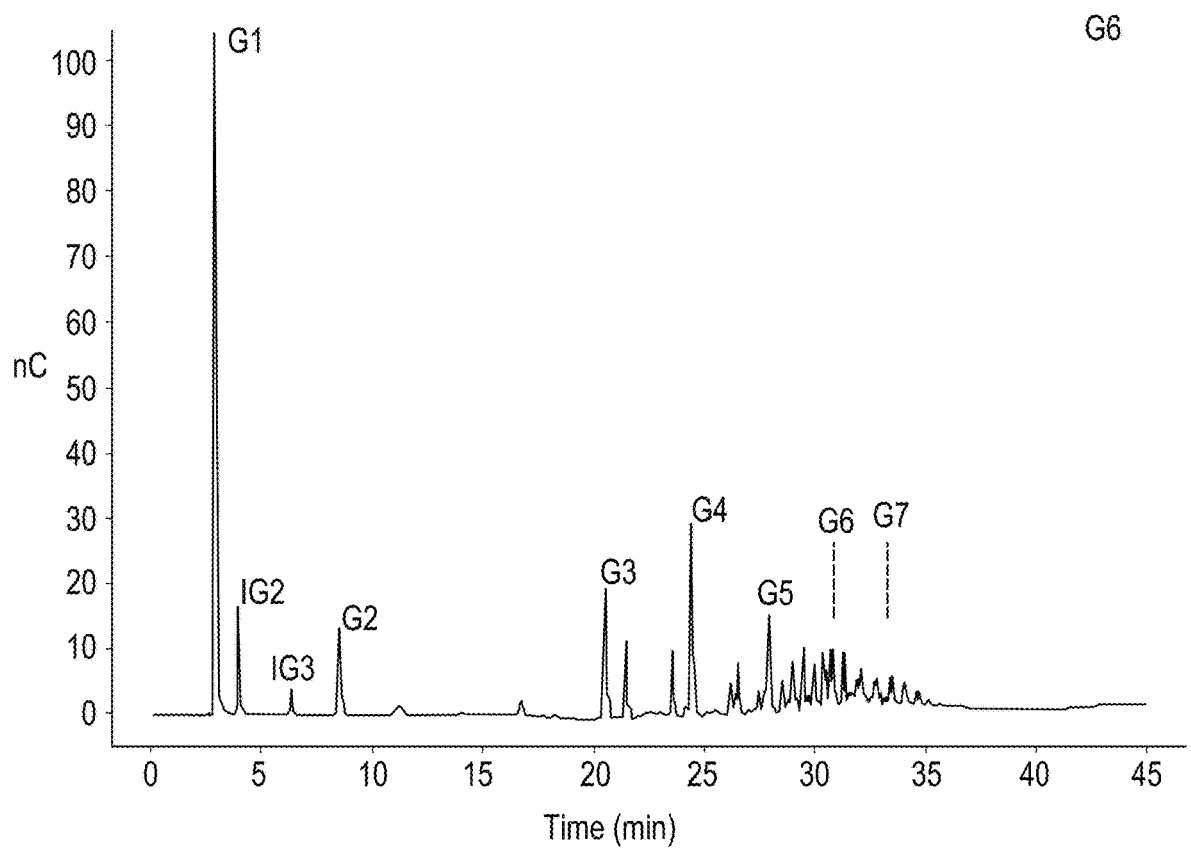
Figure 8:
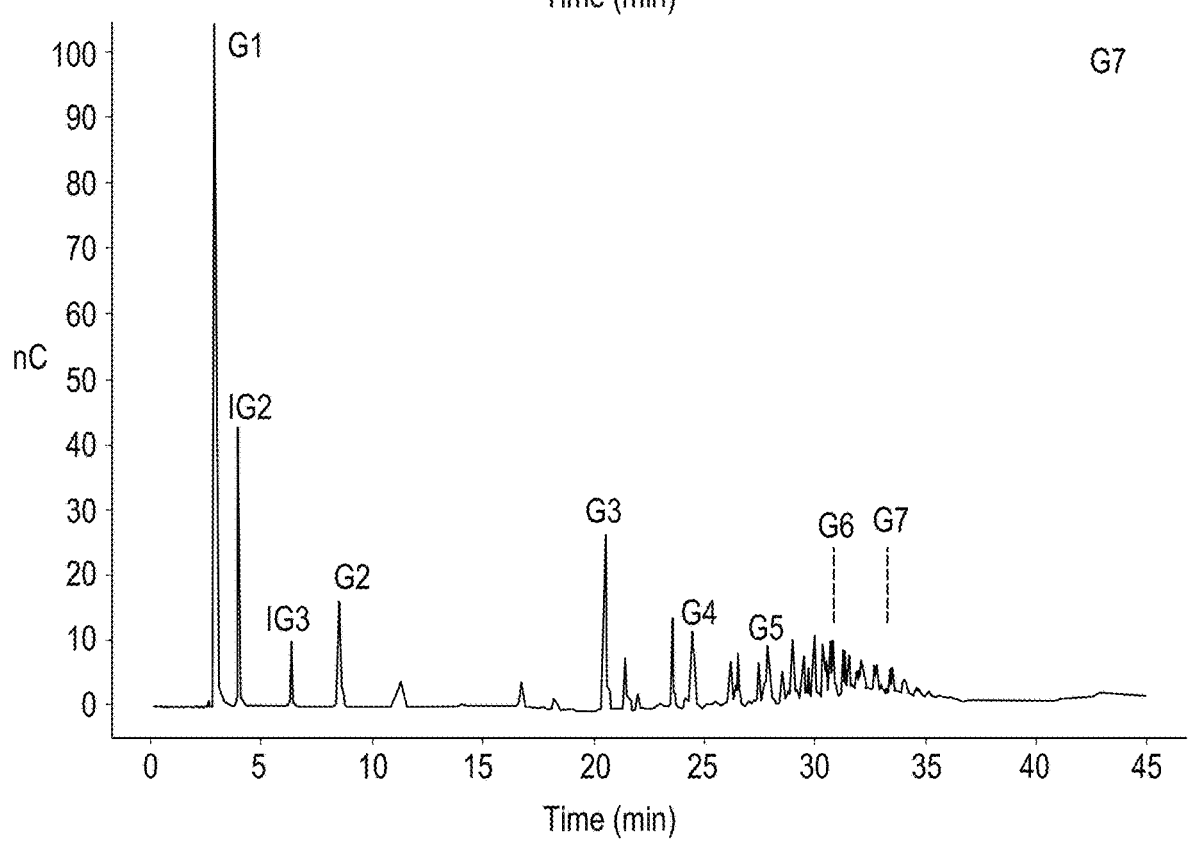
Figure 9A:
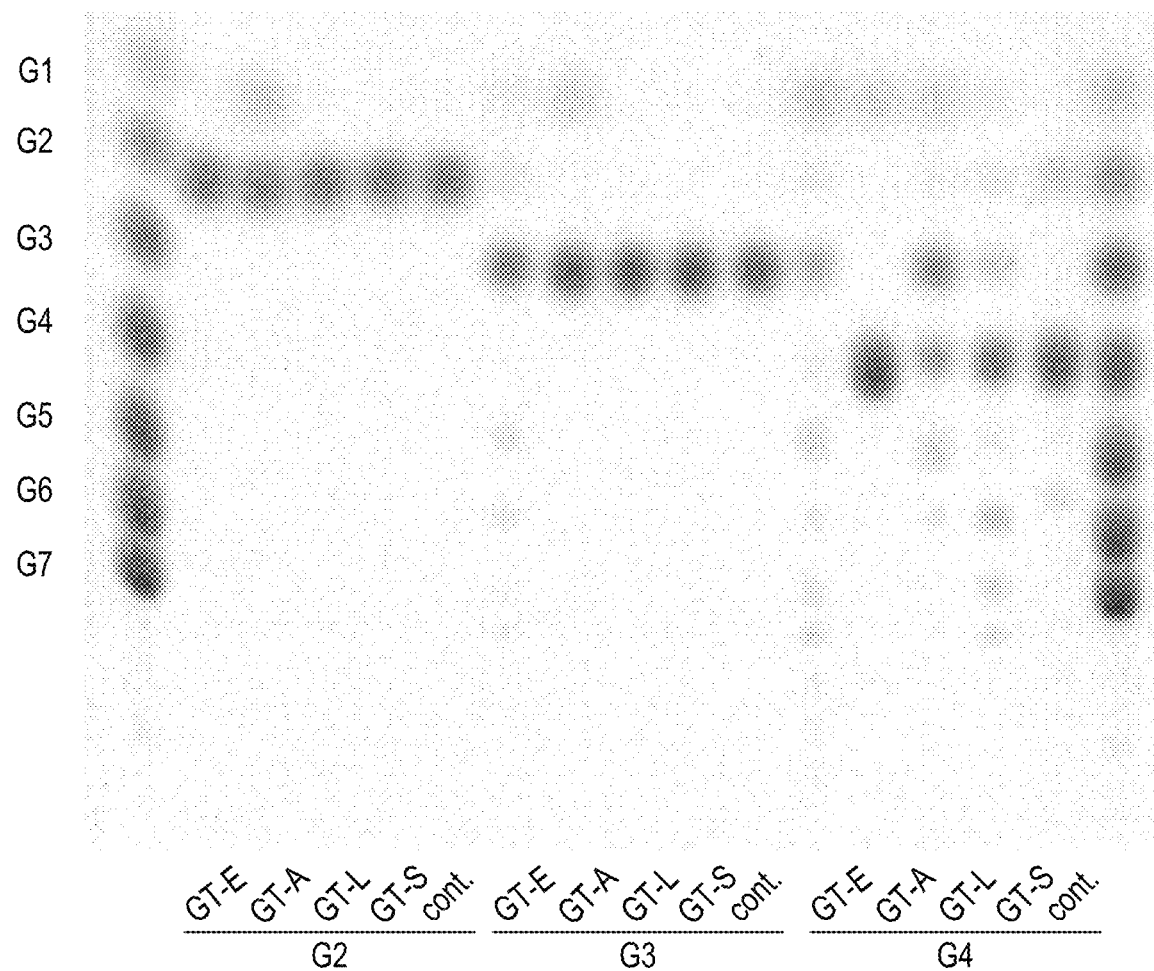
FIG. 9. TLC analysis of supernatants of different recombinant α-GT from (α-GT-E, α-GT-L, α-GT-A (no expression and no activity) and α-GT-S) incubated for 16 h in 25 mM sodium acetate buffer, pH 5.0, with A) 25 mM. G2, maltose; G3, maltotriose; G4, maltotetraose and (B) G5, maltopentaose; G6, maltohexaose; G7, maltoheptaose. Standards 14 mM G1-G7.
Figure 9B:
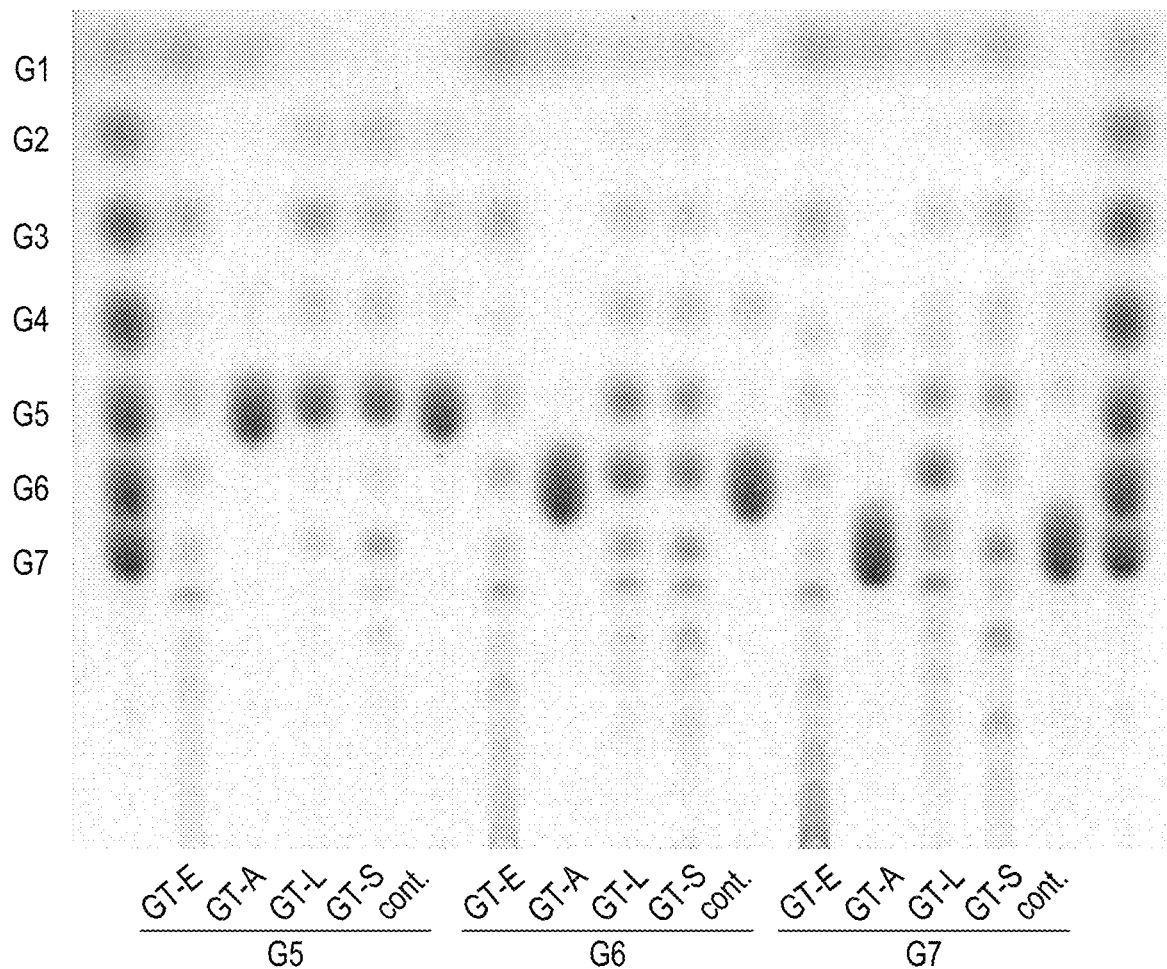

A putative α-glucanotransferase from *Exiguobacterium acetylicum* (α-GT-E), recombinantly engineered variants thereof, and active fragments thereof are disclosed. The combination of the unique α-GT-E enzyme activity, synthesizing a cocktail of glucooligosaccharides from MOS next to glucooligo's containing α-(1→4) and α-(1→6) linkages and simultaneously synthesizing isomaltooligosaccharides (IMO) such as isomaltose and isomaltotriose (FIGS. 6 and 8), together with the domain organization (FIG. 3B) prompted us to create an additional GH70 subfamily 4 (FIG. 1B and FIG. 3A). Next to α-GT-E from *Exiguobacterium acetylicum* two other members of GH70 subfamily 4 where characterized (α-GT-S) and (α-GT-L) both from *Bacillus Coagluans* sp. Both enzymes also clearly showed activity on MOS synthesizing various glucooligosaccharides (FIG. 9). The full length sequence of the α-GT-E consists of the amino acid sequence set forth in SEQ ID NO: 2. The α-GT-E may consist of amino acids 31-731 of the amino acid sequence of SEQ ID NO: 2, when expressed as a mature enzyme. The α-GT-S may consist of amino acids 33-736 of the amino acid sequence of SEQ ID NO: 7, when expressed as a mature enzyme. The α-GT-L may consist of amino acids 22-726 of the amino acid sequence of SEQ ID NO: 11, when expressed as a mature enzyme.

Figure 7A:
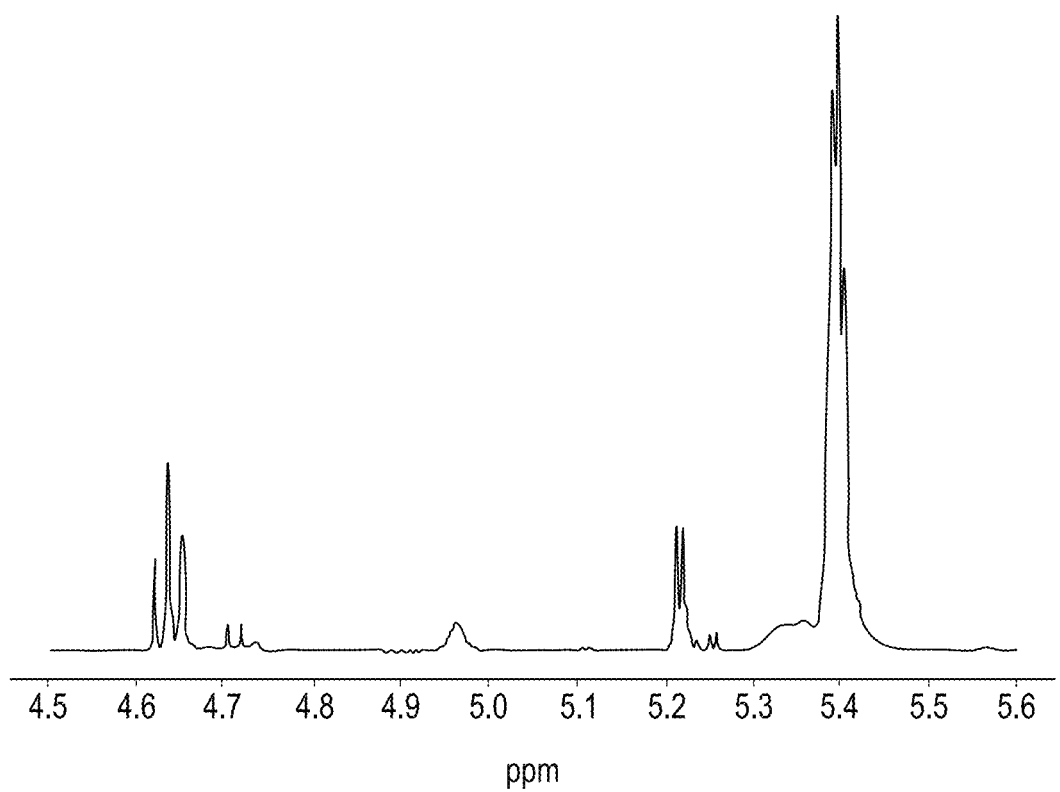
FIG. 7. 500-MHz one-dimensional $^1$H NMR analysis of (A) maltodextrin DE13-17 and (B) maltodextrin DE13-17 incubated with 10% α-GT-E supernatant for 24 h hours in 50 mM sodium acetate buffer pH 4.8.
Figure 7B:
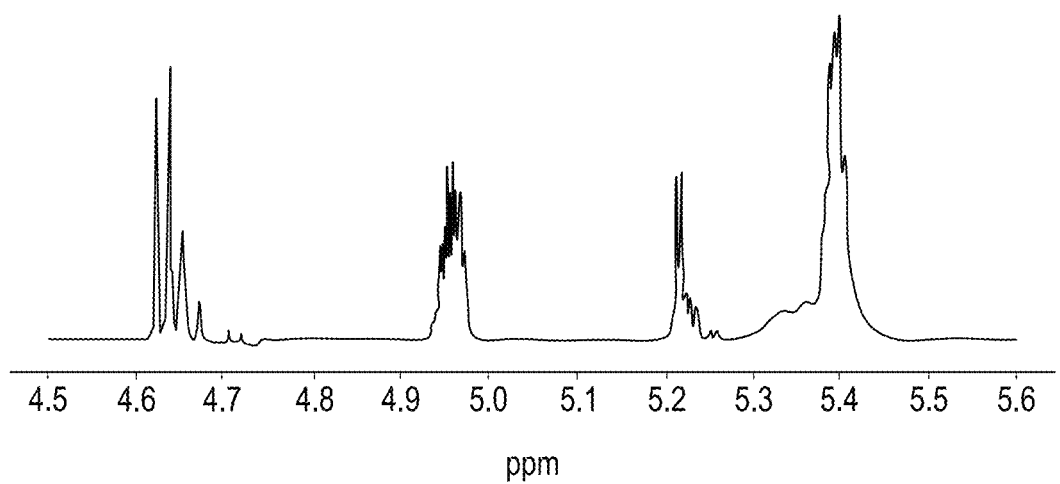
Figure 10A:
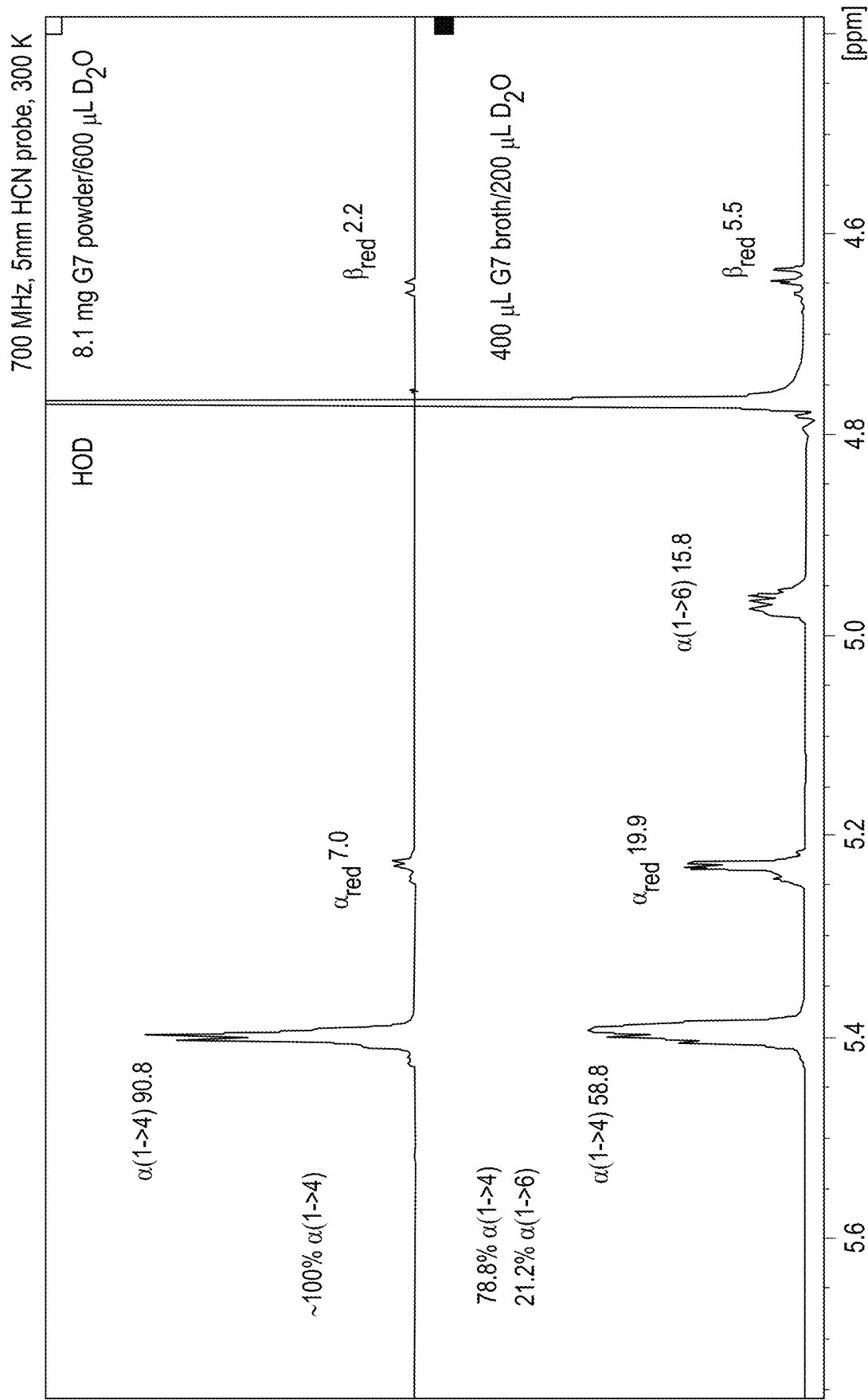
FIG. 10A: 700-MHz one-dimensional $^1$H NMR analysis of maltoheptoase (DP7) (B) maltoheptaose incubated with purified α-GT-E overnight (0.0375 g/l) in 25 mM sodium acetate buffer pH 5.0, containing 0.5 mM $CaCl_2$, at 42° C. B: 500-MHz one-dimensional $^{13}$C NMR analysis of maltoheptoase (DP7) incubated with α-GT-E as described above.
Figure 10B:
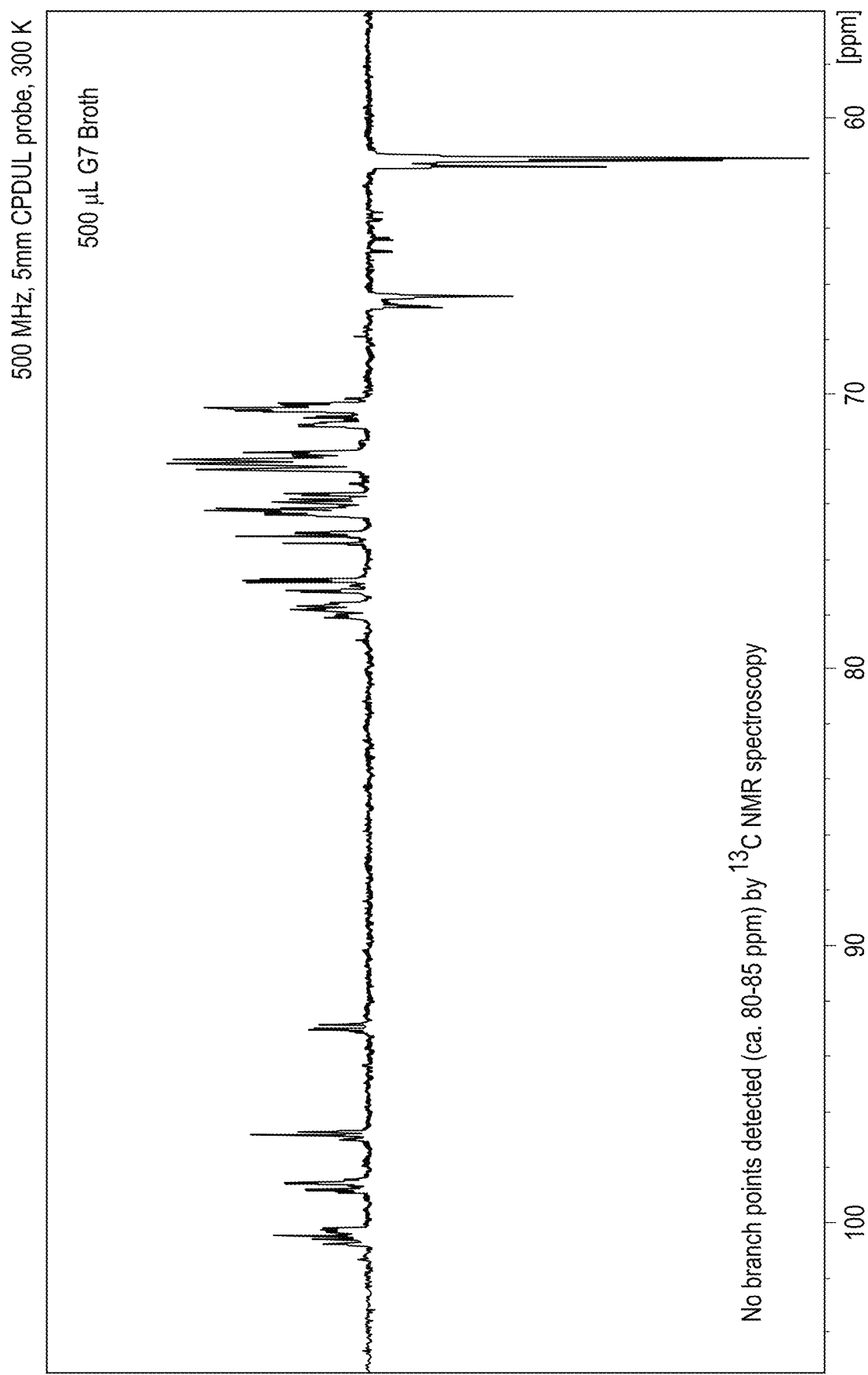

The recombinant α-GT-E enzyme is a GH70 homologue from subfamily 4 (about 27% identity to GTFA of *L. reuteri* 121 GH70_1 and about 30% identity with 4,6-α-GT-μ of *L. reuteri* 121 GH70_3) without the circularly permuted $(\beta/\alpha)_8$ barrel capable of disproportionating malto-oligosaccharides (MOS), synthesizing IMO and also introducing α-1,6 glycosidic linkages in formed products. Different α-1,4 linked saccharide substrates were used by α-GT-E to introduce α-1,6 linkages. $^1$H-NMR showed that: from maltoheptaose (DP7) 21% of α-1,6 linkages are introduced in the product (FIG. 10A), no evidence of branching was detected by $^{13}$C NMR spectroscopy (FIG. 10B), from maltodextrin DE13-17 19% of α-1,6 linkages are introduced in the product (FIG. 7). From maltodextrin DE4-7 12% of α-1,6 linkages are introduced in the product, no evidence of branching was detected by $^{13}$C NMR spectroscopy (data not shown). From soluble starch (Zulkowsky) 10% of α-1,6 linkages are introduced in the product, no evidence of branching was detected by $^{13}$C NMR spectroscopy (data not shown).

α-GT-E may comprise a polypeptide consisting of amino acids 31-731 of SEQ ID NO: 2, where additional amino acid sequences may be fused to the N-terminus and/or C-terminus of the polypeptide consisting of amino acids 31-731 of SEQ ID NO: 2. The amino acid sequences fused at either termini may contain amino acid sequences not normally associated with naturally occurring α-GT-E. For example, such amino acid sequences may be useful for labeling or purifying the protein. Such amino acid sequences also include polypeptides that confer a new function on the expressed α-GT-E. For example, a heterologous carbohydrate binding domain may be fused to the carboxyl terminus of the recombinant α-GT-E.

The α-GT-E may be "isolated," meaning that it is separated from at least some of the biological material with which it is associated in nature, and then purified and concentrated into a form that is not found in nature, e.g., in a lyophilized powder form, an encapsulated form, a coated form, a granulated form, or a liquid formulation. The α-GT-E may be "recombinantly expressed," meaning that it is expressed within a recombinant host cell from a DNA or a similar synthetic nucleic acid. A signal peptide may be operably linked to the N-terminus to facilitate secretion of the recombinantly expressed protein from an expression vector within a host cell. The signal peptide may have the sequence of amino acids 1-30 of SEQ ID NO: 2, for example. α-GT-E alternatively may be linked to a different signal sequence, such as a signal sequence from another bacterial species, e.g., another *Exiguobacterium* sp. signal sequence. The signal peptide may be proteolytically cleaved during recombinant expression to yield the mature form of the putative α-glucanotransferase.

"Recombinant α-GT-E" includes recombinantly expressed α-GT-E consisting of amino acids 31-731 of SEQ ID NO: 2, as well as recombinantly engineered variants thereof or active fragments thereof. A "recombinantly engineered variant" contains at least one amino acid substitution or deletion from the N- or C-terminus, compared to amino acids 31-731 of SEQ ID NO: 2. The amino acid sequence of a recombinantly engineered variant varies from the amino acid sequence of the naturally occurring α-glucanotransferase of SEQ ID NO: 2 by at least one amino acid. A recombinantly engineered variant may show at least 60%, at least 80%, at least 85%, at least 90%, at least 95%, at least 98%, at least 99% or at least 99.5% sequence identity with amino acids 31-731 of the amino acid sequence of SEQ ID NO: 2. Variants of α-GT-E may consist of amino acids 31-731 of the amino acid sequence of SEQ ID NO: 2, wherein the non-identical amino acids may be amino acid substitutions or deletions from either the C- or N-termini. For example, a variant with a deletion of residues 728-731 of SEQ ID NO: 2 would have at least 98% sequence identity with amino acids 31-731 of the amino acid sequence of SEQ ID NO: 2. Recombinant α-GT-E include, but are not limited to, polypeptides with 1, 2, 3, or 4 randomly selected amino acid modifications. The amino acid substitution also may be selected from the conservative amino acid substitutions shown in TABLE 1:

TABLE 1

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions, and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art and include site-directed mutagenesis, for example.

An active fragment of the recombinantly expressed α-GT-E is also provided. An active fragment of α-GT-E is a portion of α-GT-E that retains a measurable α-glucanotransferase activity, and is able to catalyze disproportionating and elongation of malto-oligosaccharides (MOS), modifying starch and in addition introducing (α1→6) glycosidic linkages in formed products.

As used herein, "percent sequence identity" means that a variant has at least a certain percentage of amino acid residues identical to the wild-type enzyme, when aligned using the CLUSTAL W algorithm with default parameters. See Thompson et al. (1994) *Nucleic Acids Res.* 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF. |

Deletions are counted as non-identical residues, compared to a reference sequence. Deletions occurring at either termini are included. For example, a variant with a deletion of residues 728-731 of SEQ ID NO: 2 would have at least 98% sequence identity, but not at least 99%, sequence identity (417/422 identical residues×100 gives 98.8% sequence identity), relative to the amino acids 31-731 of the amino acid sequence of SEQ ID NO: 2.

Amino acid modifications in the α-GT-E variants may include residues in sequence motifs that are conserved compared to other GH70 enzymes.

α-GT-E may be a component of a composition. The composition may comprise purified α-GT-E obtained from a culture of *E. acetylicum* or may comprise purified to recombinant α-GT-E, which may be expressed in a recombinantly modified host cell comprising nucleic acids encoding recombinant α-GT-E. For example, the composition may comprise a host cell that expresses nucleic acids encoding the recombinant α-GT-E. α-GT-E may have at least 50%, at least 80%, at least 90%, at least 95%, or at least 98% purity in the composition. For example, α-GT-E may be purified to homogeneity. The composition may include other components. For example, an α-GT-E composition may comprise α-GT-E as a lyophilized power and optionally one or more carriers, such as another protein without α-glucanotransferase activity. The composition also may comprise α-GT-E in a diluent, such as distilled water, distilled/deionized water, or a buffered saline solution.

Synthetic nucleic acids encoding recombinant α-GT-E, e.g., DNA, vectors comprising the nucleic acids, and host cells comprising the vector or nucleic acids are provided. A "synthetic" nucleic acid contains at least one nucleotide residue that is not found in the naturally occurring sequence depicted in SEQ ID NO: 1. The nucleic acid sequences encoding recombinant α-GT-E may comprise expression-regulating regions (e.g., promoters, enhancers, and terminators) that can be used for homologous or heterologous expression. Such expression-regulating sequences are operationally linked to a polypeptide-encoding nucleic acid sequence. As is well understood by one skilled in the art, the genetic code is degenerate, meaning that multiple codons in some cases may encode the same amino acid. Synthetic nucleic acids encoding recombinant α-GT-E include all possible codon degeneracies. Nucleic acids encoding recombinant α-GT-E may include the polynucleotide of SEQ ID NO: 1, which is the α-gt-E gene of *E. acetylicum*.

A vector may comprise the synthetic nucleic acid encoding recombinant α-gt-E. The vector may be an expression vector capable of expressing recombinant α-GT-E, for example. The vector may comprise one or more selectable markers, e.g., an antibiotic resistance gene. Vectors comprising α-gt-E-encoding nucleic acids may include those vectors that comprise the 91-2676 bp polynucleotide of SEQ ID NO: 1. Other vectors may comprise a polynucleotide consisting of the nucleotide sequence of SEQ ID NO: 1. A recombinant host cell, such as a plant, animal, fungal, or bacterial cell, containing one or more copies of the nucleic acid construct are provided. The host cell may be a bacterial cell, e.g., *Exiguobacterium* sp., which is capable of expressing and secreting the recombinant α-GT-E. Other host bacterial cells may not be *Exiguobacterium acetylicum*. A host cell may comprise the vector comprising a polynucleotide consisting of the nucleotide sequence of SEQ ID NO: 2. Suitable techniques for making and using nucleic acids encoding recombinant α-GT-E, vectors, expression constructs comprising the nucleic acids, and host cells are well known in the art.

A method of using an α-GT-E, e.g., a recombinant α-GT-E, to produce a glucooligosaccharide product is also provided. The method may comprise contacting an α-GT-E with a suitable substrate such as MOS, maltodextrin, amylose, or starch.

The α-GT-E may be provided in a composition comprising a purified α-GT-E or recombinant α-GT-E. The α-GT-E may be provided in the form of a composition comprising a cell that expresses α-GT-E, e.g., a host cell comprising a nucleic acid encoding recombinant α-GT-E. In this case, the cell may be in a non-growth state. This allows the production of the product to proceed without the necessity of supplying nutrients and other materials for supporting growth of the cells. Production can be performed by contacting the substrate?? source, such as MOS, maltodextrin, amylose, or starch, with the cells and withdrawing saccharides from the medium. The cells expressing α-GT-E may be immobilized on a carrier, such as solid particles, filters, and reactor walls. The cells may be capable of co-expressing at least one enzyme in addition to α-GT-E, such as a amylase, isoamylase, glucoamylase enzyme. For example, enzymes that may be co-expressed with α-GT-E, e.g., an isomerase, could utilize the oligosaccharide or modified starch produced during the α-GT-E-catalyzed reaction as a substrate.

The oligosaccharide or modified starch product may be chemically modified after the production process, depending on the desired application of the oligosaccharide or modified starch product. Chemical modification of starch generally involves esterification, etherification, or oxidation of the available hydroxyl groups on the α-D-glucopyranosyl units that make up the starch polymers.

A recombinant host cell capable of expressing recombinant α-GT-E may be used in a composition capable of acting as a prebiotic. The recombinant host cell can produce a glucooligo mixture. After ingestion of this glucooligo mixture, the growth of strains like *Lactobacillus* and bifidobacteria in the gut, which can metabolize the oligosaccharide will be promoted. The composition may further comprise a food-grade, feed-grade, industrial-grade, or pharmacologically acceptable carrier, diluent, or excipient. In this context, "pharmaceutically acceptable" means that the component is safe for ingestion by animals and/or humans. The composition may be administered to an animal or human. The probiotic composition may be directly ingested in conjunction with food.

The term "about" generally refers to ±15% of the referenced value. When defining a temperature, "about" refers to an average temperature during a process. The skilled artisan would expect the temperature of a process to vary somewhat about a set temperature, e.g., by ±1° C. from the set value. A temperature of "about 40° C." thus would encompass temperatures of 40±1° C. and also includes transient spikes in temperature that can occur during the process. For example, the temperature of a process may exceed 40° C. by several degrees over several minutes. These transient spikes are encompassed by "about 40° C."

EXAMPLES

Example 1

Cloning of *Exiguobacterium acetylicum* DSM20416 Putative α-Glucanotransferase (α-GT-E)

The *Exiguobacterium acetylicum* DSM20416 strain (obtained from Leibniz-Institut DSMZ—Deutsche Sammlung von Mikroorganismen und Zellkulturen GmbH) was selected as a potential source for enzymes useful in various industrial applications. The entire genome of the *E. acetylicum* DSM20416 strain was sequenced using ILLUMINA® sequencing by synthesis technology. Genome sequencing and assembly of the sequence data was performed by BaseClear (Leiden, The Netherlands). Contigs were annotated by BioXpr (Namur, Belgium). One of the genes identified this way in *E. acetylicum* DSM20416, SEQ ID NO: 1, encodes a putative α-glucanotransferase identified herein as "α-GT-E". The amino acid sequence of the full length enzyme encoded by α-GT-E is set forth as SEQ ID NO: 2. The amino acid sequence of the mature α-glucanotransferase encoded by α-GT-E is set forth as SEQ ID NO: 3.

At the N-terminus, α-GT-E has a signal peptide with a predicted length of 30 amino acids (in bold italics in SEQ ID NO: 2) as determined using SignalP-NN (Emanuelsson et al., Nature Protocols, 2:953-971, 2007). The presence of a signal sequence indicates that this putative α-glucanotransferase is a secreted enzyme.

The amino acid sequence of the mature α-glucanotransferase C-terminally truncated as determined by mass-spec analysis of the expressed protein in Bacillus encoded by α-GT-E AA31-731 [FAPS . . . KAPV] (~79 009 Da) is set forth as SEQ ID NO: 4.

Example 2

Heterologous Expression of α-GT-E, α-GT-S and α-GT-L

Figure 1:
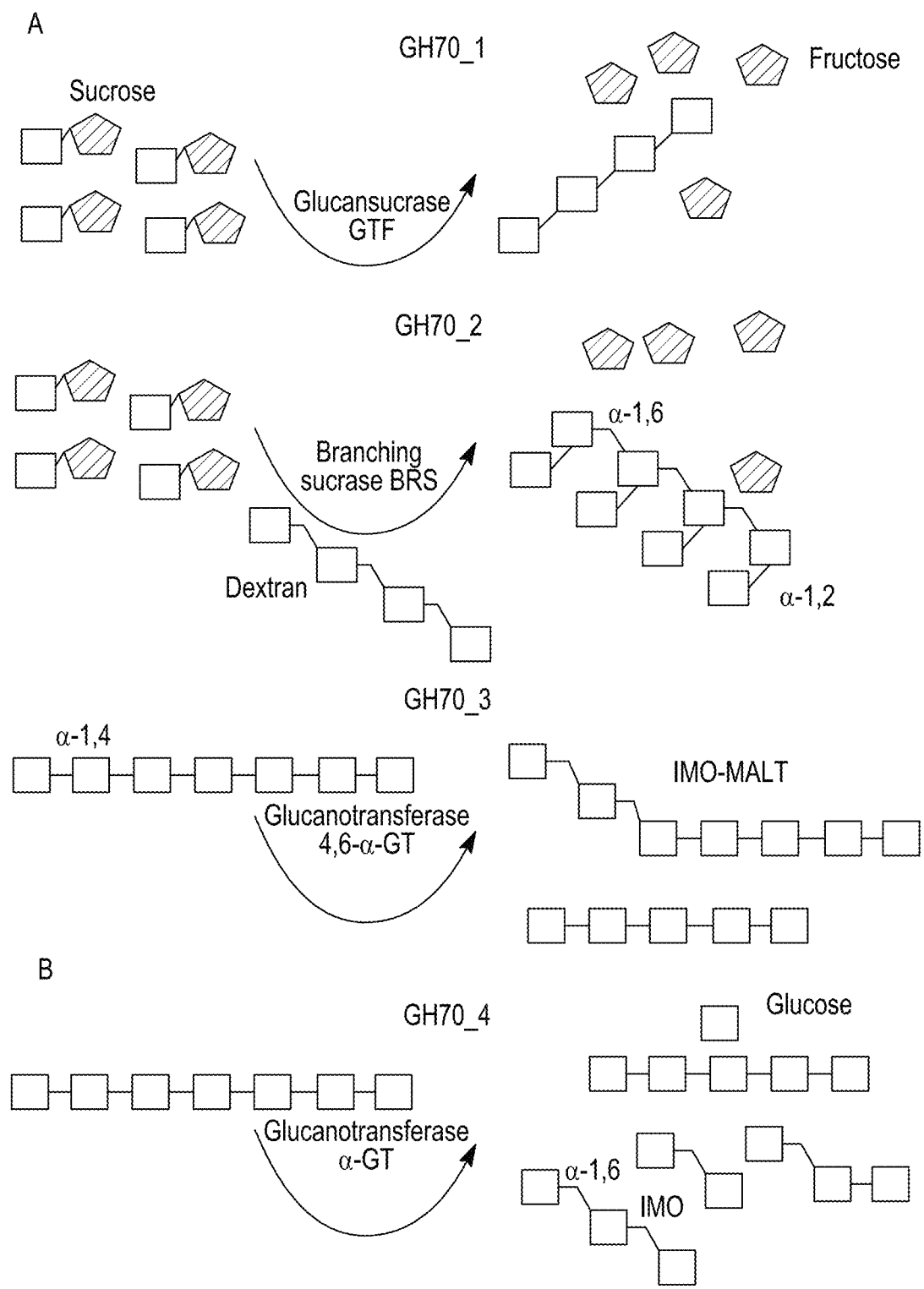
FIG. 1. A) Diagram showing the different GH70 subfamilies (1) The common GH70 GTFs using sucrose as substrate, synthesizing α-glucan polymers, 2) Branching GH70 BRS using sucrose as donor and dextran as acceptor introducing α-1,2 and α-1,3 branches in the dextran backbone, 3) 4,6-α-GTs using MOS and starch as substrate introducing α-(1→6) glycosidic bonds. B) The new GH70 subfamily 4) α-GT, the only GH70 member without the circular permuted $(\beta/\alpha)_8$ barrel structure and hence the GH13 order of conserved regions, using MOS and maltodextrin as substrate.
Figure 2:
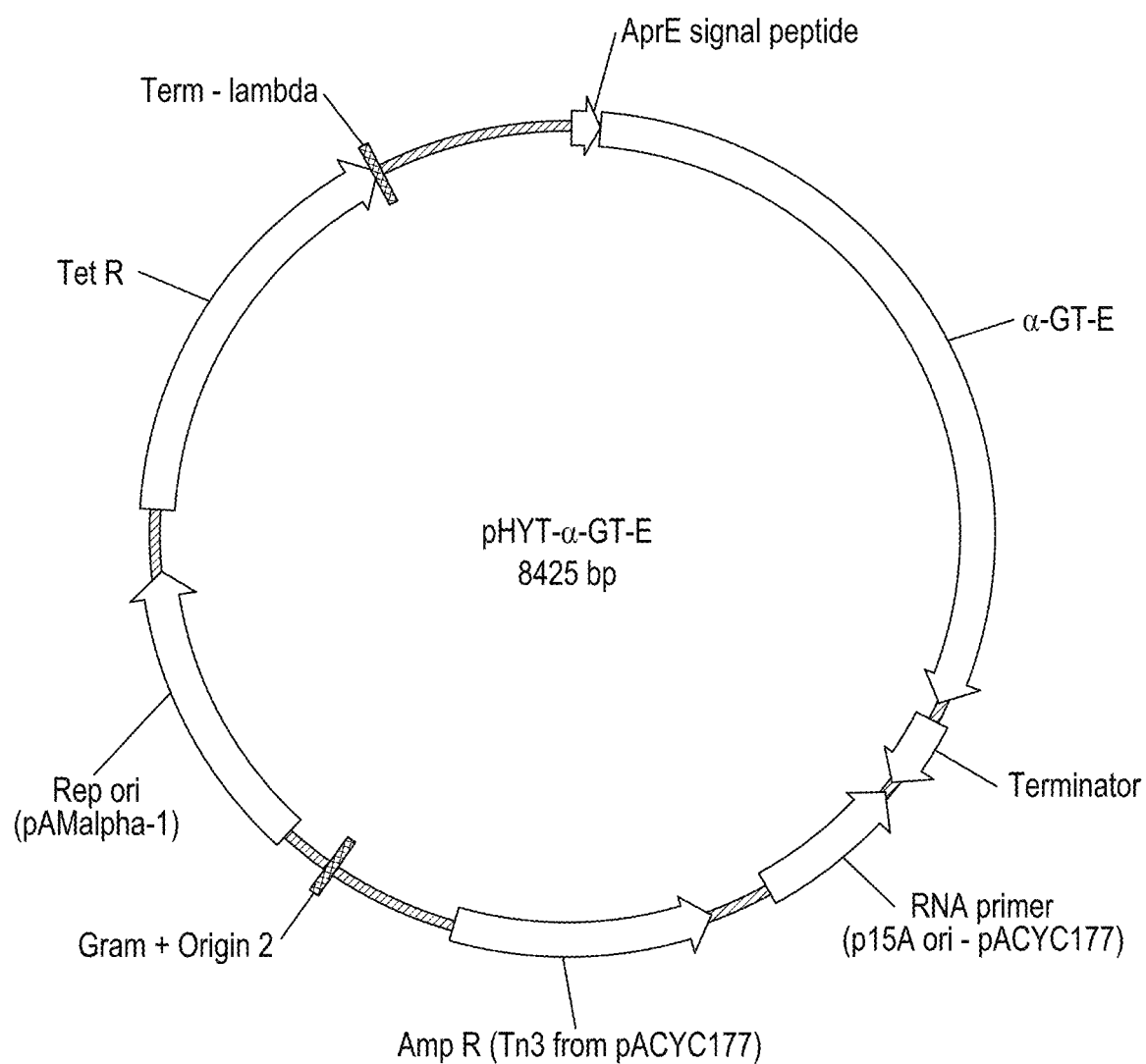
FIG. 2. Plasmid map of pHYT-α-GT-E

The α-GT-E α-glucanotransferase was produced in B. subtilis using an expression cassette consisting of the B. subtilis aprE promoter, the B. subtilis aprE signal peptide sequence, the mature putative α-glucanotransferase and a BPN' terminator. This expression cassette was cloned into the pHYT replicating shuttle vector and transformed. The pHYT vector was derived from pHY300PLK (Takara) by adding a terminator after the tetracycline resistance gene using the BstEII and EcoRI sites (terminator sequence: GGTTACCTTG AATGTATATA AACATTCTCA AAGG-GATTTC TAATAAAAAA CGCTCGGTTG CCGCCGGGCG TTTTTTATGC ATCGATGGAA TTC). The HindIII site in pHY300PLK was also removed using a linker cloned into the BamHI and HindIII sites (linker sequence: GGATCCTGAC TGCCTGAGCT T). A map of the pHYT vector for expression of the putative α-glucanotransferase (pHYT-α-GT-E) is shown in FIG. 1.

A synthetic gene encoding the mature region of α-GT-E that it is modified by introducing several silent codon changes was cloned into the pHYT vector. The nucleotide sequence for this alternative α-GT-E gene is shown in SEQ ID NO: 5. Similarly, constructs of α-GT-S from Bacillus Coagulans 2-6 and α-GT-L and Bacillus Coagulans 2022696 in pHYT were made, their synthetic nucleotide sequence is shown in SEQ ID NO: 9 and 13, respectively.

α-GT-E Gene Expression and Purification of α-GT-E

To produce α-GT-E, a B. subtilis transformant containing pHYT-α-GT-E was cultivated in Tryptone Soya Broth (Oxoid Ltd., UK) and Grant's II medium. See U.S. Pat. No. 8,507,244 B2. Heart Infusion agar plates (Difco Laboratories, MI) were used to select transformants. Plasmid integrity was maintained by the addition of 25 μg/mL tetracyclin. After incubation (3 days at 32° C.), α-GT-E was detected in the growth medium. After centrifugation and filtration, culture supernatants with α-GT-E were used for assays and purification. A similar approach was used to express α-GT-S and α-GT-L.

Enzyme present in the supernatant was purified to homogeneity by anion exchange chromatography using an AKTA Explorer System (GE Healthcare) equipped with a 5 ml HiTrap Q HP column (GE Healthcare) and a linear gradient of 100 ml with 1 M NaCl in 20 mM Tris buffer pH 7.5 as eluens at a flow rate of 5 ml·min$^{-1}$. Proteins present in the elution peak, as judged by SDS-PAGE, were desalted (Slide-A-Lyzer Dialysis Cassette 10 kDa MWCO, Pierce) using 10 mM NaAc pH 5.0. Protein concentrations were determined using the Bradford method using the Bio-Rad reagent and BSA (bovine serum albumin) as a standard (Bio-Rad).

Protein Mass Spectrometry Analysis

The purified protein was precipitated and dissolved in 8M urea and reduced with DTT, alkylated with iodoacetamide (IAA) and digested using Trypsin, α-Chymotrypsin and an Endoproteinase GluC as preparation for mass spectrometry analysis. The tryptic digest (10 μl) was separated by RP-HPLC on a Phenomenex Aeris Peptide XB-C18 column, 150×2.1 mm, 3.6μ. The elution gradient is formed from 0.1% (v/v) formic acid in water (solvent A) and 0.1% (v/v) formic acid in acetonitrile (solvent B) at a flow rate of 0.3 ml·min$^{-1}$. The column compartment was operating at 50° C. The protein fragments were identified using the α-GT-E protein sequence as search model.

Amino Acid Sequence Alignment of α-GT-E from E. acetylicum DSM20416 and Phylogenetic Tree Construction Multiple amino acid sequence alignments of α-GT-E and homologues (without the circularly permuted (β/α)$_8$ barrel) were made with the ClustalW interface in MEGA version 4 (www.megasoftware.net) with gap-opening and extension penalties of 10 and 0.2, respectively. The same program was used to construct the phylogenetic tree of αGTE and homologues. Amino acid sequences were acquired from a blast search using αGTE as search model. Bootstrap test of phylogeny was performed by the neighbour-joining method using 500 replicates.

pH and Temperature Optima

The α-GT-E pH optimum was determined by measuring the increase in amount of reducing sugars released at 37° C. from 2% Zulkowsky starch in 30 min by 0.0375 g/l α-GT-E in 186.5 mM universal buffer ranging from pH 2 to pH 12. The α-GT-E pH temperature optimum (22-74° C.) was determined similar as for the pH optimum using 186.5 mM universal buffer pH 5.0

Universal buffer was prepared as follows, 1 M acetic acid, 1 M boric acid and 1 M phosphoric acid was adjusted to pH 7.0 and final concentration of 0.75M using 4M NaOH. This solution adjusted with 4M NaOH or 4M HCl to prepare pH buffers ranging from pH 2-12. PAHBAH reducing sugar reagent (for 100 ml reagent: 1 g p-hydroxybenzoic acid hydrazide (Sigma # H9882), 16 g Potassium sodium tartrate tetrahydrate dissolved in 2% NaOH), (Lever, Anal Biochem, 47:273-279, 1972). 5 μl of incubation sample was added to 100 μl PABAH reagent, incubated for 3 min at 99° C. Absorbance (endpoint) was measured at 410 nm in a spectrophotometer.

Incubations of Malto-Oligosaccharides (MOS) and Other Saccharide Substrates with α-GT-E A) Purified Enzyme: i) TLC & HPAEC analysis: α-GT-E (0.0375 g/l) and 20 mM of sucrose (data not shown) and MOS with a different degree of polymerization (G2-G7) and panose were incubated separately for 5 h in 50 mM sodium acetate buffer, pH 5.0 containing 1 mM CaCl$_2$ at 45° C.

ii) NMR analysis: α-GT-E (0.0375 g/l) and 0.83% Amylose type III (solubilised with 1M NaOH and neutralized with 1M HCL), 0.83% Zulkowsky starch, 0.83% maltodextrin DE4-7 and maltoheptaose (G7) were incubated separately overnight in 25 mM sodium acetate buffer, pH 5.0 containing 0.5 mM CaCl$_2$, at 42° C.

B) Supernatant ii) NMR analysis, 10% B. subtilis supernatant expressing α-GT in 50 mM sodium acetate buffer, pH 4.8 was incubated with 50 g/l maltodextrin DE13-17 incubated at 30° C. for 24 h.

Thin-Layer Chromatography (TLC) and High-Performance Anion-Exchange Chromatography (HPAEC)

For TLC analysis of saccharide product mixtures, 1-3 μl sample was applied onto a silica gel 60 F254 plate (Merck, Darmstadt, Germany), and after drying, the plate was run for 6 h or ON in butanol/ethanol/H$_2$O, 5/5/3 (v/v/v). Then, the plate was dried, sprayed with 50% H$_2$SO$_4$ in methanol and left to develop for 10 min at 110° C.

For HPAEC, appropriate dilutions (in H$_2$O) of quenched (10 min 95° C.) enzyme reaction mixtures were subjected to analysis. A mixture of MOS (DP1-DP7) and a maltodextrin DE 4.0-7.0 solution were used as standards.

Sugars were separated using a CarbopacPA200 column (Thermo Scientific) with ultrapure water (eluent A), 1 M NaOH (eluent B), and 0.5 M NaAc (eluent C) as solvents at a flow rate of 0.50 mL/min, injection volume 5 10 μL, column temperature 30° C., and detector temperature 20° C. The following gradient of eluents A, B, and C was used: eluent A (0 min, 95%); (15 min, 90%); (30 min, 72%); (40 min, 40%); (45.1 min, 95%); eluent B (0 min, 5%); (15 min, 10%); (45.1 min, 5%); and eluent C (0 min, 0%); (30 min, 18%); (40 min, 50%); (45.1 min, 0%).

Detection was performed with an electrochemical detector (Thermo Scientific) with an Au working electrode and an Ag/AgCl reference electrode. Waveform: Gold Standard PAD (standard quad potential): +0.1 Volt (0-0.40 s); −2.0 Volt (0.41-0.42 s); 0.6 Volt (0.43 s); −0.1 Volt (0.44-0.50 s). Data were integrated using Chromeleon software (Thermo Scientific).

(ii) Nuclear magnetic resonance (NMR) spectroscopy. One-dimensional $^1$H NMR spectra of the ca-GT-E incubated with maltodextrin DE 13-17 [and other samples?] samples were acquired on an Agilent DD2 spectrometer (Agilent Technologies, Inc., Santa Clara, Calif.) operating at 500 MHz for $^1$H using a 5 mm cryogenic triple-resonance pulsed-field gradient probe. Water suppression was obtained by carefully placing the observe transmitter frequency on resonance for the residual water signal in a "presat" experiment, and then using the first slice of a NOESY-presat experiment with a full phase cycle (multiple of 32) and a mix time of 10 ms. One-dimensional $^1$H spectra were acquired with a spectral width of 6410 Hz, acquisition time of 5.1 s, 65536 data points, 4 s presaturation and a 90-degree observe pulse. Signal averaging involved accumulation of 64 scans. Sample temperature was maintained at 25° C.

Samples were prepared by adding 50 μL of reaction mixture to a 5 mm NMR tube along with 60 μL of D$^2$O containing 12.4 mM 4,4-dimethyl-4-silapentane-1-sulfonic acid sodium salt (DSS) as internal chemical shift reference, and the balance (450 μL) of D$_2$O for a total volume of 560 μL. The DSS methyl resonance was set to 0 ppm.

1. Hu Y, Ketabi a., Buchko a., Ganzle M G. 2013. Metabolism of isomaltooligosaccharides by *Lactobacillus reuteri* and bifidobacteria. Lett. Appl. Microbiol. 57:108-114.
2. Pan Y C, Lee W C. 2005. Production of high-purity isomaltooligosaccharides syrup by the enzymatic conversion of transglucosidase and fermentation of yeast cells. Biotechnol. Bioeng. 89:797-804.
3. Aslan Y, Tanriseven A. 2007. Immobilization of *Penicillium lilacinum* dextranase to produce isomaltooligosaccharides from dextran. Biochem. Eng. J. 34:8-12.
4. Hijum S A F T Van, Kralj S, Ozimek L K, Dijkhuizen L, Geel-schutten I G H Van. 2006. Structure-Function Relationships of Glucansucrase and Fructansucrase Enzymes from Lactic Acid Bacteria 70:157-176.
5. Leemhuis H, Pijning T, Dobruchowska J M, van Leeuwen S S, Kralj S, Dijkstra B W, Dijkhuizen L. 2013. Glucansucrases: Three-dimensional structures, reactions, mechanism, α-glucan analysis and their implications in biotechnology and food applications. J. Biotechnol. 163:250-272.
6. Robyt J F, Eklund S H. 1983. Relative, quantitative effects of acceptors in the reaction of *Leuconostoc mesenteroides* β-512F dextransucrase. Carbohydr. Res. 121:279-286.
7. Hellmuth H, Wittrock S, Kralj S, Dijkhuizen L, Hofer B, Seibel J. 2008. Engineering the glucansucrase GTFR enzyme reaction and glycosidic bond specificity: toward tailor-made polymer and oligosaccharide products. Biochemistry 47:6678-6684.
8. Kralj S, Van Geel-Schutten I G H, Faber E J, Van Der Maarel M J E C, Dijkhuizen L. 2005. Rational transformation of *Lactobacillus reuteri* 121 reuteransucrase into a dextransucrase. Biochemistry 44:9206-9216.
9. Vujicic A, Pijning T, Kralj S, López C A, Eeuwema W. 2010. Crystal structure of a 117 kDa glucansucrase fragment provides insight into evolution and product specificity of GH70 enzymes. Proc. Natl. Acad. Sci.
10. Stam M R, Danchin E G J, Rancurel C, Coutinho P M, Henrissat B. 2006. Dividing the large glycoside hydrolase family 13 into subfamilies: Towards improved functional annotations of a-amylase-related proteins. Protein Eng. Des. Sel. 19:555-562.
11. Bozonnet S, Dols-Laffargue M, Fabre E, Pizzut S, Remaud-Simeon M, Monsan P, Willemot R M. 2002. Molecular characterization of DSR-E, an α-1,2 linkage-synthesizing dextransucrase with two catalytic domains. J. Bacteriol. 184:5753-5761.
12. Passerini D, Vuillemin M, Ufarté L, Morel S, Loux V, Fontagné-Faucher C, Monsan P, Remaud-Siméon M, Moulis C. 2015. Inventory of the GH70 enzymes encoded by *Leuconostoc citreum* NRRL B-1299-identification of three novel α-transglucosylases. FEBS J. n/a-n/a.
13. Kralj S, Grijpstra P, van Leeuwen S S, Leemhuis H, Dobruchowska J M, van der Kaaij R M, Malik A, Oetari A, Kamerling J P, Dijkhuizen L. 2011. 4,6-A-Glucanotransferase, a Novel Enzyme That Structurally and Functionally Provides an Evolutionary Link Between Glycoside Hydrolase Enzyme Families 13 and 70. Appl. Environ. Microbiol. 77:8154-63.
14. Leemhuis H, Dijkman W P, Dobruchowska J M, Pijning T, Grijpstra P, Kralj S, Kamerling J P, Dijkhuizen L. 2013. 4,6-α-Glucanotransferase activity occurs more widespread in *Lactobacillus* strains and constitutes a separate GH70 subfamily. Appl. Microbiol. Biotechnol. 97:181-93.
15. Dobruchowska J M, Gerwig G J, Kralj S, Grijpstra P, Leemhuis H, Dijkhuizen L, Kamerling J P. 2012. Structural characterization of linear isomalto-/malto-oligomer products synthesized by the novel GTFB 4,6 α-glucanotransferase enzyme from *Lactobacillus reuteri* 121. Glycobiology 22:517-528.
16. Leemhuis H, Dobruchowska J M, Ebbelaar M, Faber F, Buwalda P L, Maarel M J E C Van Der, Kamerling J P, Dijkhuizen L. 2014. Isomalto/Malto-Polysaccharide, A Novel Soluble Dietary Fiber Made Via Enzymatic Conversion of Starch.
17. 2010. gluco-oligosaccharides comprising a1,4 and a1,6 glycosidic bonds, use thereof, and methods for providing them.

SEQUENCE LISTING

SEQ ID NO: 1: [nucleotide sequence α-GT-E]
ATGAACAAGGCGAAAAAGTCTCAACAGGTTTGCTTGCGGCATTGGTAGCGACAAGCGGACTGACGTATGCACCAGAAAGCGC
AAAGGCTTTCGCACCAAGTGAAAAACTCGATAACCGCGTTATTTTCCAAAGCTTCAGCCTGTATCAACCATACGAAAGCAACA
TGTACCGGACGCTTGCTAAAAAAGGTGAGTTGCTCAATTCGTGGGGTGTGACAGATGTGTGGTTACCACCTGCATATCGTTCA
TTCGATATGGCACGTTACATGGAAGGATATGCAATCGCTGACCGTTATGACCTTGGTGAATTCCCACAAGGACCAGGTGGATC
GGTTGCGACGAAATACGGAAAAGCCACACAACTCGAGATGATGGTCGACATGTTGCATGACGACAACATCAAAGTCCAGATGG
ACCTCGTTCCAAACCAAATGCTCGGTCTCAACAAACGTGAAGCTGTCTTCGTTCGTCGTGCGACAAGTTCAGGTGAGCCGTTC
ATGAACCCATTCACAGGTGGAGAAAAAACGAAGACCCTCGCAACGCCTTACCTCGCTTACACAAAAGGTGGCGGTATGGGACA
AGAGAAGTACGGTTACCTCAAAGAGTGGAACAAATCATTCATCAATGGAACATCACTGCAAGGGCAGGGTATGGGGCGCGTCA
TGACGGACAAAGACGGTAAACCGTACCGTTACTTCGGTAAAGACGATGCGAACAACTACTTACCAGAATGGTTGCTTGACGCA
GCGAAGACACAGAACTTGAATGTCGTCGATACGTACCTCGCAGCAGACGGTTGGTATGAAGTCTCACCAGAGAACTGGAAGCC
GATGCTTTCGCAATATGCGAAGGATGAAGGATACCTCGAGTACATGAAACAAAACGGCTTCGAAACAAAAGAAGCTTTGCTTA
CTTCAACGGAAAACACCAAGATCGCTTCGTTGACGGAAGAATACATGAAGACACAAGCTGCGTACGGTTATGGGTCAGAAGAA
CGTTCATACCAAAACGATAACTCAGGAATCGATATCGAAGATCAGTTCCTCTTCGTTGATGAGACTGGTTTCCCAACACAGGC
ATACAACAAAACGATGACGAACAACGATGAGTTCTTGATCGGTGTCGACCTTGCGAACTCGAACCCAGAAGTCATCAAGGAAC
AAAAGAACTGGATGAAGTGGATGCTTGAAACGTACAAGTTCGACGGTTTCCGGATTGATGCTGCGTCGCACTACGATACGGCG
ATCCTCAAAGCAGAAGCGGAAATTTCAAAAGCACACTTCGGGAAACAAGATTACCTCAGCTATATCGAGAGCTATAAAACAGA
ACAGAATGCTTACATGAAAGCAAACAATAACGAGCAACTCGTCATGGACGGAGAGCTTTACTTCACGCTCCGTTCAGCACTCA
CACCATCGAACAAACGTGCACTCCGTGACTTAGCGAAAGTCTCAGTCGTTAACCGTGAAGGTGACGGCGCGACAAACGTTCAA
GCGAACTGGTCATTCGTCAACAACCATGACCAAGAGAAAAACCGCGTCAACCAAATCATGCTTGATGCGTACGGCATCAAAAC
GAATACGCAGTACGGAAAAGACGGCGAGCCGAAATCGTTCGAGAAGCTCTACAATAAAGAAGATGAAGCGAAGGCACTTGCGA
TCTACAACAAAGAACTCGCAAGTCCAACGAAGAAATACTCGACGGAAAACGTCGTCGCGCAATACGCGTTCCTTCTTTCGAAC
AAAAACACGGTGCCAACGGTCTACTACGGTGATCTCTACCAGACGGATGCATCGTACATGTCGAAAACGACACCGTACTATGA
TGAAATCACGAATCTCCTAAAAGTCCGTAAACAGTATGCGTATGGTAAACAACACGTTGCGTACCACACATCGAACACGTCAA
AAGAAGCGGGTAAAGACTTGATCTCAAGCGTCCGTTTCGGAAAAGACCGCAACACAGGTGTCGCGACAGTCATCGGGAAAAAC
GCAGCGCTTGATACGACGGTTCAAGTCAACATGGGTAAAACACACGCGAACCAAGTCTTCGTTGATGCTAGTGGCGTTACGAA
CACGAAACTCGTCACAGATAAGAACGGTATCTTGACGGTTCCAGTCAAAGGTATCAAAACAGCAGAAGTCAACGGTTACGTCG
GCGTCTTCGTTCCACAAGCAACAAAAGCGCCAGTTGCAGCAATCAAAGCAGGTGCTGTCTACCAAGGAAAAGCACTCGACTTG
AAAACGACAGTTACGAACACGACATCAGCAGTTGCGTCAACACGCTACCGTGTCCTTGATACGAAAAAAGCGACAGTTGATTC
AAAAGGTCGTCTGACAGGTAAAGCAACAGGTAAGACGACGGTTGAAGCAACAGTTACGTTAAAAGACGGTTTTGTCTTGAAAA
CAGTTTTACCGATCGAAACAAAAGCGAACAGCGTCACGCTGAAAGCAACAAAAGCAACACTCAAGAAGAACCAGACGACACGT
ATCGCGTATACGTCAGCAACGGATAAGATCAAATCTGTTCAGTATGCGTCAGCGAACAAAAAAGTCGCGCAAGTCTCGTCACG
TGGTAACGTGAAAGGGATCAAAGCAGGCAAAACGACGATCCGTGTCACATACACGACAGTAGGAAACTACAAAGTCGTCAAAA
CGTTCACAGTCACAGTCAAG SEQ ID NO: 2-[amino acid sequence α-GT-E]
MNKAKKVSTGLLAALVATSGLTYAPESAKAFAPSEKLDNRVIFQSFSLYQPYESNMYRTLAKKGELLNSWGVTDVWLPPAYR
SFDMARYMEGYAIADRYDLGEFPQGPGGSVATKYGKATQLEMMVDMLHDDNIKVQMDLVPNQMLGLNKREAVFVRRATSSGEP
FMNPFTGGEKTKTLATPYLAYTKGGGMGQEKYGYLKEWNKSFINGTSLQGQGMGRVMTDKDGKPYRYFGKDDANNYLPEWLLD
AAKTQNLNVVDTYLAADGWYEVSPENWKPMLSQYAKDEGYLEYMKQNGFETKEALLTSTENTKIASLTEEYMKTQAAYGYGSE
ERSYQNDNSGIDIEDQFLFVDETGFPTQAYNKTMTNNDEFLIGVDLANSNPEVIKEQKNWMKWMLETYKFDGFRIDAASHYDT -continued AILKAEAEISKAHFGKQDYLSYIESYKTEQNAYMKANNNEQLVMDGELYFTLRSALTPSNKRALRDLAKVSVVNREGDGATNV QANWSFVNNHDQEKNRVNQIMLDAYGIKTNTQYGKDGEPKSFEKLYNKEDEAKALAIYNKELASPTKKYSTENVVAQYAFLLS NKNTVPTVYYGDLYQTDASYMSKTTPYYDEITNLLKVRKQYAYGKQHVAYHTSNTSKEAGKDLISSVRFGKDRNTGVATVIGK NAALDTTVQVNMGKTHANQVFVDASGVTNTKLVTDKNGILTVPVKGIKTAEVNGYVGVFVPQATKAPVAAIKAGAVYQGKALD LKTTVTNTTSAVASTRYRVLDTKKATVDSKGRLTGKATGKTTVEATVTLKDGFVLKTVLPIETKANSVTLKATKATLKKNQTT

RIAYTSATDKIKSVQYASANKKVAQVSSRGNVKGIKAGKTTIRVTYTTVGNYKVVKTFTVTVK

SEQ ID NO: 3-[mature amino acid sequence α-GT-E]
FAPSEKLDNRVIFQSFSLYQPYESNMYRTLAKKGELLNSWGVTDVWLPPAYRSFDMARYMEGYAIADRYDLGEFPQGPGGSVA TKYGKATQLEMMVDMLHDDNIKVQMDLVPNQMLGLNKREAVFVRRATSSGEPFMNPFTGGEKTKTLATPYLAYTKGGGMGQEK YGYLKEWNKSFINGTSLQGQGMGRVMTDKDGKPYRYFGKDDANNYLPEWLLDAAKTQNLNVVDTYLAADGWYEVSPENWKPML SQYAKDEGYLEYMKQNGFETKEALLTSTENTKIASLTEEYMKTQAAYGYGSEERSYQNDNSGIDIEDQFLFVDETGFPTQAYN KTMTNNDEFLIGVDLANSNPEVIKEQKNWMKWMLETYKFDGFRIDAASHYDTAILKAEAEISKAHFGKQDYLSYIESYKTEQN AYMKANNNEQLVMDGELYFTLRSALTPSNKRALRDLAKVSVVNREGDGATNVQANWSFVNNHDQEKNRVNQIMLDAYGIKTNT QYGKDGEPKSFEKLYNKEDEAKALAIYNKELASPTKKYSTENVVAQYAFLLSNKNTVPTVYYGDLYQTDASYMSKTTPYYDEI TNLLKVRKQYAYGKQHVAYHTSNTSKEAGKDLISSVRFGKDRNTGVATVIGKNAALDTTVQVNMGKTHANQVFVDASGVTNTK LVTDKNGILTVPVKGIKTAEVNGYVGVFVPQATKAPVAAIKAGAVYQGKALDLKTTVTNTTSAVASTRYRVLDTKKATVDSKG RLTGKATGKTTVEATVTLKDGFVLKTVLPIETKANSVTLKATKATLKKNQTTRIAYTSATDKIKSVQYASANKKVAQVSSRGN

VKGIKAGKTTIRVTYTTVGNYKVVKTFTVTVK

SEQ ID NO: 4-[amino acid sequence of the mature α-glucanotransferase
C-terminally truncated as determined by mass-spec analysis encoded by α-GT-E
AA31-731 [FAPS . . . KAPV] (~79 009 Da)]
FAPSEKLDNRVIFQSFSLYQPYESNMYRTLAKKGELLNSWGVTDVWLPPAYRSFDMARYMEGYAIADRYDLGEFPQGPGGSVA TKYGKATQLEMMVDMLHDDNIKVQMDLVPNQMLGLNKREAVFVRRATSSGEPFMNPFTGGEKTKTLATPYLAYTKGGGMGQEK YGYLKEWNKSFINGTSLQGQGMGRVMTDKDGKPYRYFGKDDANNYLPEWLLDAAKTQNLNVVDTYLAADGWYEVSPENWKPML SQYAKDEGYLEYMKQNGFETKEALLTSTENTKIASLTEEYMKTQAAYGYGSEERSYQNDNSGIDIEDQFLFVDETGFPTQAYN KTMTNNDEFLIGVDLANSNPEVIKEQKNWMKWMLETYKFDGFRIDAASHYDTAILKAEAEISKAHFGKQDYLSYIESYKTEQN AYMKANNNEQLVMDGELYFTLRSALTPSNKRALRDLAKVSVVNREGDGATNVQANWSFVNNHDQEKNRVNQIMLDAYGIKTNT QYGKDGEPKSFEKLYNKEDEAKALAIYNKELASPTKKYSTENVVAQYAFLLSNKNTVPTVYYGDLYQTDASYMSKTTPYYDEI TNLLKVRKQYAYGKQHVAYHTSNTSKEAGKDLISSVRFGKDRNTGVATVIGKNAALDTTVQVNMGKTHANQVFVDASGVTNTK

LVTDKNGILTVPVKGIKTAEVNGYVGVFVPQATKAPV

SEQ ID NO: 5-[synthetic nucleotide sequence of the mature gene encoding α-GT-E]
TTTGCGCTGACACTGATTTTTACAATGGCGTTTTCAAATATGAGCGCTAGCGCATTTGCACCGTCAGAAAAACTGGATAATCG CGTTATTTTTCAGAGCTTTTCACTGTATCAACCGTATGAAAGCAACATGTATAGAACACTGGCAAAAAAGGCGAACTGCTTA ATTCATGGGGAGTTACAGATGTTTGGCTGCCTCCGGCATATAGATCATTTGATATGGCAAGATATATGGAAGGCTATGCGATT GCGGATAGATATGATCTGGGCGAATTTCCGCAAGGCCCTGGCGGATCAGTTGCAACAAAATATGGCAAAGCAACACAGCTGGA AATGATGGTTGATATGCTGCATGATGACAACATCAAAGTCCAAATGGATCTGGTTCCGAATCAAATGCTGGGCCTGAATAAAA GAGAAGCAGTTTTTGTTAGACGCGCAACATCATCAGGCGAACCGTTTATGAATCCGTTTACAGGCGGAGAAAAAACAAAAACA CTGGCAACACCGTATCTGGCGTATACAAAAGGCGGAGGCATGGGCCAAGAAAAATATGGCTATCTGAAAGAATGGAACAAATC ATTTATCAACGGCACATCACTGCAAGGCCAAGGCATGGGCAGAGTTATGACAGATAAAGATGGCAAACCGTATCGCTATTTTG GCAAAGATGATGCGAATAACTATCTGCCGGAATGGCTGCTGGATGCAGCAAAAACACAAAATCTGAATGTCGTCGATACATAT CTGGCAGCAGATGGCTGGTATGAAGTTTCACCGGAAAATTGGAAACCGATGCTGTCACAATATGCAAAGATGAAGGCTACCT GGAATATATGAAACAGAACGGCTTTGAAACAAAAGAAGCACTGCTGACAAGCACGGAAAATACAAAAATCGCGAGCCTGACGG AAGAATACATGAAAACACAAGCAGCGTATGGCTATGGCTCAGAAGAAAGATCATATCAGAATGATAACAGCGGCATCGATATT -continued

```
GAAGATCAGTTTCTGTTTGTTGATGAAACAGGCTTTCCGACACAAGCGTATAACAAAACAATGACGAACAATGATGAATTTCT

GATCGGCGTTGATCTGGCAAATTCAAATCCGGAAGTTATTAAAGAACAGAAAAATTGGATGAAATGGATGCTGGAAACATACA

AATTTGACGGCTTTAGAATTGATGCAGCGAGCCATTATGATACAGCAATTCTGAAAGCAGAAGCGGAAATTAGCAAAGCGCAT

TTTGGCAAACAAGACTATCTGAGCTATATTGAAAGCTATAAAACGGAACAGAATGCGTATATGAAAGCGAACAATAATGAACA

GCTGGTCATGGATGGCGAACTGTATTTTACACTGAGATCAGCACTGACACCGAGCAATAAAAGAGCACTGAGAGATCTGGCAA

AAGTTAGCGTTGTTAATAGAGAAGGTGATGGCGCAACAAATGTTCAAGCAAATTGGAGCTTTGTCAATAATCATGATCAAGAA

AAAAACCGCGTCAATCAGATTATGCTGGATGCGTATGGCATCAAAACAAATACACAGTATGGCAAAGATGGCGAACCGAAATC

ATTTGAAAAACTGTATAACAAAGAAGATGAAGCGAAAGCGCTGGCGATTTACAATAAAGAACTGGCATCACCGACGAAAAAAT

ACAGCACAGAAAATGTTGTTGCGCAGTATGCATTTCTGCTGAGCAATAAAAACACAGTCCCGACAGTTTATTATGGCGATCTG

TATCAGACAGATGCAAGCTATATGTCAAAAACGACGCCGTATTATGACGAAATCACAAATCTGCTGAAAGTCCGCAAACAATA

TGCTTATGGCAAACAACATGTCGCGTATCATACAAGCAACACATCAAAAGAAGCAGGCAAAGACCTGATTAGCTCAGTCAGAT

TTGGAAAAGATAGAAATACAGGCGTTGCAACAGTCATTGGCAAAAATGCAGCACTGGATACAACAGTCCAAGTCAATATGGGC

AAAACACATGCGAATCAAGTTTTTGTCGACGCATCAGGCGTCACAAATACAAAACTGGTCACAGATAAAAACGGCATTCTGAC

AGTTCCGGTCAAAGGCATTAAAACAGCGGAAGTTAATGGCTATGTTGGCGTTTTTGTTCCGCAAGCAACAAAAGCACCGGTTG

CAGCAATT1AAAGCAGGCGCAGTTTATCAAGGCAAAGCACTGGATCTGAAAACAACAGTGACAAATACAACATCAGCAGTTGC

GAGCACAAGATATAGAGTTCTGGATACAAAAAAAGCGACGGTTGATTCAAAAGGCAGACTGACAGGCAAAGCGACAGGCAAAA

CAACAGTTGAAGCAACAGTTACACTGAAAGATGGCTTTGTTCTGAAAACAGTTCTGCCGATCGAAACAAAAGCAAATTCAGTT

ACACTTAAAGCCACAAAAGCGACACTGAAAAAAAACCAGACAACACGCATTGCATATACAAGCGCGACAGATAAAATCAAAAG

CGTTCAATATGCAAGCGCGAACAAAAAAGTTGCACAAGTTTCATCAAGAGGCAACGTCAAAGGCATCAAAGCGGGAAAAACAA

CAATTCGCGTTACATATACAACGGTCGGCAACTATAAAGTCGTCAAAACATTTACAGTCACAGTCAAA
```

SEQ ID NO: 6-[nucleotide sequence of α-GT-S B. Coagulans 2-6]
```
TTGGAAAAGAAATTTTTTAGCAGATTGTCAATATTGATGTTGTCTTTGTTACTGGTTGCCGGCTCGATCAGTTATTTTCCTAA ATCTGCCAAGGCTTATACATCCGGCACATCGCTCGATAACCGCGTGATTTTCCAAAGTTTTAGCCTGTACATGCCATATGAAA GCAATATGTACAAAATTCTTTCAACGAAAGGCAACGAATTGAAAGATTGGGGGATTACGGATATATGGCTTCCGCCGGCTTAC CGTTCTTTCAATGCGGCACGTTACATGGAAGGCTACGCCATTGCCGACCGTTATGACCTCGGTGAATTTAACCAGGGGCCGAA TAACACTCGGCCGACCAAATACGGAACAAGCGATGAATTGAAAAGTATGGTTTCCGTGCTTCACGCAAATGGTTTAAAAGTAC AGGAAGACCTTGTGCCCAACCAGGTTCTCGGATTGAGCAAAAGGGAAGCAGTTTACGTCACACGCGTAGATCAAGACGGAAAT TTGTTTAAAAATCCTTATACAACAGGACTTGCAACGCAAATCAGGGCCAACCTTTATCTCGCTTACACAAAAGGTGGCGGCGA AGGACAGGCAAAATATGGCTATATCAAAGAATGGAACAAAAAATATTTTAACGGTACCTCCTTACAAGGGCAGGGTATGGATC GCGTGATGAAAGACAGCGAGGGCAATCCGTACCGTTATTTTGGGCCAAACAACCCGAAAAACTACTTGCCAAGCTGGCTTGAT GAAGCTGCAGCAGCAAATAAAATCAATACAGTTGATACTTATTTGCCAGTAGACGGCTGGTATGCTGCAAAAGACGCTTCGAC TTCGGATAATTATTGGAAACCGATGTTAATGCATGACCCTGGCTATTTAAAGTACATGAAAAGCCATGGCTATTCATCTGTTG ACGATATACTGAACGGCGACAACGGGCAAATCGCAAGTTTAACAGATGCGTATATTGCATCCCAGCCCGGGTACGGCTTCGGA TCGGAAGAAAGGTCGTTTAAAAATGATGATTCCGGATCAGATGACCAGGATCAATTTTTATTTGTGAAAAAGAATGGGACAAC TGTTCACAACCTTTACAACACGATCAGCGGGCATAACCAGTTTCTGGTAGGAATGGACATAGACAACGGGAATCCAACTGTCC AAAAAGAACAGATCCACTGGATGAACTGGCTACTTGATACGTATCAGTTTGACGGCTTCAGAATTGATGCGGCAGGCCATTAC GATAAGCAAGTGCTGCTGGATGAAGGTGACGTTATGAAACAGCATTTTGGCAGCCATTTAAACGACCATTTAAGCTATATTGA GAGTTATCAAAGTGCCGGGACAGATTTTGAAAATGCAAACGGGAATCCGCAGTTAATGATGGATTATGCCCTGTTCTATTCTT TGCAAAATGCTTTGGGCAAAAATTCGCCATCAAACAGCCTGTCAACCATTGCTACAAACGCTGTTGTCAACAGGGCAAGCGCA GGCACGGCGAATCCAACGCCTAACTGGTCATTTGTGAATAATCATGACCAGGAAAAGAACCGTGTGAATAAAATCATGATGGA CCTGTACGTCATTAAGCCGGGTATACATTACGGCACATCCGCACCGAAATCTTTCCAAGATCTGTATGATAAAAAGACAGAGG
```

-continued

```
CAAAAGCTTTGGATATTTATGAAAAAGACATGGAAAGAACGGTAAAAACATATGCGCCATACAATGTGCCGAGCCAGTACGCA
TATATTTTGACGAATAAAGATACCGTCCCGACTGTCTTTTACGGCGACTTGTACAAAACGAATGCTTCTTACATGAGCGAGCA
TACGCCGTATTATGATACGATTGTGAAATTGTTGAAAGTGCGCAAAAATTATGCCTATGGGAACCAGCAAGTAACCAACTATA
AGTCGAACACTTCCGGCACGGCGGGAAAAGATCTAATCTCAAGCGTCCGCTATGGAAAAGACCGGAATACCGGCGTGGCAACC
GTAATCGGAAATAACCCGAAAACCGATACGACTATTAAAGTGGACATGGGTACCCGGCATGCCAACCAGCTATTTGAGGATGC
AACCGGATTTCATAACGAAAAGCTGTCCACAGATAGCAAAGGCATTTTAACCGTTCATGTAAAAGGGACGCAAAACGCCCAGG
TAAAAGGGTATCTTGGCGTCTGGATCCCCTCAAAAAAAGCGGCAACGCCGAAACAAGGCCCTGCACTTCAATACGGTAAGTAT
GTAACGGTAACAAACAAGCACTATGCCGTATATCAAGACTTCAACTGGAAAAAGAAAAATGTCACTGCAGTGAATAAAACGTA
TCTTGCCAAGGTCCAATACCATCACAGCAACGGATCAACTTACCTGTCCCTTTATGACGGCAAAGGCAAATGGGTAGGCTATA
TCAACGCCAAAGCTGTGAAAACAGGAAGCGGCAAGCAAGGCGCTGCACTTCAATACGGTAAGTATGTAACGGTAACAAACAAG
CACTATGCCGTATATCAAGACTTCAACTGGAAAAAGAAGAATGTCACTGCAGTGAATAAAACGTATCTTGCCAAGGTCCAATA
CCATCACAGCAACGGATCAACTTACCTGTCCCTTTATGATGGCAAAGGAAAATGGGTAGGCTATATCAACGCCAAAGCTGTGA
AAACAGGAAGCGGCAAGCAAGGCGCTGCACTTCAATACGGTAAGTATGTAACGGTAACAAACAAGCACTATGCCGTATATCAA
GACTTTCACTGGAAAAAGAAAAATGTCACTGCCGTGAATAAAACGTATCTTGCCAAGGTCCCAATACCATCACAGCAACGGA
TCAACTTACCTGTCCCTTTATGACGGCAAAGGAAAATGGGTAG
```

SEQ ID NO: 7-[amino acid sequence of α-GT-S]
MEKKFFSRLSILMLSLLLVAGSISYFPKSAKAYTSGTSLDNRVIFQSFSLYMPYESNMYKILSTKGNELKDWGITDIWLPPA YRSFNAARYMEGYAIADRYDLGEFNQGPNNTRPTKYGTSDELKSMVSVLHANGLKVQEDLVPNQVLGLSKREAVYVTRVDQDG NLFKNPYTTGLATQIRANLYLAYTKGGGEGQAKYGYIKEWNKKYFNGTSLQGQGMDRVMKDSEGNPYRYFGPNNPKNYLPSWL DEAAAANKINTVDTYLPVDGWYAAKDASTSDNYWKPMLMHDPGYLKYMKSHGYSSVDDILNGDNGQIASLTDAYIASQPGYGF GSEERSFKNDDSGSDDQDQFLFVKKNGTTVHNLYNTISGHNQFLVGMDIDNGNPTVQKEQIHWMNWLLDTYQFDGFRIDAAGH YDKQVLLDEGDVMKQHFGSHLNDHLSYIESYQSAGTDFENANGNPQLMMDYALFYSLQNALGKNSPSNSLSTIATNAVVNRAS AGTANPTPNWSFVNNHDQEKNRVNKIMMDLYVIKPGIHYGTSAPKSFQDLYDKKTEAKALDIYEKDMERTVKTYAPYNVPSQY AYILTNKDTVPTVFYGDLYKTNASYMSEHTPYYDTIVKLLKVRKNYAYGNQQVTNYKSNTSGTAGKDLISSVRYGKDRNTGVA TVIGNNPKTDTTIKVDMGTRHANQLFEDATGFHNEKLSTDSKGILTVHVKGTQNAQVKGYLGVWIPSKKAATPKQGPALQYGK YVTVTNKHYAVYQDFNWKKKNVTAVNKTYLAKVQYHHSNGSTYLSLYDGKGKWVGYINAKAVKTGSGKQGAALQYGKYVTVTN KHYAVYQDFNWKKKNVTAVNKTYLAKVQYHHSNGSTYLSLYDGKGKWVGYINAKAVKTGSGKQGAALQYGKYVTVTNKHYAVY

QDFHWKKKNVTAVNKNVSCQGPNTITATDQLTCPFMTAKENG

SEQ ID NO: 8-[mature amino acid sequence α-GT-Swith C-terminal truncation used
for expression based on α-GT-E]
YTSGTSLDNRVIFQSFSLYMPYESNMYKILSTKGNELKDWGITDIWLPPAYRSFNAARYMEGYAIADRYDLGEFNQGPNNTRP TKYGTSDELKSMVSVLHANGLKVQEDLVPNQVLGLSKREAVYVTRVDQDGNLFKNPYTTGLATQIRANLYLAYTKGGGEGQAK YGYIKEWNKKYFNGTSLQGQGMDRVMKDSEGNPYRYFGPNNPKNYLPSWLDEAAAANKINTVDTYLPVDGWYAAKDASTSDNY WKPMLMHDPGYLKYMKSHGYSSVDDILNGDNGQIASLTDAYIASQPGYGFGSEERSFKNDDSGSDDQDQFLFVKKNGTTVHNL YNTISGHNQFLVGMDIDNGNPTVQKEQIHWMNWLLDTYQFDGFRIDAAGHYDKQVLLDEGDVMKQHFGSHLNDHLSYIESYQS AGTDFENANGNPQLMMDYALFYSLQNALGKNSPSNSLSTIATNAVVNRASAGTANPTPNWSFVNNHDQEKNRVNKIMMDLYVI KPGIHYGTSAPKSFQDLYDKKTEAKALDIYEKDMERTVKTYAPYNVPSQYAYILTNKDTVPTVFYGDLYKTNASYMSEHTPYY DTIVKLLKVRKNYAYGNQQVTNYKSNTSGTAGKDLISSVRYGKDRNTGVATVIGNNPKTDTTIKVDMGTRHANQLFEDATGFH

NEKLSTDSKGILTVHVKGTQNAQVKGYLGVWIPSKKAATP

SEQ ID NO: 9-[synthetic nucleotide sequence of the mature and 3' deleted gene
encoding α-GT-S for expression]
```
TATACATCAGGCACATCACTGGATAATCGCGTCATTTTTCAGAGCTTTTCACTGTACATGCCGTATGAAAGCAACATGTATAA AATCCTGAGCACAAAAGGCAATGAACTGAAAGATTGGGGCATTACAGATATTTGGCTGCCTCCGGCATATAGATCATTTAATG
```

-continued

```
CAGCAAGATATATGGAAGGCTATGCGATTGCAGATAGATATGATCTGGGCGAATTTAATCAGGGACCGAATAATACACGTCCG
ACAAAATATGGCACAAGCGACGAACTGAAATCAATGGTTAGCGTTCTGCATGCAAATGGCCTGAAAGTTCAAGAAGATCTGGT
TCCGAATCAAGTTCTGGGCCTGTCAAAACGCGAAGCAGTTTATGTTACAAGAGTTGATCAAGACGGCAACCTGTTTAAAAACC
CGTATACAACAGGCCTGGCAACACAAATTAGAGCAAATCTGTATCTGGCGTATACAAAAGGCGGAGGCGAAGGCCAAGCAAAA
TATGGCTATATCAAAGAATGGAACAAAAAATACTTTAATGGCACAAGCCTGCAAGGCCAAGGCATGGATAGAGTTATGAAAGA
TTCAGAAGGCAACCCGTATAGATATTTTGGACCGAATAACCCGAAAAACTATCTGCCGTCATGGCTGGATGAAGCAGCAGCAG
CGAATAAAATCAATACAGTCGATACATATCTGCCGGTTGATGGCTGGTATGCAGCAAAAGATGCATCAACATCAGACAACTAT
TGGAAACCGATGCTGATGCATGATCCGGGATATCTGAAATACATGAAATCACATGGCTATAGCAGCGTCGATGATATTCTGAA
TGGCGATAATGGCCAAATTGCATCACTGACAGATGCATATATTGCATCACAACCGGGATATGGCTTTGGCTCAGAAGAACGCA
GCTTTAAAAACGATGATTCAGGCTCAGATGATCAGGACCAATTTCTGTTTGTCAAAAAAACGGCACAACGGTCCATAACCTG
TATAATACAATTTCAGGCCATAATCAGTTTCTGGTCGGCATGGATATTGATAATGGCAATCCGACAGTCCAGAAAGAACAAAT
TCATTGGATGAATTGGCTGCTGGACACGTATCAATTTGATGGCTTTAGAATTGATGCGGCAGGCCATTATGATAAACAAGTTC
TGCTGGATGAAGGCGACGTTATGAAACAACATTTTGGCTCACATCTGAATGACCATCTGTCATATATCGAAAGCTATCAATCA
GCAGGCACGGATTTTGAAAATGCAAATGGAAATCCGCAGCTGATGATGGATTATGCACTGTTTTATAGCCTGCAAAATGCGCT
GGGCAAAAATTCACCGTCAAATTCACTGTCAACAATTGCAACAAATGCAGTCGTTAATAGAGCAAGCGCAGGCACAGCAAATC
CGACACCGAATTGGTCATTTGTCAATAACCATGATCAAGAAAAAAACCGCGTCAACAAAATCATGATGGACCTGTATGTTATC
AAACCGGGAATCCATTATGGCACATCAGCACCGAAATCATTTCAAGACCTGTACGACAAAAAAACGGAAGCAAAAGCGCTGGA
CATCTACGAAAAGATATGGAAAGAACGGTCAAAACGTATGCACCGTATAATGTTCCGAGCCAGTATGCATATATCCTGACAA
ATAAAGATACAGTCCCGACGGTTTTTTATGGCGATCTGTATAAAACAAACGCGAGCTATATGTCAGAACACACGCCGTATTAT
GACACGATTGTCAAACTGCTGAAAGTCCGCAAAAACTATGCGTATGGCAATCAACAGGTCACAAACTACAAATCAAATACAAG
CGGCACAGCAGGCAAAGATCTGATTTCATCAGTTCGCTATGGCAAAGATAGAAATACAGGCGTTGCAACAGTCATTGGCAATA
ATCCGAAAACGGATACAACGATCAAAGTCGATATGGGCACAAGACATGCAAATCAGCTGTTTGAAGATGCAACAGGCTTTCAT
AATGAAAAACTGAGCACAGATAGCAAAGGCATTCTGACAGTTCATGTTAAAGGCACACAAAATGCACAGGTTAAAGGCTATCT
GGGCGTTTGGATTCCGTCAAAAAAAGCAGCAACACCG
```

DuPont Culture collection α-GT-L

SEQ ID NO: 10-[nucleotide sequence of α-GT-L B. coagluans 2022696]
```
TTGATATTGTCTGTGTTACTGGTTGCCGGTTCGATCAGTTATTTTCCTAAATCTGCCAAGGCTTATACATCCGGTACATCGCT
CGATAACCGCGTAATTTTTCAAAGCTTTAGCCTGTACATGCCATATGAAAGCAATATGTACAAAATTCTTTCAGCGAAAGGCA
GCGAATTGAAAGATTGGGGCATTACGGATATATGGCTCCCTCCGGCTTACCGTTCTTTCAACATGGCGCGTTACATGGAAGGC
TACGCCATTGCCGACCGTTATGACCTCGGTGAATTTAACCAGGGGCCGAATAACACCCGGCCGACCAAATACGGGACAAGCGA
TGAATTGAAAAGTATGGTTTCCGCGCTTCACGCAAGTGGTTTAAAAGTGCAAGAAGATCTTGTACCCAACCAGGTTCTCGGAT
TGGGCAAAAGGGAAGCGGTTTACGTCACACGCGTAGATCAAAACGGAAATTTGTTTAAAAATCCTTATACAACAGGACTTACA
ACGCAAATCAGGGCCGACCTGTACCTCGCTTATACAAAAGGCGGCGGCGAAGGACAGGCAAAATATGGCTACATTAAAGAATG
GAATAAAAGTATTTTAACGGCACCTCCGTACAAGGACAAGGTATGGATCGTGTGATGAAAGACAGCGAGGGCATTCCGTACC
GATATTTTGGGCCAAACAACCCGAAAAACCACTTGCCAAGCTGGCTTAATGAAGCTGCAGCGGCAAATAAAATCAATACAGTT
GATACTTATTGGCAGTAGACGGCTGGTATGCTGCTAAAGACGCTTCGACTTCGGATAATTATTGGAAACCGATGTTAATGAA
CTATGACCCCGGCTATTTAAAGTACATGAAAAGCCATGGCTATTCATCTGTTGACGATATACTGAACGGCGATAATGGACAAA
TCGCAAGTTTAACAGATGCCTATATTGCATCACAACCCTGCTACGGCTTTGGATCGGAAGAAAGATCATTCAAAAATGACAAT
TCCGGATCAGATGACCAGGATCAGTTTCTATTTGTGAAAAAGAATGGGACAACCCTTCACAACCTTAACAACACGATCAGCGG
GCAAAAACAGTTTCTGTTAGGAATGGACATAGACAACGGGAATCCAACTGTCCAAAAAGAACAGATCCACTGGATGAACTGGC
TGCTTGATACGTATCAGTTTGATGGCTTCAGAATTGATGCCGCAAGCCATTATGATAAGCAAGTATTGCTGGATGAAGCCGAC
```

-continued

```
GTCATGAAACAGCATTTTGGCAGCAATTTAAACGACCATTTAAGCTATATTGAGACTTATGAAAGTGCCGGGACAAATTTTGA

AAACGCAAATGGGAATCCGCAGTTAATGATGGATTATGCCCTGTTCTATTCTTTGCAAAATGCTTTGGGCAAAAATTCGCCAT

CAAACAACCTTTCCACCATTGCTACAAACGCTGTTGTAAACAGGGCAGGTGCAGGCACGGCGAACGCAACGCCAAACTGGTCA

TTTGTTAATAATCATGACCAGGAAAAGAATCGTGTGAACCGTATCATGCTGGACCAGTACGGCATTAAGCCGGGGACGCATTA

CGGCACATCCACACCGAAGGCTTTCCAGGATCTGTATGATAAAAAGACAGAGGCAAAAGCTTTGGACATCTATGAAAGAGACA

TGGAAAGCACGGTAAAAAAATATGCGCCATCCAATGTGCCAAGCCAGTACGCATATGTTTTGACGAATAAAGACACCGTCCCG

ACTGTCTTTTATGGCGACTTGTACAAAACGAATGCATCCTACATGAGTGAACGTACGCCGTATTACGATACGATTGTGAAATT

GCTGAAAGTGCGCAAAAACTATGCCTACGGGAACCAGCAAGTAACTAACTATAAGTCGAATACTTCCAGCACGGCGGGAAAAG

ATTTGATCTCAAGCGTCCGCTATGGAAATGACCGGAATACCGGCGTGGCAACCGTAATCGGAAATAACCCGAAAACCGATACG

ACTATTAAAGTGAATATGGGATCCCGGCATGCCAACCAGCTATTTGAGGATGCAACCGGATTCCATAACGAAAAGCTGGTCAC

AGATAGCAAAGGCGTTTTAACCGTTCATGTAAAAGGGACACAAAATGCCCGGGTAAAAGGGTACCTTGGCGTCTGGATCCCGG

CAAAAAAAGCGGCAACGCCAAAACAAGGCCCTGCACTTAAATACGGTAAGTATGTAACGATAACAAACAAGCACTATGCCGTA

TATCAAGACTTCAACTGGAAGAAGAAGAATGTCAATGCAGTGAATAAAACGTATCTTGCCAAGGTCCAATACCATCACAGCAA

CGGATCAACTTATCTGTCCCTTTATGATGGCAAAGGAAAATGGGCTGGCTATATCAATGCCAAGGCAGCGAAAACCGGAAGCG

GCAAGCAAGGTGCTGCCATTCAATACGGCAAATCCGTCAAAGTAACCAGCAAGAACTACGCCGTATATCAAAACTTTAACTGG

AAGAAGAAAAATATCCGGGCCGTAAACAAAACATATTTGGCGAAGTACATTTATTATCATATAAATGGGCTAAGCTACCTGTC

CCTTTATGATAACAAGGGCAAATGGATAGGCTACATCAATGCCAAAGCAGTTAAAAGCAAATAA
```

SEQ ID NO: 11-[amino acid sequence of α-GT-L]

LILSVLLVAGSISYFPKSAKAYTSGTSLDNRVIFQSFSLYMPYESNMYKILSAKGSELKDWGITDIWLPPAYRSFNMARYMEG
YAIADRYDLGEFNQGPNNTRPTKYGTSDELKSMVSALHASGLKVQEDLVPNQVLGLGKREAVYVTRVDQNGNLFKNPYTTGLT
TQIRADLYAYTKGGGEGQAKYGYIKEWNKKYFNGTSVQGQGMDRVMKDSEGIPYRYFGPNNPKNHLPSWLNEAAAANKINTV
DTYLAVDGWYAAKDASTSDNYWKPMLMNYDPGYLKYMKSHGYSSVDDILNGDNGQIASLTDAYIASQPCYGFGSEERSFKNDN
SGSDDQDQFLFVKKNGTTLHNLNNTISGQKQFLLGMDIDNGNPTVQKEQIHWMNWLLDTYQFDGFRIDAASHYDKQVLLDEAD
VMKQHFGSNLNDHLSYIETYESAGTNFENANGNPQLMMDYALFYSLQNALGKNSPSNNLSTIATNAVVNRAGAGTANATPNWS
FVNNHDQEKNRVNRIMLDQYGIKPGTHYGTSTPKAFQDLYDKKTEAKALDIYERDMESTVKKYAPSNVPSQYAYVLTNKDTVP
TVFYGDLYKTNASYMSERTPYYDTIVKLLKVRKNYAYGNQQVTNYKSNTSSTAGKDLISSVRYGNDRNTGVATVIGNNPKTDT
TIKVNMGSRHANQLFEDATGFHNEKLVTDSKGVLTVHVKGTQNARVKGYLGVWIPAKKAATPKQGPALKYGKYVTITNKHYAV
YQDFNWKKKNVNAVNKTYLAKVQYHHSNGSTYLSLYDGKGKWAGYINAKAAKTGSGKQGAAIQYGKSVKVTSKNYAVYQNFNW
KKKNIRAVNKTYLAKYIYYHINGLSYLSLYDNKGKWIGYINAKAVKSKLILSVLLVAGSISYFPKSAKAYTSGTSLDNRVIFQ
SFSLYMPYESNMYKILSAKGSELKDWGITDIWLPPAYRSFNMARYMEGYAIADRYDLGEFNQGPNNTRPTKYGTSDELKSMVS
ALHASGLKVQEDLVPNQVLGLGKREAVYVTRVDQNGNLFKNPYTTGLTTQIRADLYAYTKGGGEGQAKYGYIKEWNKKYFNG
TSVQGQGMDRVMKDSEGIPYRYFGPNNPKNHLPSWLNEAAAANKINTVDTYLAVDGWYAAKDASTSDNYWKPMLMNYDPGYLK
YMKSHGYSSVDDILNGDNGQIASLTDAYIASQPCYGFGSEERSFKNDNSGSDDQDQFLFVKKNGTTLHNLNNTISGQKQFLLG
MDIDNGNPTVQKEQIHWMNWLLDTYQFDGFRIDAASHYDKQVLLDEADVMKQHFGSNLNDHLSYIETYESAGTNFENANGNPQ
LMMDYALFYSLQNALGKNSPSNNLSTIATNAVVNRAGAGTANATPNWSFVNNHDQEKNRVNRIMLDQYGIKPGTHYGTSTPKA
FQDLYDKKTEAKALDIYERDMESTVKKYAPSNVPSQYAYVLTNKDTVPTVFYGDLYKTNASYMSERTPYYDTIVKLLKVRKNY
AYGNQQVTNYKSNTSSTAGKDLISSVRYGNDRNTGVATVIGNNPKTDTTIKVNMGSRHANQLFEDATGFHNEKLVTDSKGVLT
VHVKGTQNARVKGYLGVWIPAKKAATPKQGPALKYGKYVTITNKHYAVYQDFNWKKKNVNAVNKTYLAKVQYHHSNGSTYLSL
YDGKGKWAGYINAKAAKTGSGKQGAAIQYGKSVKVTSKNYAVYQNFNWKKKNIRAVNKTYLAKYIYYHINGLSYLSLYDNKGK
WIGYINAKAVKSK

SEQ ID NO: 12-[mature amino acid sequence α-GT-L with C-terminal truncation used for expression based on α-GT-E]
YTSGTSLDNRVIFQSFSLYMPYESNMYKILSAKGSELKDWGITDIWLPPAYRSFNMARYMEGYAIADRYDLGEFNQGPNNTRP TKYGTSDELKSMVSALHASGLKVQEDLVPNQVLGLGKREAVYVTRVDQNGNLFKNPYTTGLTTQIRADLYLAYTKGGGEGQAK YGYIKEWNKKYFNGTSVQGQGMDRVMKDSEGIPYRYFGPNNPKNHLPSWLNEAAAANKINTVDTYLAVDGWYAAKDASTSDNY WKPMLMNYDPGYLKYMKSHGYSSVDDILNGDNGQIASLTDAYIASQPCYGFGSEERSFKNDNSGSDDQDQFLFVKKNGTTLHN LNNTISGQKQFLLGMDIDNGNPTVQKEQIHWMNWLLDTYQFDGFRIDAASHYDKQVLLDEADVMKQHFGSNLNDHLSYIETYE SAGTNFENANGNPQLMMDYALFYSLQNALGKNSPSNNLSTIATNAVVNRAGAGTANATPNWSFVNNHDQEKNRVNRIMLDQYG IKPGTHYGTSTPKAFQDLYDKKTEAKALDIYERDMESTVKKYAPSNVPSQYAYVLTNKDTVPTVFYGDLYKTNASYMSERTPY YDTIVKLLKVRKNYAYGNQQVTNYKSNTSSTAGKDLISSVRYGNDRNTGVATVIGNNPKTDTTIKVNMGSRHANQLFEDATGF

HNEKLVTDSKGVLTVHVKGTQNARVKGYLGVWIPAKKAATP

SEQ ID NO: 13-[synthetic nucleotide sequence of the mature and 3' deleted gene encoding α-GT-L for expression]
TATACATCAGGCACATCACTGGATAATCGCGTCATTTTTCAGAGCTTTTCACTGTACATGCCGTATGAAAGCAACATGTATAA AATCCTGTCAGCGAAAGGCAGCGAACTGAAAGATTGGGGCATTACAGATATTTGGCTGCCTCCGGCATATCGCAGCTTTAATA TGGCAAGATATATGGAAGGCTATGCAATTGCAGATAGATATGATCTGGGCGAATTTAATCAGGGACCGAATAATACACGTCCG ACAAAATATGGCACAAGCGACGAACTGAAATCAATGGTTTCAGCACTGCATGCATCAGGCCTGAAAGTTCAAGAAGATCTGGT TCCGAATCAAGTTCTGGGCCTGGGCAAACGCGAAGCAGTTTATGTTACAAGAGTTGATCAGAACGGCAACCTGTTTAAAAACC CGTATACAACAGGCCTGACAACACAAATTAGAGCAGATCTGTATCTGGCGTATACAAAAGGCGGAGGCGAAGGCCAAGCAAAA TATGGCTATATCAAAGAATGGAACAAAAAATACTTTAACGGCACAAGCGTTCAAGGCCAAGGCATGGATAGAGTTATGAAAGA TTCAGAAGGCATCCCGTATAGATATTTTGGACCGAATAACCCGAAAAATCATCTGCCGTCATGGCTGAATGAAGCAGCAGCAG CGAATAAAATCAATACGGTTGATACATATCTGGCAGTCGATGGCTGGTATGCAGCAAAAGATGCATCAACATCAGACAACTAT TGGAAACCGATGCTGATGAATTATGATCCGGGATACCTGAAATATATGAAAAGCCATGGCTATAGCAGCGTCGATGATATTCT GAATGGCGATAATGGCCAAATTGCATCACTGACAGATGCATATATTGCATCACAACCGTGCTATGGCTTTGGCTCAGAAGAAC GCAGCTTTAAAAACGATAATAGCGGCAGCGACGATCAAGATCAATTTCTGTTTGTCAAAAAAAACGGCACGACACTGCATAAC CTGAACAATACAATTTCAGGCCAGAAACAATTTCTGCTGGGCATGGATATTGATAATGGCAATCCGACAGTCCAGAAAGAACA AATTCATTGGATGAATTGGCTGCTGGACACGTATCAATTTGATGGCTTTAGAATTGATGCAGCGAGCCATTATGATAAACAAG TCCTGCTGGATGAAGCGGATGTTATGAAACAACATTTTGGCAGCAATCTGAACGACCATCTGAGCTATATTGAAACGTATGAA TCAGCAGGCACAAACTTTGAAAATGCGAATGGAAATCCGCAGCTGATGATGGATTATGCACTGTTTTATAGCCTGCAAAATGC GCTGGGCAAAAATTCACCGTCAAATAATCTGAGCACAATTGCAACAAATGCAGTTGTTAATAGAGCAGGCGCAGGCACAGCAA ATGCAACACCGAATTGGTCATTTGTCAACAACCATGATCAAGAAAAAAATCGCGTCAACCGCATTATGCTGGATCAGTATGGC ATTAAACCGGGAACACATTATGGCACATCAACACCGAAAGCATTTCAAGACCTGTACGACAAAAAAACAGAAGCAAAAGCGCT GGATATCTATGAAAGAGATATGGAAAGCACAGTCAAAAAATACGCACCGTCAAATGTTCCGAGCCAATATGCGTATGTCCTGA CAAATAAAGATACAGTCCCGACAGTTTTTTATGGCGACCTGTATAAAACAAACGCGAGCTATATGTCAGAACGCACACCGTAT TATGATACGATTGTCAAACTGCTGAAAGTCCGCAAAAACTATGCGTATGGCAATCAACAGGTCACAAACTACAAAAGCAATAC ATCATCAACGGCAGGCAAAGATCTGATTTCATCAGTTAGATATGGCAACGATAGAAATACAGGCGTTGCAACAGTTATTGGCA ATAATCCGAAAACGGATACGACGATCAAAGTTAATATGGGCTCAAGACATGCGAACCAGCTGTTTGAAGATGCAACAGGCTTT CATAATGAAAAACTGGTCACAGATTCAAAAGGCGTTCTGACAGTTCATGTTAAAGGCACACAAAATGCACGCGTTAAAGGCTA

TCTGGGCGTTTGGATTCCGGCAAAAAAAGCAGCAACACCG

What is claimed is:

1. A composition comprising at least: (i) an isolated GH70 subfamily 4 α-glucanotransferase comprising an amino acid sequence that is at least 95% identical to amino acids 31-731 of SEQ ID NO:2, and (ii) a glucooligosaccharide with α-(1→4) and α-(1→6) glycosidic linkages.

2. The composition of claim 1, wherein the α-glucanotransferase comprises an amino acid sequence that is at least 98% identical to amino acids 31-731 of SEQ ID NO:2.

3. The composition of claim 1, wherein the α-glucanotransferase comprises an amino acid sequence that is at least 99% identical to amino acids 31-731 of SEQ ID NO:2.

4. The composition of claim 1, wherein the α-glucanotransferase comprises an amino acid sequence that is at least 99.5% identical to amino acids 31-731 of SEQ ID NO:2.

5. The composition of claim 1, wherein the α-glucanotransferase comprises amino acids 31-731 of SEQ ID NO:2.

6. The composition of claim 1, wherein the composition is in a lyophilized powder form, an encapsulated form, a coated form, a granulated form, or a liquid formulation.

7. The composition of claim 1, further comprising a diluent.

8. A method of producing saccharide products, said method comprising contacting the α-glucanotransferase according to claim 1 with a substrate comprising a maltooligosaccharide or maltodextrin under conditions of pH 3-10 and 30-70° C. to produce at least one glucooligosaccharide with α-(1→4) and α-(1→6) glycosidic linkages.

9. The method of claim 8, wherein the substrate comprises malto-tetraose, malto-pentaose, malto-hexaose, or malto-heptaose.

10. The method of claim 8, wherein the substrate is comprised in a beverage or food, wherein said glucooligosaccharide with α-(1→4) and α-(1→6) glycosidic linkages is produced in the beverage or food in situ.

11. The method of claim 10, wherein the substrate is comprised in said beverage.

12. The method of claim 10, wherein the substrate is comprised in said food.

* * * * *

SEQUENCE LISTING

<160> NUMBER OF SEQ ID NOS: 63

<210> SEQ ID NO 1
<211> LENGTH: 2676
<212> TYPE: DNA
<213> ORGANISM: Exiguobacterium acetylicum
<220> FEATURE:
<221> NAME/KEY: misc_feature
<223> OTHER INFORMATION: alpha-GT-E

<400> SEQUENCE: 1

| | | | | | |
|---|---|---|---|---|---|
| atgaacaagg | cgaaaaaagt | ctcaacaggt | ttgcttgcgg | cattggtagc | gacaagcgga | 60 |
| ctgacgtatg | caccagaaag | cgcaaaggct | ttcgcaccaa | gtgaaaaact | cgataaccgc | 120 |
| gttattttcc | aaagcttcag | cctgtatcaa | ccatacgaaa | gcaacatgta | ccggacgctt | 180 |
| gctaaaaaag | gtgagttgct | caattcgtgg | ggtgtgacag | atgtgtggtt | accacctgca | 240 |
| tatcgttcat | tcgatatggc | acgttacatg | gaaggatatg | caatcgctga | ccgttatgac | 300 |
| cttggtgaat | tcccacaagg | accaggtgga | tcggttgcga | cgaaatacgg | aaaagccaca | 360 |
| caactcgaga | tgatggtcga | catgttgcat | gacgacaaca | tcaaagtcca | gatggacctc | 420 |
| gttccaaacc | aaatgctcgg | tctcaacaaa | cgtgaagctg | tcttcgttcg | tcgtgcgaca | 480 |
| agttcaggtg | agccgttcat | gaacccattc | acaggtggag | aaaaaacgaa | gacccctcgca | 540 |
| acgccttacc | tcgcttacac | aaaaggtggc | ggtatgggac | aagagaagta | cggttacctc | 600 |
| aaagagtgga | acaaatcatt | catcaatgga | acatcactgc | aagggcaggg | tatgggcgc | 660 |
| gtcatgacgg | acaaagacgg | taaaccgtac | cgttacttcg | gtaaagacga | tgcgaacaac | 720 |
| tacttaccag | aatggttgct | tgacgcagcg | aagacacaga | acttgaatgt | cgtcgatacg | 780 |
| tacctcgcag | cagacggttg | gtatgaagtc | tcaccagaga | actggaagcc | gatgctttcg | 840 |
| caatatgcga | aggatgaagg | atacctcgag | tacatgaaac | aaaacggctt | cgaaacaaaa | 900 |
| gaagctttgc | ttacttcaac | ggaaaacacc | aagatcgctt | cgttgacgga | agaatacatg | 960 |
| aagacacaag | ctgcgtacgg | ttatgggtca | gaagaacgtt | cataccaaaa | cgataactca | 1020 |
| ggaatcgata | tcgaagatca | gttcctcttc | gttgatgaga | ctggtttccc | aacacaggca | 1080 |
| tacaacaaaa | cgatgacgaa | caacgatgag | ttcttgatcg | gtgtcgacct | tgcgaactcg | 1140 |
| aacccagaag | tcatcaagga | acaaaagaac | tggatgaagt | ggatgcttga | aacgtacaag | 1200 |
| ttcgacggtt | tccggattga | tgctgcgtcg | cactacgata | cggcgatcct | caaagcagaa | 1260 |
| gcggaaattt | caaaagcaca | cttcgggaaa | caagattacc | tcagctatat | cgagagctat | 1320 |
| aaaacagaac | agaatgctta | catgaaagca | aacaataacg | agcaactcgt | catggacgga | 1380 |
| gagctttact | tcacgctccg | ttcagcactc | acaccatcga | caaacgtgc | actccgtgac | 1440 |
| ttagcgaaag | tctcagtcgt | taaccgtgaa | ggtgacggcg | cgacaaacgt | tcaagcgaac | 1500 |
| tggtcattcg | tcaacaacca | tgaccaagag | aaaaaccgcg | tcaaccaaat | catgcttgat | 1560 |
| gcgtacggca | tcaaaacgaa | tacgcagtac | ggaaaagacg | gcgagccgaa | atcgttcgag | 1620 |
| aagctctaca | ataaagaaga | tgaagcgaag | gcacttgcga | tctacaacaa | agaactcgca | 1680 |
| agtccaacga | agaaatactc | gacggaaaac | gtcgtcgcgc | aatacgcgtt | ccttctttcg | 1740 |
| aacaaaaaca | cggtgccaac | ggtctactac | ggtgatctct | accagacgga | tgcatcgtac | 1800 |
| atgtcgaaaa | cgacaccgta | ctatgatgaa | atcacgaatc | tcctaaaagt | ccgtaaacag | 1860 |
| tatgcgtatg | gtaaacaaca | cgttgcgtac | cacacatcga | acacgtcaaa | agaagcgggt | 1920 |
| aaagacttga | tctcaagcgt | ccgtttcgga | aaagaccgca | acacaggtgt | cgcgacagtc | 1980 |

-continued

```
atcgggaaaa acgcagcgct tgatacgacg gttcaagtca acatgggtaa aacacacgcg    2040
aaccaagtct tcgttgatgc tagtggcgtt acgaacacga aactcgtcac agataagaac    2100
ggtatcttga cggttccagt caaaggtatc aaaacagcag aagtcaacgg ttacgtcggc    2160
gtcttcgttc cacaagcaac aaaagcgcca gttgcagcaa tcaaagcagg tgctgtctac    2220
caaggaaaag cactcgactt gaaaacgaca gttacgaaca cgacatcagc agttgcgtca    2280
acacgctacc gtgtccttga tacgaaaaaa gcgacagttg attcaaaagg tcgtctgaca    2340
ggtaaagcaa caggtaagac gacggttgaa gcaacagtta cgttaaaaga cggttttgtc    2400
ttgaaaacag ttttaccgat cgaaacaaaa gcgaacagcg tcacgctgaa agcaacaaaa    2460
gcaacactca agaagaacca gacgacacgt atcgcgtata cgtcagcaac ggataagatc    2520
aaatctgttc agtatgcgtc agcgaacaaa aaagtcgcgc aagtctcgtc acgtggtaac    2580
gtgaaaggga tcaaagcagg caaaacgacg atccgtgtca catacacgac agtaggaaac    2640
tacaaagtcg tcaaaacgtt cacagtcaca gtcaag                              2676
```

<210> SEQ ID NO 2
<211> LENGTH: 892
<212> TYPE: PRT
<213> ORGANISM: Exiguobacterium acetylicum
<220> FEATURE:
<221> NAME/KEY: misc_feature
<223> OTHER INFORMATION: alpha-GT-E

<400> SEQUENCE: 2

```
Met Asn Lys Ala Lys Lys Val Ser Thr Gly Leu Leu Ala Ala Leu Val
1               5                   10                  15

Ala Thr Ser Gly Leu Thr Tyr Ala Pro Glu Ser Ala Lys Ala Phe Ala
                20                  25                  30

Pro Ser Glu Lys Leu Asp Asn Arg Val Ile Phe Gln Ser Phe Ser Leu
            35                  40                  45

Tyr Gln Pro Tyr Glu Ser Asn Met Tyr Arg Thr Leu Ala Lys Lys Gly
        50                  55                  60

Glu Leu Leu Asn Ser Trp Gly Val Thr Asp Val Trp Leu Pro Pro Ala
65                  70                  75                  80

Tyr Arg Ser Phe Asp Met Ala Arg Tyr Met Glu Gly Tyr Ala Ile Ala
                85                  90                  95

Asp Arg Tyr Asp Leu Gly Glu Phe Pro Gln Gly Pro Gly Gly Ser Val
            100                 105                 110

Ala Thr Lys Tyr Gly Lys Ala Thr Gln Leu Glu Met Met Val Asp Met
        115                 120                 125

Leu His Asp Asp Asn Ile Lys Val Gln Met Asp Leu Val Pro Asn Gln
    130                 135                 140

Met Leu Gly Leu Asn Lys Arg Glu Ala Val Phe Val Arg Arg Ala Thr
145                 150                 155                 160

Ser Ser Gly Glu Pro Phe Met Asn Pro Phe Thr Gly Gly Glu Lys Thr
                165                 170                 175

Lys Thr Leu Ala Thr Pro Tyr Leu Ala Tyr Thr Lys Gly Gly Gly Met
            180                 185                 190

Gly Gln Glu Lys Tyr Gly Tyr Leu Lys Glu Trp Asn Lys Ser Phe Ile
        195                 200                 205

Asn Gly Thr Ser Leu Gln Gly Gln Gly Met Gly Arg Val Met Thr Asp
    210                 215                 220

Lys Asp Gly Lys Pro Tyr Arg Tyr Phe Gly Lys Asp Asp Ala Asn Asn
225                 230                 235                 240
```

-continued

```
Tyr Leu Pro Glu Trp Leu Leu Asp Ala Ala Lys Thr Gln Asn Leu Asn
            245                 250                 255
Val Val Asp Thr Tyr Leu Ala Ala Asp Gly Trp Tyr Glu Val Ser Pro
            260                 265                 270
Glu Asn Trp Lys Pro Met Leu Ser Gln Tyr Ala Lys Asp Glu Gly Tyr
            275                 280                 285
Leu Glu Tyr Met Lys Gln Asn Gly Phe Glu Thr Lys Glu Ala Leu Leu
            290                 295                 300
Thr Ser Thr Glu Asn Thr Lys Ile Ala Ser Leu Thr Glu Glu Tyr Met
305                 310                 315                 320
Lys Thr Gln Ala Ala Tyr Gly Tyr Gly Ser Glu Glu Arg Ser Tyr Gln
            325                 330                 335
Asn Asp Asn Ser Gly Ile Asp Ile Glu Asp Gln Phe Leu Phe Val Asp
            340                 345                 350
Glu Thr Gly Phe Pro Thr Gln Ala Tyr Asn Lys Thr Met Thr Asn Asn
            355                 360                 365
Asp Glu Phe Leu Ile Gly Val Asp Leu Ala Asn Ser Asn Pro Glu Val
            370                 375                 380
Ile Lys Glu Gln Lys Asn Trp Met Lys Trp Met Leu Glu Thr Tyr Lys
385                 390                 395                 400
Phe Asp Gly Phe Arg Ile Asp Ala Ala Ser His Tyr Asp Thr Ala Ile
            405                 410                 415
Leu Lys Ala Glu Ala Glu Ile Ser Lys Ala His Phe Gly Lys Gln Asp
            420                 425                 430
Tyr Leu Ser Tyr Ile Glu Ser Tyr Lys Thr Glu Gln Asn Ala Tyr Met
            435                 440                 445
Lys Ala Asn Asn Asn Glu Gln Leu Val Met Asp Gly Glu Leu Tyr Phe
            450                 455                 460
Thr Leu Arg Ser Ala Leu Thr Pro Ser Asn Lys Arg Ala Leu Arg Asp
465                 470                 475                 480
Leu Ala Lys Val Ser Val Val Asn Arg Glu Gly Asp Gly Ala Thr Asn
            485                 490                 495
Val Gln Ala Asn Trp Ser Phe Val Asn Asn His Asp Gln Glu Lys Asn
            500                 505                 510
Arg Val Asn Gln Ile Met Leu Asp Ala Tyr Gly Ile Lys Thr Asn Thr
            515                 520                 525
Gln Tyr Gly Lys Asp Gly Glu Pro Lys Ser Phe Glu Lys Leu Tyr Asn
            530                 535                 540
Lys Glu Asp Glu Ala Lys Ala Leu Ala Ile Tyr Asn Lys Glu Leu Ala
545                 550                 555                 560
Ser Pro Thr Lys Lys Tyr Ser Thr Glu Asn Val Val Ala Gln Tyr Ala
            565                 570                 575
Phe Leu Leu Ser Asn Lys Asn Thr Val Pro Thr Val Tyr Tyr Gly Asp
            580                 585                 590
Leu Tyr Gln Thr Asp Ala Ser Tyr Met Ser Lys Thr Thr Pro Tyr Tyr
            595                 600                 605
Asp Glu Ile Thr Asn Leu Leu Lys Val Arg Lys Gln Tyr Ala Tyr Gly
            610                 615                 620
Lys Gln His Val Ala Tyr His Thr Ser Asn Thr Ser Lys Glu Ala Gly
625                 630                 635                 640
Lys Asp Leu Ile Ser Ser Val Arg Phe Gly Lys Asp Arg Asn Thr Gly
            645                 650                 655
```

-continued

```
Val Ala Thr Val Ile Gly Lys Asn Ala Ala Leu Asp Thr Thr Val Gln
            660                 665                 670

Val Asn Met Gly Lys Thr His Ala Asn Gln Val Phe Val Asp Ala Ser
        675                 680                 685

Gly Val Thr Asn Thr Lys Leu Val Thr Asp Lys Asn Gly Ile Leu Thr
    690                 695                 700

Val Pro Val Lys Gly Ile Lys Thr Ala Glu Val Asn Gly Tyr Val Gly
705                 710                 715                 720

Val Phe Val Pro Gln Ala Thr Lys Ala Pro Val Ala Ile Lys Ala
            725                 730                 735

Gly Ala Val Tyr Gln Gly Lys Ala Leu Asp Leu Lys Thr Thr Val Thr
        740                 745                 750

Asn Thr Thr Ser Ala Val Ala Ser Thr Arg Tyr Arg Val Leu Asp Thr
    755                 760                 765

Lys Lys Ala Thr Val Asp Ser Lys Gly Arg Leu Thr Gly Lys Ala Thr
        770                 775                 780

Gly Lys Thr Thr Val Glu Ala Thr Val Thr Leu Lys Asp Gly Phe Val
785                 790                 795                 800

Leu Lys Thr Val Leu Pro Ile Glu Thr Lys Ala Asn Ser Val Thr Leu
            805                 810                 815

Lys Ala Thr Lys Ala Thr Leu Lys Lys Asn Gln Thr Thr Arg Ile Ala
        820                 825                 830

Tyr Thr Ser Ala Thr Asp Lys Ile Lys Ser Val Gln Tyr Ala Ser Ala
    835                 840                 845

Asn Lys Lys Val Ala Gln Val Ser Ser Arg Gly Asn Val Lys Gly Ile
850                 855                 860

Lys Ala Gly Lys Thr Thr Ile Arg Val Thr Tyr Thr Thr Val Gly Asn
865                 870                 875                 880

Tyr Lys Val Val Lys Thr Phe Thr Val Thr Val Lys
            885                 890
```

<210> SEQ ID NO 3
<211> LENGTH: 862
<212> TYPE: PRT
<213> ORGANISM: Exiguobacterium acetylicum
<220> FEATURE:
<221> NAME/KEY: misc_feature
<223> OTHER INFORMATION: mature alpha-glucanotransferase encoded by
    alpha-GT-E

<400> SEQUENCE: 3

```
Phe Ala Pro Ser Glu Lys Leu Asp Asn Arg Val Ile Phe Gln Ser Phe
1               5                   10                  15

Ser Leu Tyr Gln Pro Tyr Glu Ser Asn Met Tyr Arg Thr Leu Ala Lys
            20                  25                  30

Lys Gly Glu Leu Leu Asn Ser Trp Gly Val Thr Asp Val Trp Leu Pro
        35                  40                  45

Pro Ala Tyr Arg Ser Phe Asp Met Ala Arg Tyr Met Glu Gly Tyr Ala
    50                  55                  60

Ile Ala Asp Arg Tyr Asp Leu Gly Glu Phe Pro Gln Gly Pro Gly Gly
65                  70                  75                  80

Ser Val Ala Thr Lys Tyr Gly Lys Ala Thr Gln Leu Glu Met Met Val
            85                  90                  95

Asp Met Leu His Asp Asn Ile Lys Val Gln Met Asp Leu Val Pro
        100                 105                 110

Asn Gln Met Leu Gly Leu Asn Lys Arg Glu Ala Val Phe Val Arg Arg
```

```
            115                 120                 125
Ala Thr Ser Ser Gly Glu Pro Phe Met Asn Pro Phe Thr Gly Gly Glu
            130                 135                 140

Lys Thr Lys Thr Leu Ala Thr Pro Tyr Leu Ala Tyr Thr Lys Gly Gly
145                 150                 155                 160

Gly Met Gly Gln Glu Lys Tyr Gly Tyr Leu Lys Glu Trp Asn Lys Ser
                165                 170                 175

Phe Ile Asn Gly Thr Ser Leu Gln Gly Gln Gly Met Gly Arg Val Met
            180                 185                 190

Thr Asp Lys Asp Gly Lys Pro Tyr Arg Tyr Phe Gly Lys Asp Asp Ala
            195                 200                 205

Asn Asn Tyr Leu Pro Glu Trp Leu Leu Asp Ala Ala Lys Thr Gln Asn
210                 215                 220

Leu Asn Val Val Asp Thr Tyr Leu Ala Ala Asp Gly Trp Tyr Glu Val
225                 230                 235                 240

Ser Pro Glu Asn Trp Lys Pro Met Leu Ser Gln Tyr Ala Lys Asp Glu
                245                 250                 255

Gly Tyr Leu Glu Tyr Met Lys Gln Asn Gly Phe Glu Thr Lys Glu Ala
            260                 265                 270

Leu Leu Thr Ser Thr Glu Asn Thr Lys Ile Ala Ser Leu Thr Glu Glu
            275                 280                 285

Tyr Met Lys Thr Gln Ala Ala Tyr Gly Tyr Gly Ser Glu Glu Arg Ser
            290                 295                 300

Tyr Gln Asn Asp Asn Ser Gly Ile Asp Ile Glu Asp Gln Phe Leu Phe
305                 310                 315                 320

Val Asp Glu Thr Gly Phe Pro Thr Gln Ala Tyr Asn Lys Thr Met Thr
                325                 330                 335

Asn Asn Asp Glu Phe Leu Ile Gly Val Asp Leu Ala Asn Ser Asn Pro
            340                 345                 350

Glu Val Ile Lys Glu Gln Lys Asn Trp Met Lys Trp Met Leu Glu Thr
            355                 360                 365

Tyr Lys Phe Asp Gly Phe Arg Ile Asp Ala Ala Ser His Tyr Asp Thr
            370                 375                 380

Ala Ile Leu Lys Ala Glu Ala Glu Ile Ser Lys Ala His Phe Gly Lys
385                 390                 395                 400

Gln Asp Tyr Leu Ser Tyr Ile Glu Ser Tyr Lys Thr Glu Gln Asn Ala
                405                 410                 415

Tyr Met Lys Ala Asn Asn Asn Glu Gln Leu Val Met Asp Gly Glu Leu
            420                 425                 430

Tyr Phe Thr Leu Arg Ser Ala Leu Thr Pro Ser Asn Lys Arg Ala Leu
            435                 440                 445

Arg Asp Leu Ala Lys Val Ser Val Val Asn Arg Glu Gly Asp Gly Ala
450                 455                 460

Thr Asn Val Gln Ala Asn Trp Ser Phe Val Asn Asn His Asp Gln Glu
465                 470                 475                 480

Lys Asn Arg Val Asn Gln Ile Met Leu Asp Ala Tyr Gly Ile Lys Thr
                485                 490                 495

Asn Thr Gln Tyr Gly Lys Asp Gly Glu Pro Lys Ser Phe Glu Lys Leu
            500                 505                 510

Tyr Asn Lys Glu Asp Glu Ala Lys Ala Leu Ala Ile Tyr Asn Lys Glu
            515                 520                 525

Leu Ala Ser Pro Thr Lys Lys Tyr Ser Thr Glu Asn Val Val Ala Gln
            530                 535                 540
```

Tyr Ala Phe Leu Leu Ser Asn Lys Asn Thr Val Pro Thr Val Tyr Tyr
545                 550                 555                 560

Gly Asp Leu Tyr Gln Thr Asp Ala Ser Tyr Met Ser Lys Thr Thr Pro
            565                 570                 575

Tyr Tyr Asp Glu Ile Thr Asn Leu Leu Lys Val Arg Lys Gln Tyr Ala
        580                 585                 590

Tyr Gly Lys Gln His Val Ala Tyr His Thr Ser Asn Thr Ser Lys Glu
    595                 600                 605

Ala Gly Lys Asp Leu Ile Ser Ser Val Arg Phe Gly Lys Asp Arg Asn
610                 615                 620

Thr Gly Val Ala Thr Val Ile Gly Lys Asn Ala Ala Leu Asp Thr Thr
625                 630                 635                 640

Val Gln Val Asn Met Gly Lys Thr His Ala Asn Gln Val Phe Val Asp
                645                 650                 655

Ala Ser Gly Val Thr Asn Thr Lys Leu Val Thr Asp Lys Asn Gly Ile
            660                 665                 670

Leu Thr Val Pro Val Lys Gly Ile Lys Thr Ala Glu Val Asn Gly Tyr
        675                 680                 685

Val Gly Val Phe Val Pro Gln Ala Thr Lys Ala Pro Val Ala Ala Ile
    690                 695                 700

Lys Ala Gly Ala Val Tyr Gln Gly Lys Ala Leu Asp Leu Lys Thr Thr
705                 710                 715                 720

Val Thr Asn Thr Thr Ser Ala Val Ala Ser Thr Arg Tyr Arg Val Leu
                725                 730                 735

Asp Thr Lys Lys Ala Thr Val Asp Ser Lys Gly Arg Leu Thr Gly Lys
            740                 745                 750

Ala Thr Gly Lys Thr Thr Val Glu Ala Thr Val Thr Leu Lys Asp Gly
        755                 760                 765

Phe Val Leu Lys Thr Val Leu Pro Ile Glu Thr Lys Ala Asn Ser Val
    770                 775                 780

Thr Leu Lys Ala Thr Lys Ala Thr Leu Lys Lys Asn Gln Thr Thr Arg
785                 790                 795                 800

Ile Ala Tyr Thr Ser Ala Thr Asp Lys Ile Lys Ser Val Gln Tyr Ala
                805                 810                 815

Ser Ala Asn Lys Lys Val Ala Gln Val Ser Ser Arg Gly Asn Val Lys
            820                 825                 830

Gly Ile Lys Ala Gly Lys Thr Thr Ile Arg Val Thr Tyr Thr Thr Val
        835                 840                 845

Gly Asn Tyr Lys Val Val Lys Thr Phe Thr Val Thr Val Lys
    850                 855                 860

<210> SEQ ID NO 4
<211> LENGTH: 701
<212> TYPE: PRT
<213> ORGANISM: Artificial Sequence
<220> FEATURE:
<223> OTHER INFORMATION: mature alpha-glucanotransferase C-terminally
      truncated

<400> SEQUENCE: 4

Phe Ala Pro Ser Glu Lys Leu Asp Asn Arg Val Ile Phe Gln Ser Phe
1               5                   10                  15

Ser Leu Tyr Gln Pro Tyr Glu Ser Asn Met Tyr Arg Thr Leu Ala Lys
            20                  25                  30

Lys Gly Glu Leu Leu Asn Ser Trp Gly Val Thr Asp Val Trp Leu Pro

```
                35                  40                  45
    Pro Ala Tyr Arg Ser Phe Asp Met Ala Arg Tyr Met Glu Gly Tyr Ala
                                55                  60
                50
    Ile Ala Asp Arg Tyr Asp Leu Gly Glu Phe Pro Gln Gly Pro Gly Gly
 65                  70                  75                  80
    Ser Val Ala Thr Lys Tyr Gly Lys Ala Thr Gln Leu Glu Met Met Val
                    85                  90                  95
    Asp Met Leu His Asp Asp Asn Ile Lys Val Gln Met Asp Leu Val Pro
                100                 105                 110
    Asn Gln Met Leu Gly Leu Asn Lys Arg Glu Ala Val Phe Val Arg Arg
                115                 120                 125
    Ala Thr Ser Ser Gly Glu Pro Phe Met Asn Pro Phe Thr Gly Gly Glu
                130                 135                 140
    Lys Thr Lys Thr Leu Ala Thr Pro Tyr Leu Ala Tyr Thr Lys Gly Gly
145                 150                 155                 160
    Gly Met Gly Gln Glu Lys Tyr Gly Tyr Leu Lys Glu Trp Asn Lys Ser
                    165                 170                 175
    Phe Ile Asn Gly Thr Ser Leu Gln Gly Gln Gly Met Gly Arg Val Met
                180                 185                 190
    Thr Asp Lys Asp Gly Lys Pro Tyr Arg Tyr Phe Gly Lys Asp Asp Ala
                195                 200                 205
    Asn Asn Tyr Leu Pro Glu Trp Leu Leu Asp Ala Ala Lys Thr Gln Asn
                210                 215                 220
    Leu Asn Val Val Asp Thr Tyr Leu Ala Ala Asp Gly Trp Tyr Glu Val
225                 230                 235                 240
    Ser Pro Glu Asn Trp Lys Pro Met Leu Ser Gln Tyr Ala Lys Asp Glu
                    245                 250                 255
    Gly Tyr Leu Glu Tyr Met Lys Gln Asn Gly Phe Glu Thr Lys Glu Ala
                260                 265                 270
    Leu Leu Thr Ser Thr Glu Asn Thr Lys Ile Ala Ser Leu Thr Glu Glu
                275                 280                 285
    Tyr Met Lys Thr Gln Ala Ala Tyr Gly Tyr Gly Ser Glu Glu Arg Ser
                290                 295                 300
    Tyr Gln Asn Asp Asn Ser Gly Ile Asp Ile Glu Asp Gln Phe Leu Phe
305                 310                 315                 320
    Val Asp Glu Thr Gly Phe Pro Thr Gln Ala Tyr Asn Lys Thr Met Thr
                    325                 330                 335
    Asn Asn Asp Glu Phe Leu Ile Gly Val Asp Leu Ala Asn Ser Asn Pro
                340                 345                 350
    Glu Val Ile Lys Glu Gln Lys Asn Trp Met Lys Trp Met Leu Glu Thr
                355                 360                 365
    Tyr Lys Phe Asp Gly Phe Arg Ile Asp Ala Ala Ser His Tyr Asp Thr
                370                 375                 380
    Ala Ile Leu Lys Ala Glu Ala Glu Ile Ser Lys Ala His Phe Gly Lys
385                 390                 395                 400
    Gln Asp Tyr Leu Ser Tyr Ile Glu Ser Tyr Lys Thr Glu Gln Asn Ala
                    405                 410                 415
    Tyr Met Lys Ala Asn Asn Asn Glu Gln Leu Val Met Asp Gly Glu Leu
                420                 425                 430
    Tyr Phe Thr Leu Arg Ser Ala Leu Thr Pro Ser Asn Lys Arg Ala Leu
                435                 440                 445
    Arg Asp Leu Ala Lys Val Ser Val Val Asn Arg Glu Gly Asp Gly Ala
                450                 455                 460
```

```
Thr Asn Val Gln Ala Asn Trp Ser Phe Val Asn Asn His Asp Gln Glu
465                 470                 475                 480

Lys Asn Arg Val Asn Gln Ile Met Leu Asp Ala Tyr Gly Ile Lys Thr
            485                 490                 495

Asn Thr Gln Tyr Gly Lys Asp Gly Glu Pro Lys Ser Phe Glu Lys Leu
        500                 505                 510

Tyr Asn Lys Glu Asp Glu Ala Lys Ala Leu Ala Ile Tyr Asn Lys Glu
    515                 520                 525

Leu Ala Ser Pro Thr Lys Lys Tyr Ser Thr Glu Asn Val Val Ala Gln
530                 535                 540

Tyr Ala Phe Leu Leu Ser Asn Lys Asn Thr Val Pro Thr Val Tyr Tyr
545                 550                 555                 560

Gly Asp Leu Tyr Gln Thr Asp Ala Ser Tyr Met Ser Lys Thr Thr Pro
                565                 570                 575

Tyr Tyr Asp Glu Ile Thr Asn Leu Leu Lys Val Arg Lys Gln Tyr Ala
            580                 585                 590

Tyr Gly Lys Gln His Val Ala Tyr His Thr Ser Asn Thr Ser Lys Glu
        595                 600                 605

Ala Gly Lys Asp Leu Ile Ser Ser Val Arg Phe Gly Lys Asp Arg Asn
610                 615                 620

Thr Gly Val Ala Thr Val Ile Gly Lys Asn Ala Ala Leu Asp Thr Thr
625                 630                 635                 640

Val Gln Val Asn Met Gly Lys Thr His Ala Asn Gln Val Phe Val Asp
                645                 650                 655

Ala Ser Gly Val Thr Asn Thr Lys Leu Val Thr Asp Lys Asn Gly Ile
            660                 665                 670

Leu Thr Val Pro Val Lys Gly Ile Lys Thr Ala Glu Val Asn Gly Tyr
        675                 680                 685

Val Gly Val Phe Val Pro Gln Ala Thr Lys Ala Pro Val
690                 695                 700
```

<210> SEQ ID NO 5
<211> LENGTH: 2640
<212> TYPE: DNA
<213> ORGANISM: Artificial Sequence
<220> FEATURE:
<223> OTHER INFORMATION: synthetic nucleotide sequence of the mature gene encoding alpha-GT-E

<400> SEQUENCE: 5

```
tttgcgctga cactgatttt tacaatggcg ttttcaaata tgagcgctag cgcatttgca      60
ccgtcagaaa aactggataa tcgcgttatt tttcagagct tttcactgta tcaaccgtat     120
gaaagcaaca tgtatagaac actggcaaaa aaaggcgaac tgcttaattc atggggagtt     180
acagatgttt ggctgcctcc ggcatataga tcatttgata tggcaagata tatggaaggc     240
tatgcgattg cggatagata tgatctgggc gaatttccgc aaggccctgg cggatcagtt     300
gcaacaaaat atggcaaagc aacacagctg gaaatgatgg ttgatatgct gcatgatgac     360
aacatcaaag tccaaatgga tctggttccg aatcaaatgc tgggcctgaa taaaagagaa     420
gcagtttttg ttagacgcgc aacatcatca ggcgaaccgt ttatgaatcc gtttacaggc     480
ggagaaaaaa caaaacact ggcaacaccg tatctggcgt atacaaaagg cggaggcatg     540
ggccaagaaa atatggcta tctgaaagaa tggaacaaat catttatcaa cggcacatca     600
ctgcaaggcc aaggcatggg cagagttatg acagataaag atggcaaacc gtatcgctat     660
```

```
tttggcaaag atgatgcgaa taactatctg ccggaatggc tgctggatgc agcaaaaaca    720
caaaatctga atgtcgtcga tacatatctg cagcagatg gctggtatga agtttcaccg    780
gaaaattgga aaccgatgct gtcacaatat gcaaagatg aaggctacct ggaatatatg    840
aaacagaacg gctttgaaac aaaagaagca ctgctgacaa gcacggaaaa tacaaaaatc    900
gcgagcctga cggaagaata catgaaaaca caagcagcgt atggctatgg ctcagaagaa    960
agatcatatc agaatgataa cagcggcatc gatattgaag atcagtttct gtttgttgat   1020
gaaacaggct ttccgacaca agcgtataac aaaacaatga cgaacaatga tgaatttctg   1080
atcggcgttg atctggcaaa ttcaaatccg gaagttatta agaacagaa aaattggatg   1140
aaatggatgc tggaaacata caaatttgac ggctttagaa ttgatgcagc gagccattat   1200
gatacagcaa ttctgaaagc agaagcggaa attagcaaag cgcattttgg caaacaagac   1260
tatctgagct atattgaaag ctataaaacg gaacagaatg cgtatatgaa agcgaacaat   1320
aatgaacagc tggtcatgga tggcgaactg tattttacac tgagatcagc actgacaccg   1380
agcaataaaa gagcactgag agatctggca aaagttagcg ttgttaatag agaaggtgat   1440
ggcgcaacaa atgttcaagc aaattggagc tttgtcaata atcatgatca agaaaaaaac   1500
cgcgtcaatc agattatgct ggatgcgtat ggcatcaaaa caaatacaca gtatggcaaa   1560
gatggcgaac cgaaatcatt tgaaaaactg tataacaaag aagatgaagc gaaagcgctg   1620
gcgatttaca ataaagaact ggcatcaccg acgaaaaaat acagcacaga aatgttgtt   1680
gcgcagtatg catttctgct gagcaataaa aacacagtcc cgacagttta ttatggcgat   1740
ctgtatcaga cagatgcaag ctatatgtca aaacgacgc cgtattatga cgaaatcaca   1800
aatctgctga agtccgcaa acaatatgct tatggcaaac aacatgtcgc gtatcataca   1860
agcaacacat caaagaagc aggcaaagac ctgattagct cagtcagatt tggaaaagat   1920
agaaatacag gcgttgcaac agtcattggc aaaaatgcag cactggatac aacagtccaa   1980
gtcaatatgg gcaaaacaca tgcgaatcaa gtttttgtcg acgcatcagg cgtcacaaat   2040
acaaaactgg tcacagataa aaacggcatt ctgacagttc cggtcaaagg cattaaaaca   2100
gcggaagtta atggctatgt tggcgttttt gttccgcaag caacaaaagc accggttgca   2160
gcaattaaag caggcgcagt ttatcaaggc aaagcactgg atctgaaaac aacagtgaca   2220
aatacaacat cagcagttgc gagcacaaga tatagagttc tggatacaaa aaagcgacg   2280
gttgattcaa aaggcagact gacaggcaaa gcgacaggca aacaacagt tgaagcaaca   2340
gttacactga agatggcttt tgttctgaaa acagttctgc cgatcgaaac aaaagcaaat   2400
tcagttacac ttaaagccac aaaagcgaca ctgaaaaaaa accagacaac acgcattgca   2460
tatacaagcg cgacagataa aatcaaaagc gttcaatatg caagcgcgaa caaaaaagtt   2520
gcacaagttt catcaagagg caacgtcaaa ggcatcaaag cgggaaaaac aacaattcgc   2580
gttacatata caacggtcgg caactataaa gtcgtcaaaa catttacagt cacagtcaaa   2640
```

<210> SEQ ID NO 6
<211> LENGTH: 2865
<212> TYPE: DNA
<213> ORGANISM: Bacillus coagulans
<220> FEATURE:
<221> NAME/KEY: misc_feature
<223> OTHER INFORMATION: nucleotide sequence of alpha-GT-S B. coagulans 2-6

<400> SEQUENCE: 6

```
ttggaaaaga aattttttag cagattgtca atattgatgt tgtctttgtt actggttgcc     60
```

```
ggctcgatca gttatttttcc taaatctgcc aaggcttata catccggcac atcgctcgat    120
aaccgcgtga ttttccaaag ttttagcctg tacatgccat atgaaagcaa tatgtacaaa    180
attctttcaa cgaaaggcaa cgaattgaaa gattggggga ttacggatat atggcttccg    240
ccggcttacc gttctttcaa tgcggcacgt tacatggaag gctacgccat tgccgaccgt    300
tatgacctcg gtgaatttaa ccaggggccg aataacactc ggccgaccaa atacggaaca    360
agcgatgaat tgaaaagtat ggtttccgtg cttcacgcaa atggtttaaa agtacaggaa    420
gaccttgtgc ccaaccaggt tctcggattg agcaaaaggg aagcagttta cgtcacacgc    480
gtagatcaag acgaaatttt gtttaaaaat ccttatacaa caggacttgc aacgcaaatc    540
agggccaacc tttatctcgc ttacacaaaa ggtggcggcg aaggacaggc aaaatatggc    600
tatatcaaag aatggaacaa aaaatatttt aacggtacct ccttacaagg gcagggtatg    660
gatcgcgtga tgaaagacag cgagggcaat ccgtaccgtt attttgggcc aaacaacccg    720
aaaaactact tgccaagctg gcttgatgaa gctgcagcag caaataaaat caatacagtt    780
gatacttatt tgccagtaga cggctggtat gctgcaaaag acgcttcgac ttcggataat    840
tattggaaac cgatgttaat gcatgaccct ggctatttaa agtacatgaa aagccatggc    900
tattcatctg ttgacgatat actgaacggc gacaacgggc aaatcgcaag tttaacagat    960
gcgtatattg catcccagcc cgggtacggc ttcggatcgg aagaaaggtc gtttaaaaat   1020
gatgattccg gatcagatga ccaggatcaa ttttttatttg tgaaaagaa tgggacaact   1080 gttcacaacc tttacaacac gatcagcggg cataaccagt ttctggtagg aatggacata   1140
gacaacggga atccaactgt ccaaaaagaa cagatccact ggatgaactg ctacttgat   1200 acgtatcagt ttgacggctt cagaattgat gcggcaggcc attacgataa gcaagtgctg   1260
ctggatgaag gtgacgttat gaaacagcat tttggcagcc atttaaacga ccatttaagc   1320
tatattgaga gttatcaaag tgccgggaca gattttgaaa atgcaaacgg gaatccgcag   1380
ttaatgatgg attatgccct gttctattct ttgcaaaatg ctttgggcaa aaattcgcca   1440
tcaaacagcc tgtcaaccat tgctacaaac gctgttgtca cagggcaag cgcaggcacg   1500 gcgaatccaa cgcctaactg gtcatttgtg aataatcatg accaggaaaa gaaccgtgtg   1560
aataaaatca tgatggacct gtacgtcatt aagccgggta tacattacgg cacatccgca   1620
ccgaaatctt tccaagatct gtatgataaa agacagagg caaaagcttt ggatatttat   1680
gaaaaagaca tggaaagaac ggtaaaaaca tatgcgccat acaatgtgcc gagccagtac   1740
gcatatattt tgacgaataa agataccgtc ccgactgtct tttacggcga cttgtacaaa   1800
acgaatgctt cttacatgag cgagcatacg ccgtattatg atacgattgt gaaattgttg   1860
aaagtgcgca aaaattatgc ctatgggaac cagcaagtaa ccaactataa gtcgaacact   1920
tccggcacgg cgggaaaaga tctaatctca gcgtccgct atggaaaaga ccggaatacc   1980
ggcgtggcaa ccgtaatcgg aaataacccg aaaaccgata cgactattaa agtggacatg   2040
ggtacccggc atgccaacca gctatttgag gatgcaaccg gatttcataa cgaaaagctg   2100
tccacagata gcaaaggcat tttaaccgtt catgtaaaag ggacgcaaaa cgcccaggta   2160
aaagggtatc ttggcgtctg gatcccctca aaaaagcgg caacgccgaa acaaggccct   2220
gcacttcaat acggtaagta tgtaacggta acaaacaagc actatgccgt atatcaagac   2280
ttcaactgga aaaagaaaaa tgtcactgca gtgaataaaa cgtatcttgc caaggtccaa   2340
taccatcaca gcaacggatc aacttacctg tcctttatg acggcaaagg caaatgggta   2400
```

```
ggctatatca acgccaaagc tgtgaaaaca ggaagcggca agcaaggcgc tgcacttcaa    2460
tacggtaagt atgtaacggt aacaaacaag cactatgccg tatatcaaga cttcaactgg    2520
aaaaagaaga atgtcactgc agtgaataaa acgtatcttg ccaaggtcca ataccatcac    2580
agcaacggat caacttacct gtcccttat gatggcaaag gaaatgggt aggctatatc    2640 aacgccaaag ctgtgaaaac aggaagcggc aagcaaggcg ctgcacttca atacggtaag    2700
tatgtaacgg taacaaacaa gcactatgcc gtatatcaag actttcactg gaaaaagaaa    2760
aatgtcactg ccgtgaataa aaacgtatct tgccaaggtc ccaataccat cacagcaacg    2820
gatcaactta cctgtcccct tatgacggca aggaaaatg ggtag                    2865
```

<210> SEQ ID NO 7
<211> LENGTH: 954
<212> TYPE: PRT
<213> ORGANISM: Bacillus coagulans
<220> FEATURE:
<221> NAME/KEY: misc_feature
<223> OTHER INFORMATION: alpha-GT-S from Bacillus coagulans 2-6

<400> SEQUENCE: 7

```
Met Glu Lys Lys Phe Phe Ser Arg Leu Ser Ile Leu Met Leu Ser Leu
1               5                   10                  15

Leu Leu Val Ala Gly Ser Ile Ser Tyr Phe Pro Lys Ser Ala Lys Ala
            20                  25                  30

Tyr Thr Ser Gly Thr Ser Leu Asp Asn Arg Val Ile Phe Gln Ser Phe
        35                  40                  45

Ser Leu Tyr Met Pro Tyr Glu Ser Asn Met Tyr Lys Ile Leu Ser Thr
    50                  55                  60

Lys Gly Asn Glu Leu Lys Asp Trp Gly Ile Thr Asp Ile Trp Leu Pro
65                  70                  75                  80

Pro Ala Tyr Arg Ser Phe Asn Ala Ala Arg Tyr Met Glu Gly Tyr Ala
                85                  90                  95

Ile Ala Asp Arg Tyr Asp Leu Gly Glu Phe Asn Gln Gly Pro Asn Asn
            100                 105                 110

Thr Arg Pro Thr Lys Tyr Gly Thr Ser Asp Glu Leu Lys Ser Met Val
        115                 120                 125

Ser Val Leu His Ala Asn Gly Leu Lys Val Gln Glu Asp Leu Val Pro
    130                 135                 140

Asn Gln Val Leu Gly Leu Ser Lys Arg Glu Ala Val Tyr Val Thr Arg
145                 150                 155                 160

Val Asp Gln Asp Gly Asn Leu Phe Lys Asn Pro Tyr Thr Thr Gly Leu
                165                 170                 175

Ala Thr Gln Ile Arg Ala Asn Leu Tyr Leu Ala Tyr Thr Lys Gly Gly
            180                 185                 190

Gly Glu Gly Gln Ala Lys Tyr Gly Tyr Ile Lys Glu Trp Asn Lys Lys
        195                 200                 205

Tyr Phe Asn Gly Thr Ser Leu Gln Gly Gln Gly Met Asp Arg Val Met
    210                 215                 220

Lys Asp Ser Glu Gly Asn Pro Tyr Arg Tyr Phe Gly Pro Asn Pro
225                 230                 235                 240

Lys Asn Tyr Leu Pro Ser Trp Leu Asp Glu Ala Ala Ala Asn Lys
                245                 250                 255

Ile Asn Thr Val Asp Thr Tyr Leu Pro Val Asp Gly Trp Tyr Ala Ala
            260                 265                 270

Lys Asp Ala Ser Thr Ser Asp Asn Tyr Trp Lys Pro Met Leu Met His
```

```
                275                 280                 285
Asp Pro Gly Tyr Leu Lys Tyr Met Lys Ser His Gly Tyr Ser Ser Val
290                 295                 300
Asp Asp Ile Leu Asn Gly Asp Asn Gly Gln Ile Ala Ser Leu Thr Asp
305                 310                 315                 320
Ala Tyr Ile Ala Ser Gln Pro Gly Tyr Gly Phe Gly Ser Glu Glu Arg
                325                 330                 335
Ser Phe Lys Asn Asp Asp Ser Gly Ser Asp Asp Gln Asp Gln Phe Leu
                340                 345                 350
Phe Val Lys Lys Asn Gly Thr Thr Val His Asn Leu Tyr Asn Thr Ile
                355                 360                 365
Ser Gly His Asn Gln Phe Leu Val Gly Met Asp Ile Asp Asn Gly Asn
370                 375                 380
Pro Thr Val Gln Lys Glu Gln Ile His Trp Met Asn Trp Leu Leu Asp
385                 390                 395                 400
Thr Tyr Gln Phe Asp Gly Phe Arg Ile Asp Ala Ala His Tyr Asp
                405                 410                 415
Lys Gln Val Leu Leu Asp Glu Gly Asp Val Met Lys Gln His Phe Gly
                420                 425                 430
Ser His Leu Asn Asp His Leu Ser Tyr Ile Glu Ser Tyr Gln Ser Ala
                435                 440                 445
Gly Thr Asp Phe Glu Asn Ala Asn Gly Asn Pro Gln Leu Met Met Asp
450                 455                 460
Tyr Ala Leu Phe Tyr Ser Leu Gln Asn Ala Leu Gly Lys Asn Ser Pro
465                 470                 475                 480
Ser Asn Ser Leu Ser Thr Ile Ala Thr Asn Ala Val Val Asn Arg Ala
                485                 490                 495
Ser Ala Gly Thr Ala Asn Pro Thr Pro Asn Trp Ser Phe Val Asn Asn
                500                 505                 510
His Asp Gln Glu Lys Asn Arg Val Asn Lys Ile Met Met Asp Leu Tyr
                515                 520                 525
Val Ile Lys Pro Gly Ile His Tyr Gly Thr Ser Ala Pro Lys Ser Phe
530                 535                 540
Gln Asp Leu Tyr Asp Lys Lys Thr Glu Ala Lys Ala Leu Asp Ile Tyr
545                 550                 555                 560
Glu Lys Asp Met Glu Arg Thr Val Lys Thr Tyr Ala Pro Tyr Asn Val
                565                 570                 575
Pro Ser Gln Tyr Ala Tyr Ile Leu Thr Asn Lys Asp Thr Val Pro Thr
                580                 585                 590
Val Phe Tyr Gly Asp Leu Tyr Lys Thr Asn Ala Ser Tyr Met Ser Glu
                595                 600                 605
His Thr Pro Tyr Tyr Asp Thr Ile Val Lys Leu Leu Lys Val Arg Lys
                610                 615                 620
Asn Tyr Ala Tyr Gly Asn Gln Gln Val Thr Asn Tyr Lys Ser Asn Thr
625                 630                 635                 640
Ser Gly Thr Ala Gly Lys Asp Leu Ile Ser Ser Val Arg Tyr Gly Lys
                645                 650                 655
Asp Arg Asn Thr Gly Val Ala Thr Val Ile Gly Asn Asn Pro Lys Thr
                660                 665                 670
Asp Thr Thr Ile Lys Val Asp Met Gly Thr Arg His Ala Asn Gln Leu
                675                 680                 685
Phe Glu Asp Ala Thr Gly Phe His Asn Glu Lys Leu Ser Thr Asp Ser
690                 695                 700
```

```
Lys Gly Ile Leu Thr Val His Val Lys Gly Thr Gln Asn Ala Gln Val
705                 710                 715                 720

Lys Gly Tyr Leu Gly Val Trp Ile Pro Ser Lys Lys Ala Ala Thr Pro
            725                 730                 735

Lys Gln Gly Pro Ala Leu Gln Tyr Gly Lys Tyr Val Thr Val Thr Asn
            740                 745                 750

Lys His Tyr Ala Val Tyr Gln Asp Phe Asn Trp Lys Lys Lys Asn Val
            755                 760                 765

Thr Ala Val Asn Lys Thr Tyr Leu Ala Lys Val Gln Tyr His His Ser
770                 775                 780

Asn Gly Ser Thr Tyr Leu Ser Leu Tyr Asp Gly Lys Gly Lys Trp Val
785                 790                 795                 800

Gly Tyr Ile Asn Ala Lys Ala Val Lys Thr Gly Ser Gly Lys Gln Gly
                805                 810                 815

Ala Ala Leu Gln Tyr Gly Lys Tyr Val Thr Val Thr Asn Lys His Tyr
            820                 825                 830

Ala Val Tyr Gln Asp Phe Asn Trp Lys Lys Lys Asn Val Thr Ala Val
            835                 840                 845

Asn Lys Thr Tyr Leu Ala Lys Val Gln Tyr His His Ser Asn Gly Ser
850                 855                 860

Thr Tyr Leu Ser Leu Tyr Asp Gly Lys Gly Lys Trp Val Gly Tyr Ile
865                 870                 875                 880

Asn Ala Lys Ala Val Lys Thr Gly Ser Gly Lys Gln Gly Ala Ala Leu
                885                 890                 895

Gln Tyr Gly Lys Tyr Val Thr Val Thr Asn Lys His Tyr Ala Val Tyr
            900                 905                 910

Gln Asp Phe His Trp Lys Lys Lys Asn Val Thr Ala Val Asn Lys Asn
            915                 920                 925

Val Ser Cys Gln Gly Pro Asn Thr Ile Thr Ala Thr Asp Gln Leu Thr
930                 935                 940

Cys Pro Phe Met Thr Ala Lys Glu Asn Gly
945                 950
```

<210> SEQ ID NO 8
<211> LENGTH: 704
<212> TYPE: PRT
<213> ORGANISM: Bacillus coagulans
<220> FEATURE:
<221> NAME/KEY: misc_feature
<223> OTHER INFORMATION: alpha-GT-S with C-terminal truncation used for
      expression based on alpha-GT-E

<400> SEQUENCE: 8

```
Tyr Thr Ser Gly Thr Ser Leu Asp Asn Arg Val Ile Phe Gln Ser Phe
1               5                   10                  15

Ser Leu Tyr Met Pro Tyr Glu Ser Asn Met Tyr Lys Ile Leu Ser Thr
            20                  25                  30

Lys Gly Asn Glu Leu Lys Asp Trp Gly Ile Thr Asp Ile Trp Leu Pro
        35                  40                  45

Pro Ala Tyr Arg Ser Phe Asn Ala Ala Arg Tyr Met Glu Gly Tyr Ala
    50                  55                  60

Ile Ala Asp Arg Tyr Asp Leu Gly Glu Phe Asn Gln Gly Pro Asn Asn
65              70                  75                  80

Thr Arg Pro Thr Lys Tyr Gly Thr Ser Asp Glu Leu Lys Ser Met Val
                85                  90                  95
```

```
Ser Val Leu His Ala Asn Gly Leu Lys Val Gln Glu Asp Leu Val Pro
            100                 105                 110

Asn Gln Val Leu Gly Leu Ser Lys Arg Glu Ala Val Tyr Val Thr Arg
        115                 120                 125

Val Asp Gln Asp Gly Asn Leu Phe Lys Asn Pro Tyr Thr Thr Gly Leu
130                 135                 140

Ala Thr Gln Ile Arg Ala Asn Leu Tyr Leu Ala Tyr Thr Lys Gly Gly
145                 150                 155                 160

Gly Glu Gly Gln Ala Lys Tyr Gly Tyr Ile Lys Glu Trp Asn Lys Lys
                165                 170                 175

Tyr Phe Asn Gly Thr Ser Leu Gln Gly Gln Gly Met Asp Arg Val Met
            180                 185                 190

Lys Asp Ser Glu Gly Asn Pro Tyr Arg Tyr Phe Gly Pro Asn Asn Pro
        195                 200                 205

Lys Asn Tyr Leu Pro Ser Trp Leu Asp Glu Ala Ala Ala Asn Lys
210                 215                 220

Ile Asn Thr Val Asp Thr Tyr Leu Pro Val Asp Gly Trp Tyr Ala Ala
225                 230                 235                 240

Lys Asp Ala Ser Thr Ser Asp Asn Tyr Trp Lys Pro Met Leu Met His
                245                 250                 255

Asp Pro Gly Tyr Leu Lys Tyr Met Lys Ser His Gly Tyr Ser Ser Val
            260                 265                 270

Asp Asp Ile Leu Asn Gly Asp Asn Gly Gln Ile Ala Ser Leu Thr Asp
        275                 280                 285

Ala Tyr Ile Ala Ser Gln Pro Gly Tyr Gly Phe Gly Ser Glu Arg
290                 295                 300

Ser Phe Lys Asn Asp Asp Ser Gly Ser Asp Asp Gln Asp Gln Phe Leu
305                 310                 315                 320

Phe Val Lys Lys Asn Gly Thr Thr Val His Asn Leu Tyr Asn Thr Ile
                325                 330                 335

Ser Gly His Asn Gln Phe Leu Val Gly Met Asp Ile Asp Asn Gly Asn
            340                 345                 350

Pro Thr Val Gln Lys Glu Gln Ile His Trp Met Asn Trp Leu Leu Asp
        355                 360                 365

Thr Tyr Gln Phe Asp Gly Phe Arg Ile Asp Ala Ala Gly His Tyr Asp
370                 375                 380

Lys Gln Val Leu Leu Asp Glu Gly Asp Val Met Lys Gln His Phe Gly
385                 390                 395                 400

Ser His Leu Asn Asp His Leu Ser Tyr Ile Glu Ser Tyr Gln Ser Ala
                405                 410                 415

Gly Thr Asp Phe Glu Asn Ala Asn Gly Asn Pro Gln Leu Met Met Asp
            420                 425                 430

Tyr Ala Leu Phe Tyr Ser Leu Gln Asn Ala Leu Gly Lys Asn Ser Pro
        435                 440                 445

Ser Asn Ser Leu Ser Thr Ile Ala Thr Asn Ala Val Val Asn Arg Ala
450                 455                 460

Ser Ala Gly Thr Ala Asn Pro Thr Pro Asn Trp Ser Phe Val Asn Asn
465                 470                 475                 480

His Asp Gln Glu Lys Asn Arg Val Asn Lys Ile Met Met Asp Leu Tyr
                485                 490                 495

Val Ile Lys Pro Gly Ile His Tyr Gly Thr Ser Ala Pro Lys Ser Phe
            500                 505                 510

Gln Asp Leu Tyr Asp Lys Lys Thr Glu Ala Lys Ala Leu Asp Ile Tyr
```

```
           515                 520                 525
Glu Lys Asp Met Glu Arg Thr Val Lys Thr Tyr Ala Pro Tyr Asn Val
           530                 535                 540

Pro Ser Gln Tyr Ala Tyr Ile Leu Thr Asn Lys Asp Thr Val Pro Thr
545                 550                 555                 560

Val Phe Tyr Gly Asp Leu Tyr Lys Thr Asn Ala Ser Tyr Met Ser Glu
                565                 570                 575

His Thr Pro Tyr Tyr Asp Thr Ile Val Lys Leu Leu Lys Val Arg Lys
            580                 585                 590

Asn Tyr Ala Tyr Gly Asn Gln Gln Val Thr Asn Tyr Lys Ser Asn Thr
        595                 600                 605

Ser Gly Thr Ala Gly Lys Asp Leu Ile Ser Ser Val Arg Tyr Gly Lys
    610                 615                 620

Asp Arg Asn Thr Gly Val Ala Thr Val Ile Gly Asn Asn Pro Lys Thr
625                 630                 635                 640

Asp Thr Thr Ile Lys Val Asp Met Gly Thr Arg His Ala Asn Gln Leu
                645                 650                 655

Phe Glu Asp Ala Thr Gly Phe His Asn Glu Lys Leu Ser Thr Asp Ser
            660                 665                 670

Lys Gly Ile Leu Thr Val His Val Lys Gly Thr Gln Asn Ala Gln Val
        675                 680                 685

Lys Gly Tyr Leu Gly Val Trp Ile Pro Ser Lys Lys Ala Ala Thr Pro
    690                 695                 700

<210> SEQ ID NO 9
<211> LENGTH: 2112
<212> TYPE: DNA
<213> ORGANISM: Artificial Sequence
<220> FEATURE:
<223> OTHER INFORMATION: synthetic nucleotide sequence of the mature and
      3' deleted gene encoding alpha-GT-S

<400> SEQUENCE: 9
tatacatcag gcacatcact ggataatcgc gtcattttc  agagctttc  actgtacatg      60 ccgtatgaaa gcaacatgta taaaatcctg agcacaaaag gcaatgaact gaaagattgg     120
ggcattacag atatttggct gcctccggca tatagatcat ttaatgcagc aagatatatg     180
gaaggctatg cgattgcaga tagatatgat ctgggcgaat ttaatcaggg accgaataat     240
acacgtccga caaaatatgg cacaagcgac gaactgaaat caatggttag cgttctgcat     300
gcaaatggcc tgaaagttca gaagatctg  gttccgaatc aagttctggg cctgtcaaaa     360
cgcgaagcag tttatgttac aagagttgat caagacggca acctgtttaa aaacccgtat     420
acaacaggcc tggcaacaca aattagagca atctctgtatc tggcgtatac aaaaggcgga     480
ggcgaaggcc aagcaaaata tggctatatc aaagaatgga caaaaaata  ctttaatggc     540 acaagcctgc aaggccaagg catggataga gttatgaaag attcagaagg caacccgtat     600
agatattttg gaccgaataa cccgaaaaac tatctgccgt catggctgga tgaagcagca     660
gcagcgaata aaatcaatac agtcgataca tatctgccgg ttgatggctg gtatgcagca     720
aaagatgcat caacatcaga caactattgg aaaccgatgc tgatgcatga tccgggatat     780
ctgaaataca tgaaatcaca tggctatagc agcgtcgatg atattctgaa tggcgataat     840
ggccaaattg catcactgac agatgcatat attgcatcac aaccgggata tggctttggc     900
tcagaagaac gcagctttaa aaacgatgat tcaggctcag atgatcagga ccaatttctg     960
tttgtcaaaa aaaacggcac aacggtccat aacctgtata atacaatttc aggccataat    1020
```

```
cagtttctgg tcggcatgga tattgataat ggcaatccga cagtccagaa agaacaaatt    1080
cattggatga attggctgct ggacacgtat caatttgatg ctttagaat tgatgcggca    1140 ggccattatg ataaacaagt tctgctggat gaaggcgacg ttatgaaaca acattttggc    1200
tcacatctga atgaccatct gtcatatatc gaaagctatc aatcagcagg cacggatttt    1260
gaaaatgcaa atggaaatcc gcagctgatg atggattatg cactgtttta tagcctgcaa    1320
aatgcgctgg gcaaaaattc accgtcaaat tcactgtcaa caattgcaac aaatgcagtc    1380
gttaatagag caagcgcagg cacagcaaat ccgacaccga attggtcatt tgtcaataac    1440
catgatcaag aaaaaaaccg cgtcaacaaa atcatgatgg acctgtatgt tatcaaaccg    1500
ggaatccatt atggcacatc agcaccgaaa tcatttcaag acctgtacga caaaaaaacg    1560
gaagcaaaag cgctggacat ctacgaaaaa gatatggaaa gaacggtcaa aacgtatgca    1620
ccgtataatg ttccgagcca gtatgcatat atcctgacaa ataaagatac agtcccgacg    1680
gttttttatg gcgatctgta taaaacaaac gcgagctata tgtcagaaca cacgccgtat    1740
tatgacacga ttgtcaaact gctgaaagtc cgcaaaaact atgcgtatgg caatcaacag    1800
gtcacaaact acaaatcaaa tacaagcggc acagcaggca agatctgat ttcatcagtt    1860 cgctatggca agatagaaa tacaggcgtt gcaacagtca ttggcaataa tccgaaaacg    1920 gatcaacga tcaaagtcga tatgggcaca agacatgcaa atcagctgtt tgaagatgca    1980
acaggctttc ataatgaaaa actgagcaca gatagcaaag gcattctgac agttcatgtt    2040
aaaggcacac aaaatgcaca ggttaaaggc tatctgggcg tttggattcc gtcaaaaaaa    2100
gcagcaacac cg                                                       2112
```

<210> SEQ ID NO 10
<211> LENGTH: 2637
<212> TYPE: DNA
<213> ORGANISM: Bacillus coagulans
<220> FEATURE:
<221> NAME/KEY: misc_feature
<223> OTHER INFORMATION: alpha -GT-L  B. coagulans 2022696

<400> SEQUENCE: 10

```
ttgatattgt ctgtgttact ggttgccggt tcgatcagtt attttcctaa atctgccaag     60
gcttatacat ccggtacatc gctcgataac cgcgtaattt ttcaaagctt tagcctgtac    120
atgccatatg aaagcaatat gtacaaaatt cttttcagcga aaggcagcga attgaaagat    180
tggggcatta cggatatatg gctccctccg gcttaccgtt ctttcaacat ggcgcgttac    240
atggaaggct acgccattgc cgaccgttat gacctcggtg aatttaacca ggggccgaat    300
aacacccggc cgaccaaata cgggacaagc gatgaattga aagtatggt ttccgcgctt    360 cacgcaagtg gtttaaaagt gcaagaagat cttgtaccca accaggttct cggattgggc    420
aaaagggaag cggtttacgt cacacgcgta gatcaaaacg gaaatttgtt taaaaatcct    480
tatacaacag gacttacaac gcaaatcagg gccgacctgt acctcgctta tacaaaaggc    540
ggcggcgaag acaggcaaa atatggctac attaagaat ggaataaaaa gtattttaac    600
ggcacctccg tacaaggaca aggtatggat cgtgtgatga agacagcga gggcattccg    660 taccgatatt ttgggccaaa caacccgaaa aaccacttgc caagctggct taatgaagct    720
gcagcggcaa ataaaatcaa tacagttgat acttatttgg cagtagacgg ctggtatgct    780
gctaaagacg cttcgacttc ggataattat tggaaaccg tgttaatgaa ctatgacccc    840
ggctatttaa agtacatgaa aagccatggc tattcatctg ttgacgatat actgaacggc    900
```

-continued

```
gataatggac aaatcgcaag tttaacagat gcctatattg catcacaacc ctgctacggc    960
tttggatcgg aagaaagatc attcaaaaat gacaattccg gatcagatga ccaggatcag   1020
tttctatttg tgaaaaagaa tgggacaacc cttcacaacc ttaacaacac gatcagcggg   1080
caaaaacagt ttctgttagg aatggacata gacaacggga atccaactgt ccaaaaagaa   1140
cagatccact ggatgaactg gctgcttgat acgtatcagt ttgatggctt cagaattgat   1200
gccgcaagcc attatgataa gcaagtattg ctggatgaag ccgacgtcat gaaacagcat   1260
tttggcagca atttaaacga ccatttaagc tatattgaga cttatgaaag tgccgggaca   1320
aattttgaaa acgcaaatgg gaatccgcag ttaatgatgg attatgccct gttctattct   1380
ttgcaaaatg ctttgggcaa aaattcgcca tcaaacaacc tttccaccat tgctacaaac   1440
gctgttgtaa acagggcagg tgcaggcacg gcgaacgcaa cgccaaactg gtcatttgtt   1500
aataatcatg accaggaaaa gaatcgtgtg aaccgtatca tgctggacca gtacggcatt   1560
aagccgggga cgcattacgg cacatccaca ccgaaggctt tccaggatct gtatgataaa   1620
aagacagagg caaaagcttt ggacatctat gaaagagaca tggaaagcac ggtaaaaaaa   1680
tatgcgccat ccaatgtgcc aagccagtac gcatatgttt tgacgaataa agacaccgtc   1740
ccgactgtct tttatggcga cttgtacaaa acgaatgcat cctacatgag tgaacgtacg   1800
ccgtattacg atacgattgt gaaattgctg aaagtgcgca aaaactatgc ctacgggaac   1860
cagcaagtaa ctaactataa gtcgaatact tccagcacgg cgggaaaaga tttgatctca   1920
agcgtccgct atggaaatga ccggaatacc ggcgtggcaa ccgtaatcgg aaataacccg   1980
aaaaccgata cgactattaa agtgaatatg ggatcccggc atgccaacca gctatttgag   2040
gatgcaaccg gattccataa cgaaaagctg gtcacagata gcaaaggcgt tttaaccgtt   2100
catgtaaaag ggacacaaaa tgcccgggta aagggtacc ttggcgtctg gatcccggca   2160
aaaaaagcgg caacgccaaa acaaggcccct gcacttaaat acggtaagta tgtaacgata   2220
acaaacaagc actatgccgt atatcaagac ttcaactgga agaagaagaa tgtcaatgca   2280
gtgaataaaa cgtatcttgc caaggtccaa taccatcaca gcaacggatc aacttatctg   2340 tcccttatg atggcaaagg aaaatgggct ggctatatca atgccaaggc agcgaaaaacc   2400 ggaagcggca agcaaggtgc tgccattcaa tacggcaaat ccgtcaaagt aaccagcaag   2460
aactacgccg tatatcaaaa ctttaactgg aagaagaaaa atatccgggc cgtaaacaaa   2520
acatatttgg cgaagtacat ttattatcat ataaatgggc taagctacct gtcccttat   2580 gataacaagg gcaaatggat aggctacatc aatgccaaag cagttaaaag caaataa      2637
```

<210> SEQ ID NO 11
<211> LENGTH: 1756
<212> TYPE: PRT
<213> ORGANISM: Bacillus coagulans
<220> FEATURE:
<221> NAME/KEY: misc_feature
<223> OTHER INFORMATION: alpha-GT-L

<400> SEQUENCE: 11

```
Leu Ile Leu Ser Val Leu Leu Val Ala Gly Ser Ile Ser Tyr Phe Pro
1               5                   10                  15

Lys Ser Ala Lys Ala Tyr Thr Ser Gly Thr Ser Leu Asp Asn Arg Val
            20                  25                  30

Ile Phe Gln Ser Phe Ser Leu Tyr Met Pro Tyr Glu Ser Asn Met Tyr
        35                  40                  45
```

-continued

```
Lys Ile Leu Ser Ala Lys Gly Ser Glu Leu Lys Asp Trp Gly Ile Thr
 50                  55                  60

Asp Ile Trp Leu Pro Pro Ala Tyr Arg Ser Phe Asn Met Ala Arg Tyr
 65                  70                  75                  80

Met Glu Gly Tyr Ala Ile Ala Asp Arg Tyr Asp Leu Gly Phe Asn
                 85                  90                  95

Gln Gly Pro Asn Asn Thr Arg Pro Thr Lys Tyr Gly Thr Ser Asp Glu
                100                 105                 110

Leu Lys Ser Met Val Ser Ala Leu His Ala Ser Gly Leu Lys Val Gln
            115                 120                 125

Glu Asp Leu Val Pro Asn Gln Val Leu Gly Leu Gly Lys Arg Glu Ala
130                 135                 140

Val Tyr Val Thr Arg Val Asp Gln Asn Gly Asn Leu Phe Lys Asn Pro
145                 150                 155                 160

Tyr Thr Thr Gly Leu Thr Thr Gln Ile Arg Ala Asp Leu Tyr Leu Ala
                165                 170                 175

Tyr Thr Lys Gly Gly Glu Gly Gln Ala Lys Tyr Gly Tyr Ile Lys
            180                 185                 190

Glu Trp Asn Lys Lys Tyr Phe Asn Gly Thr Ser Val Gln Gly Gln Gly
            195                 200                 205

Met Asp Arg Val Met Lys Asp Ser Glu Gly Ile Pro Tyr Arg Tyr Phe
210                 215                 220

Gly Pro Asn Asn Pro Lys Asn His Leu Pro Ser Trp Leu Asn Glu Ala
225                 230                 235                 240

Ala Ala Ala Asn Lys Ile Asn Thr Val Asp Thr Tyr Leu Ala Val Asp
                245                 250                 255

Gly Trp Tyr Ala Ala Lys Asp Ala Ser Thr Ser Asp Asn Tyr Trp Lys
            260                 265                 270

Pro Met Leu Met Asn Tyr Asp Pro Gly Tyr Leu Lys Tyr Met Lys Ser
            275                 280                 285

His Gly Tyr Ser Ser Val Asp Asp Ile Leu Asn Gly Asp Asn Gly Gln
            290                 295                 300

Ile Ala Ser Leu Thr Asp Ala Tyr Ile Ala Ser Gln Pro Cys Tyr Gly
305                 310                 315                 320

Phe Gly Ser Glu Glu Arg Ser Phe Lys Asn Asp Asn Ser Gly Ser Asp
                325                 330                 335

Asp Gln Asp Gln Phe Leu Phe Val Lys Lys Asn Gly Thr Thr Leu His
            340                 345                 350

Asn Leu Asn Asn Thr Ile Ser Gly Gln Lys Gln Phe Leu Leu Gly Met
            355                 360                 365

Asp Ile Asp Asn Gly Asn Pro Thr Val Gln Lys Glu Gln Ile His Trp
370                 375                 380

Met Asn Trp Leu Leu Asp Thr Tyr Gln Phe Asp Gly Phe Arg Ile Asp
385                 390                 395                 400

Ala Ala Ser His Tyr Asp Lys Gln Val Leu Leu Asp Glu Ala Asp Val
                405                 410                 415

Met Lys Gln His Phe Gly Ser Asn Leu Asn Asp His Leu Ser Tyr Ile
            420                 425                 430

Glu Thr Tyr Glu Ser Ala Gly Thr Asn Phe Glu Asn Ala Asn Gly Asn
            435                 440                 445

Pro Gln Leu Met Met Asp Tyr Ala Leu Phe Tyr Ser Leu Gln Asn Ala
450                 455                 460

Leu Gly Lys Asn Ser Pro Ser Asn Asn Leu Ser Thr Ile Ala Thr Asn
```

```
            465                 470                 475                 480
        Ala Val Val Asn Arg Ala Gly Ala Gly Thr Ala Asn Ala Thr Pro Asn
                            485                 490                 495

Trp Ser Phe Val Asn Asn His Asp Gln Glu Lys Asn Arg Val Asn Arg
                            500                 505                 510

Ile Met Leu Asp Gln Tyr Gly Ile Lys Pro Gly Thr His Tyr Gly Thr
                            515                 520                 525

Ser Thr Pro Lys Ala Phe Gln Asp Leu Tyr Asp Lys Lys Thr Glu Ala
                    530                 535                 540

Lys Ala Leu Asp Ile Tyr Glu Arg Asp Met Glu Ser Thr Val Lys Lys
        545                 550                 555                 560

Tyr Ala Pro Ser Asn Val Pro Ser Gln Tyr Ala Tyr Val Leu Thr Asn
                            565                 570                 575

Lys Asp Thr Val Pro Thr Val Phe Tyr Gly Asp Leu Tyr Lys Thr Asn
                        580                 585                 590

Ala Ser Tyr Met Ser Glu Arg Thr Pro Tyr Tyr Asp Thr Ile Val Lys
                    595                 600                 605

Leu Leu Lys Val Arg Lys Asn Tyr Ala Tyr Gly Asn Gln Gln Val Thr
        610                 615                 620

Asn Tyr Lys Ser Asn Thr Ser Ser Thr Ala Gly Lys Asp Leu Ile Ser
        625                 630                 635                 640

Ser Val Arg Tyr Gly Asn Asp Arg Asn Thr Gly Val Ala Thr Val Ile
                            645                 650                 655

Gly Asn Asn Pro Lys Thr Asp Thr Thr Ile Lys Val Asn Met Gly Ser
                        660                 665                 670

Arg His Ala Asn Gln Leu Phe Glu Asp Ala Thr Gly Phe His Asn Glu
                    675                 680                 685

Lys Leu Val Thr Asp Ser Lys Gly Val Leu Thr Val His Val Lys Gly
                    690                 695                 700

Thr Gln Asn Ala Arg Val Lys Gly Tyr Leu Gly Val Trp Ile Pro Ala
        705                 710                 715                 720

Lys Lys Ala Ala Thr Pro Lys Gln Gly Pro Ala Leu Lys Tyr Gly Lys
                        725                 730                 735

Tyr Val Thr Ile Thr Asn Lys His Tyr Ala Val Tyr Gln Asp Phe Asn
                            740                 745                 750

Trp Lys Lys Lys Asn Val Asn Ala Val Asn Lys Thr Tyr Leu Ala Lys
                    755                 760                 765

Val Gln Tyr His His Ser Asn Gly Ser Thr Tyr Leu Ser Leu Tyr Asp
            770                 775                 780

Gly Lys Gly Lys Trp Ala Gly Tyr Ile Asn Ala Lys Ala Ala Lys Thr
        785                 790                 795                 800

Gly Ser Gly Lys Gln Gly Ala Ala Ile Gln Tyr Gly Lys Ser Val Lys
                        805                 810                 815

Val Thr Ser Lys Asn Tyr Ala Val Tyr Gln Asn Phe Asn Trp Lys Lys
                    820                 825                 830

Lys Asn Ile Arg Ala Val Asn Lys Thr Tyr Leu Ala Lys Tyr Ile Tyr
                    835                 840                 845

Tyr His Ile Asn Gly Leu Ser Tyr Leu Ser Leu Tyr Asp Asn Lys Gly
                    850                 855                 860

Lys Trp Ile Gly Tyr Ile Asn Ala Lys Ala Val Lys Ser Lys Leu Ile
        865                 870                 875                 880

Leu Ser Val Leu Leu Val Ala Gly Ser Ile Ser Tyr Phe Pro Lys Ser
                        885                 890                 895
```

```
Ala Lys Ala Tyr Thr Ser Gly Thr Ser Leu Asp Asn Arg Val Ile Phe
            900                 905                 910
Gln Ser Phe Ser Leu Tyr Met Pro Tyr Glu Ser Asn Met Tyr Lys Ile
            915                 920                 925
Leu Ser Ala Lys Gly Ser Glu Leu Lys Asp Trp Gly Ile Thr Asp Ile
            930                 935                 940
Trp Leu Pro Pro Ala Tyr Arg Ser Phe Asn Met Ala Arg Tyr Met Glu
945                 950                 955                 960
Gly Tyr Ala Ile Ala Asp Arg Tyr Asp Leu Gly Glu Phe Asn Gln Gly
                965                 970                 975
Pro Asn Asn Thr Arg Pro Thr Lys Tyr Gly Thr Ser Asp Glu Leu Lys
            980                 985                 990
Ser Met Val Ser Ala Leu His Ala Ser Gly Leu Lys Val Gln Glu Asp
            995                 1000                1005
Leu Val Pro Asn Gln Val Leu Gly Leu Gly Lys Arg Glu Ala Val
            1010            1015            1020
Tyr Val Thr Arg Val Asp Gln Asn Gly Asn Leu Phe Lys Asn Pro
            1025            1030            1035
Tyr Thr Thr Gly Leu Thr Thr Gln Ile Arg Ala Asp Leu Tyr Leu
            1040            1045            1050
Ala Tyr Thr Lys Gly Gly Gly Glu Gly Gln Ala Lys Tyr Gly Tyr
            1055            1060            1065
Ile Lys Glu Trp Asn Lys Lys Tyr Phe Asn Gly Thr Ser Val Gln
            1070            1075            1080
Gly Gln Gly Met Asp Arg Val Met Lys Asp Ser Glu Gly Ile Pro
            1085            1090            1095
Tyr Arg Tyr Phe Gly Pro Asn Asn Pro Lys Asn His Leu Pro Ser
            1100            1105            1110
Trp Leu Asn Glu Ala Ala Ala Asn Lys Ile Asn Thr Val Asp
            1115            1120            1125
Thr Tyr Leu Ala Val Asp Gly Trp Tyr Ala Ala Lys Asp Ala Ser
            1130            1135            1140
Thr Ser Asp Asn Tyr Trp Lys Pro Met Leu Met Asn Tyr Asp Pro
            1145            1150            1155
Gly Tyr Leu Lys Tyr Met Lys Ser His Gly Tyr Ser Ser Val Asp
            1160            1165            1170
Asp Ile Leu Asn Gly Asp Asn Gly Gln Ile Ala Ser Leu Thr Asp
            1175            1180            1185
Ala Tyr Ile Ala Ser Gln Pro Cys Tyr Gly Phe Gly Ser Glu Glu
            1190            1195            1200
Arg Ser Phe Lys Asn Asp Asn Ser Gly Ser Asp Asp Gln Asp Gln
            1205            1210            1215
Phe Leu Phe Val Lys Lys Asn Gly Thr Thr Leu His Asn Leu Asn
            1220            1225            1230
Asn Thr Ile Ser Gly Gln Lys Gln Phe Leu Leu Gly Met Asp Ile
            1235            1240            1245
Asp Asn Gly Asn Pro Thr Val Gln Lys Glu Gln Ile His Trp Met
            1250            1255            1260
Asn Trp Leu Leu Asp Thr Tyr Gln Phe Asp Gly Phe Arg Ile Asp
            1265            1270            1275
Ala Ala Ser His Tyr Asp Lys Gln Val Leu Leu Asp Glu Ala Asp
            1280            1285            1290
```

```
Val Met Lys Gln His Phe Gly Ser Asn Leu Asn Asp His Leu Ser
1295                1300                1305

Tyr Ile Glu Thr Tyr Glu Ser Ala Gly Thr Asn Phe Glu Asn Ala
1310                1315                1320

Asn Gly Asn Pro Gln Leu Met Met Asp Tyr Ala Leu Phe Tyr Ser
1325                1330                1335

Leu Gln Asn Ala Leu Gly Lys Asn Ser Pro Ser Asn Asn Leu Ser
1340                1345                1350

Thr Ile Ala Thr Asn Ala Val Val Asn Arg Ala Gly Ala Gly Thr
1355                1360                1365

Ala Asn Ala Thr Pro Asn Trp Ser Phe Val Asn His Asp Gln
1370                1375                1380

Glu Lys Asn Arg Val Asn Arg Ile Met Leu Asp Gln Tyr Gly Ile
1385                1390                1395

Lys Pro Gly Thr His Tyr Gly Thr Ser Thr Pro Lys Ala Phe Gln
1400                1405                1410

Asp Leu Tyr Asp Lys Lys Thr Glu Ala Lys Ala Leu Asp Ile Tyr
1415                1420                1425

Glu Arg Asp Met Glu Ser Thr Val Lys Lys Tyr Ala Pro Ser Asn
1430                1435                1440

Val Pro Ser Gln Tyr Ala Tyr Val Leu Thr Asn Lys Asp Thr Val
1445                1450                1455

Pro Thr Val Phe Tyr Gly Asp Leu Tyr Lys Thr Asn Ala Ser Tyr
1460                1465                1470

Met Ser Glu Arg Thr Pro Tyr Tyr Asp Thr Ile Val Lys Leu Leu
1475                1480                1485

Lys Val Arg Lys Asn Tyr Ala Tyr Gly Asn Gln Gln Val Thr Asn
1490                1495                1500

Tyr Lys Ser Asn Thr Ser Ser Thr Ala Gly Lys Asp Leu Ile Ser
1505                1510                1515

Ser Val Arg Tyr Gly Asn Asp Arg Asn Thr Gly Val Ala Thr Val
1520                1525                1530

Ile Gly Asn Asn Pro Lys Thr Asp Thr Thr Ile Lys Val Asn Met
1535                1540                1545

Gly Ser Arg His Ala Asn Gln Leu Phe Glu Asp Ala Thr Gly Phe
1550                1555                1560

His Asn Glu Lys Leu Val Thr Asp Ser Lys Gly Val Leu Thr Val
1565                1570                1575

His Val Lys Gly Thr Gln Asn Ala Arg Val Lys Gly Tyr Leu Gly
1580                1585                1590

Val Trp Ile Pro Ala Lys Lys Ala Ala Thr Pro Lys Gln Gly Pro
1595                1600                1605

Ala Leu Lys Tyr Gly Lys Tyr Val Thr Ile Thr Asn Lys His Tyr
1610                1615                1620

Ala Val Tyr Gln Asp Phe Asn Trp Lys Lys Lys Asn Val Asn Ala
1625                1630                1635

Val Asn Lys Thr Tyr Leu Ala Lys Val Gln Tyr His His Ser Asn
1640                1645                1650

Gly Ser Thr Tyr Leu Ser Leu Tyr Asp Gly Lys Gly Lys Trp Ala
1655                1660                1665

Gly Tyr Ile Asn Ala Lys Ala Lys Thr Gly Ser Gly Lys Gln
1670                1675                1680

Gly Ala Ala Ile Gln Tyr Gly Lys Ser Val Lys Val Thr Ser Lys
```

-continued

```
            1685                1690                1695

Asn Tyr Ala Val Tyr Gln Asn Phe Asn Trp Lys Lys Lys Asn Ile
        1700                1705                1710

Arg Ala Val Asn Lys Thr Tyr Leu Ala Lys Tyr Ile Tyr Tyr His
        1715                1720                1725

Ile Asn Gly Leu Ser Tyr Leu Ser Leu Tyr Asp Asn Lys Gly Lys
        1730                1735                1740

Trp Ile Gly Tyr Ile Asn Ala Lys Ala Val Lys Ser Lys
        1745                1750                1755

<210> SEQ ID NO 12
<211> LENGTH: 705
<212> TYPE: PRT
<213> ORGANISM: Bacillus coagulans
<220> FEATURE:
<221> NAME/KEY: misc_feature
<223> OTHER INFORMATION: mature amino acid sequence alpha-GT-L with C-
      terminal truncation used for expression based on alpha-GT-E

<400> SEQUENCE: 12

Tyr Thr Ser Gly Thr Ser Leu Asp Asn Arg Val Ile Phe Gln Ser Phe
1               5                   10                  15

Ser Leu Tyr Met Pro Tyr Glu Ser Asn Met Tyr Lys Ile Leu Ser Ala
            20                  25                  30

Lys Gly Ser Glu Leu Lys Asp Trp Gly Ile Thr Asp Ile Trp Leu Pro
        35                  40                  45

Pro Ala Tyr Arg Ser Phe Asn Met Ala Arg Tyr Met Glu Gly Tyr Ala
    50                  55                  60

Ile Ala Asp Arg Tyr Asp Leu Gly Glu Phe Asn Gln Gly Pro Asn Asn
65                  70                  75                  80

Thr Arg Pro Thr Lys Tyr Gly Thr Ser Asp Glu Leu Lys Ser Met Val
                85                  90                  95

Ser Ala Leu His Ala Ser Gly Leu Lys Val Gln Glu Asp Leu Val Pro
            100                 105                 110

Asn Gln Val Leu Gly Leu Gly Lys Arg Glu Ala Val Tyr Val Thr Arg
        115                 120                 125

Val Asp Gln Asn Gly Asn Leu Phe Lys Asn Pro Tyr Thr Thr Gly Leu
    130                 135                 140

Thr Thr Gln Ile Arg Ala Asp Leu Tyr Leu Ala Tyr Thr Lys Gly Gly
145                 150                 155                 160

Gly Glu Gly Gln Ala Lys Tyr Gly Tyr Ile Lys Glu Trp Asn Lys Lys
                165                 170                 175

Tyr Phe Asn Gly Thr Ser Val Gln Gly Gln Gly Met Asp Arg Val Met
            180                 185                 190

Lys Asp Ser Glu Gly Ile Pro Tyr Arg Tyr Phe Gly Pro Asn Asn Pro
        195                 200                 205

Lys Asn His Leu Pro Ser Trp Leu Asn Glu Ala Ala Ala Ala Asn Lys
    210                 215                 220

Ile Asn Thr Val Asp Thr Tyr Leu Ala Val Asp Gly Trp Tyr Ala Ala
225                 230                 235                 240

Lys Asp Ala Ser Thr Ser Asp Asn Tyr Trp Lys Pro Met Leu Met Asn
                245                 250                 255

Tyr Asp Pro Gly Tyr Leu Lys Tyr Met Lys Ser His Gly Tyr Ser Ser
            260                 265                 270

Val Asp Asp Ile Leu Asn Gly Asp Asn Gly Gln Ile Ala Ser Leu Thr
        275                 280                 285
```

-continued

```
Asp Ala Tyr Ile Ala Ser Gln Pro Cys Tyr Gly Phe Gly Ser Glu Glu
        290                 295                 300

Arg Ser Phe Lys Asn Asp Asn Ser Gly Ser Asp Gln Asp Gln Phe
305                 310                 315                 320

Leu Phe Val Lys Lys Asn Gly Thr Thr Leu His Asn Leu Asn Asn Thr
                325                 330                 335

Ile Ser Gly Gln Lys Gln Phe Leu Leu Gly Met Asp Ile Asp Asn Gly
                340                 345                 350

Asn Pro Thr Val Gln Lys Glu Gln Ile His Trp Met Asn Trp Leu Leu
            355                 360                 365

Asp Thr Tyr Gln Phe Asp Gly Phe Arg Ile Asp Ala Ala Ser His Tyr
        370                 375                 380

Asp Lys Gln Val Leu Leu Asp Glu Ala Asp Val Met Lys Gln His Phe
385                 390                 395                 400

Gly Ser Asn Leu Asn Asp His Leu Ser Tyr Ile Glu Thr Tyr Glu Ser
                405                 410                 415

Ala Gly Thr Asn Phe Glu Asn Ala Asn Gly Asn Pro Gln Leu Met Met
                420                 425                 430

Asp Tyr Ala Leu Phe Tyr Ser Leu Gln Asn Ala Leu Gly Lys Asn Ser
            435                 440                 445

Pro Ser Asn Asn Leu Ser Thr Ile Ala Thr Asn Ala Val Val Asn Arg
450                 455                 460

Ala Gly Ala Gly Thr Ala Asn Ala Thr Pro Asn Trp Ser Phe Val Asn
465                 470                 475                 480

Asn His Asp Gln Glu Lys Asn Arg Val Asn Arg Ile Met Leu Asp Gln
                485                 490                 495

Tyr Gly Ile Lys Pro Gly Thr His Tyr Gly Thr Ser Thr Pro Lys Ala
            500                 505                 510

Phe Gln Asp Leu Tyr Asp Lys Lys Thr Glu Ala Lys Ala Leu Asp Ile
        515                 520                 525

Tyr Glu Arg Asp Met Glu Ser Thr Val Lys Lys Tyr Ala Pro Ser Asn
        530                 535                 540

Val Pro Ser Gln Tyr Ala Tyr Val Leu Thr Asn Lys Asp Thr Val Pro
545                 550                 555                 560

Thr Val Phe Tyr Gly Asp Leu Tyr Lys Thr Asn Ala Ser Tyr Met Ser
                565                 570                 575

Glu Arg Thr Pro Tyr Tyr Asp Thr Ile Val Lys Leu Leu Lys Val Arg
            580                 585                 590

Lys Asn Tyr Ala Tyr Gly Asn Gln Gln Val Thr Asn Tyr Lys Ser Asn
            595                 600                 605

Thr Ser Ser Thr Ala Gly Lys Asp Leu Ile Ser Ser Val Arg Tyr Gly
        610                 615                 620

Asn Asp Arg Asn Thr Gly Val Ala Thr Val Ile Gly Asn Asn Pro Lys
625                 630                 635                 640

Thr Asp Thr Thr Ile Lys Val Asn Met Gly Ser Arg His Ala Asn Gln
                645                 650                 655

Leu Phe Glu Asp Ala Thr Gly Phe His Asn Glu Lys Leu Val Thr Asp
                660                 665                 670

Ser Lys Gly Val Leu Thr Val His Val Lys Gly Thr Gln Asn Ala Arg
        675                 680                 685

Val Lys Gly Tyr Leu Gly Val Trp Ile Pro Ala Lys Lys Ala Ala Thr
    690                 695                 700
```

Pro
705

<210> SEQ ID NO 13
<211> LENGTH: 2115
<212> TYPE: DNA
<213> ORGANISM: Artificial Sequence
<220> FEATURE:
<223> OTHER INFORMATION: synthetic nucleotide sequence of the mature and
      3' deleted gene encoding alpha-GT-L

<400> SEQUENCE: 13

```
tatacatcag gcacatcact ggataatcgc gtcattttc agagcttttc actgtacatg      60
ccgtatgaaa gcaacatgta taaaatcctg tcagcgaaag gcagcgaact gaaagattgg    120
ggcattacag atatttggct gcctccggca tatcgcagct taatatggc aagatatatg     180
gaaggctatg caattgcaga tagatatgat ctgggcgaat taatcaggg accgaataat     240
acacgtccga caaaatatgg cacaagcgac gaactgaaat caatggtttc agcactgcat    300
gcatcaggcc tgaaagttca agaagatctg gttccgaatc aagttctggg cctgggcaaa    360
cgcgaagcag tttatgttac aagagttgat cagaacggca acctgtttaa aaacccgtat    420
acaacaggcc tgacaacaca aattagagca gatctgtatc tggcgtatac aaaaggcgga    480
ggcgaaggcc aagcaaaata tggctatatc aaagaatgga caaaaaata ctttaacggc     540
acaagcgttc aaggccaagg catggataga gttatgaaag attcagaagg catcccgtat    600
agatattttg gaccgaataa cccgaaaaat catctgccgt catggctgaa tgaagcagca    660
gcagcgaata aaatcaatac ggttgataca tatctggcag tcgatggctg gtatgcagca    720
aaagatgcat caacatcaga caactattgg aaaccgatgc tgatgaatta tgatccggga    780
tacctgaaat atatgaaaag ccatggctat agcagcgtcg atgatattct gaatggcgat    840
aatggccaaa ttgcatcact gacagatgca tatattgcat cacaaccgtg ctatggcttt    900
ggctcagaag aacgcagctt taaaaacgat aatagcggca cgacgatca agatcaattt    960
ctgtttgtca aaaaaaacgg cacgacactg cataacctga caatacaat ttcaggccag   1020
aaacaatttc tgctgggcat ggatattgat aatggcaatc cgacagtcca gaagaacaa   1080
attcattgga tgaattggct gctggacacg tatcaattg atggctttag aattgatgca   1140
gcgagccatt atgataaaca agtcctgctg gatgaagcgg atgttatgaa caacattttt   1200
ggcagcaatc tgaacgacca tctgagctat attgaaacgt atgaatcagc aggcacaaac   1260
tttgaaaatg cgaatggaaa tccgcagctg atgatggatt atgcactgtt ttatagcctg   1320
caaaatgcgc tgggcaaaaa ttcaccgtca ataatctga gcacaattgc aacaaatgca   1380
gttgttaata gagcaggcgc aggcacagca atgcaacac gaattggtc atttgtcaac    1440
aaccatgatc aagaaaaaaa tcgcgtcaac cgcattatgc tggatcagta tggcattaaa   1500
ccgggaacac attatggcac atcaacaccg aaagcatttc aagacctgta cgacaaaaaa   1560
acagaagcaa aagcgctgga tatctatgaa agagatatgg aaagcacagt caaaaaatac   1620
gcaccgtcaa atgttccgag ccaatatgcg tatgtcctga caaataaaga tacagtcccg   1680
acagtttttt atggcgacct gtataaaaca acgcgagct atatgtcaga acgcacaccg   1740
tattatgata cgattgtcaa actgctgaaa gtccgcaaaa actatgcgta tggcaatcaa   1800
caggtcacaa actacaaaag caatacatca tcaacggcag gcaaagatct gatttcatca   1860
gttagatatg gcaacgatag aaatacaggc gttgcaacag ttattggcaa taatccgaaa   1920
acggatacga cgatcaaagt taatatgggc tcaagacatg cgaaccagct gtttgaagat   1980
```

```
gcaacaggct tcataatga aaaactggtc acagattcaa aaggcgttct gacagttcat    2040
gttaaaggca cacaaaatgc acgcgttaaa ggctatctgg gcgtttggat tccggcaaaa    2100
aaagcagcaa caccg                                                     2115
```

```
<210> SEQ ID NO 14
<211> LENGTH: 12
<212> TYPE: PRT
<213> ORGANISM: Lactobacillus reuteri
<220> FEATURE:
<221> NAME/KEY: misc_feature
<223> OTHER INFORMATION: Conserved catalytic domain I of GH70, GTFA
      enzyme

<400> SEQUENCE: 14

Gly Leu Gln Val Met Ala Asp Trp Val Pro Asp Gln
1               5                   10

<210> SEQ ID NO 15
<211> LENGTH: 19
<212> TYPE: PRT
<213> ORGANISM: Lactobacillus reuteri
<220> FEATURE:
<221> NAME/KEY: misc_feature
<223> OTHER INFORMATION: Conserved catalytic domain II of GH70, GTFA
      enzyme

<400> SEQUENCE: 15

Phe Asp Ser Val Arg Val Asp Ala Pro Asp Asn Ile Asp Ala Asp Leu
1               5                   10                  15

Met Asn Ile

<210> SEQ ID NO 16
<211> LENGTH: 13
<212> TYPE: PRT
<213> ORGANISM: Lactobacillus reuteri
<220> FEATURE:
<221> NAME/KEY: misc_feature
<223> OTHER INFORMATION: Conserved catalytic domain III of GH70, GTFA
      enzyme

<400> SEQUENCE: 16

His Ile Asn Ile Leu Glu Asp Trp Asn His Ala Asp Pro
1               5                   10

<210> SEQ ID NO 17
<211> LENGTH: 12
<212> TYPE: PRT
<213> ORGANISM: Lactobacillus reuteri
<220> FEATURE:
<221> NAME/KEY: misc_feature
<223> OTHER INFORMATION: Conserved catalytic domain IV of GH70, GTFA
      enzyme
<220> FEATURE:
<221> NAME/KEY: misc_feature
<222> LOCATION: (9)..(11)
<223> OTHER INFORMATION: Xaa= any amino acid residue or none

<400> SEQUENCE: 17

Tyr Ser Phe Val Arg Ala His Asp Asn Asn Ser Gln
1               5                   10

<210> SEQ ID NO 18
<211> LENGTH: 12
<212> TYPE: PRT
<213> ORGANISM: Lactobacillus reuteri
<220> FEATURE:
```

```
<221> NAME/KEY: misc_feature
<223> OTHER INFORMATION: Conserved catalytic domain I of GH70, GTFO
      enzyme

<400> SEQUENCE: 18

Gly Leu Gln Val Met Ala Asp Trp Val Pro Asp Gln
1               5                   10

<210> SEQ ID NO 19
<211> LENGTH: 19
<212> TYPE: PRT
<213> ORGANISM: Lactobacillus reuteri
<220> FEATURE:
<221> NAME/KEY: misc_feature
<223> OTHER INFORMATION: Conserved catalytic domain II of GH70, GTFO
      enzyme

<400> SEQUENCE: 19

Phe Asp Ser Val Arg Val Asp Ala Pro Asp Asn Ile Asp Ala Asp Leu
1               5                   10                  15

Met Asn Ile

<210> SEQ ID NO 20
<211> LENGTH: 13
<212> TYPE: PRT
<213> ORGANISM: Lactobacillus reuteri
<220> FEATURE:
<221> NAME/KEY: misc_feature
<223> OTHER INFORMATION: Conserved catalytic domain III of GH70, GTFO
      enzyme

<400> SEQUENCE: 20

His Ile Asn Ile Leu Glu Asp Trp Asn Ser Ser Asp Pro
1               5                   10

<210> SEQ ID NO 21
<211> LENGTH: 12
<212> TYPE: PRT
<213> ORGANISM: Lactobacillus reuteri
<220> FEATURE:
<221> NAME/KEY: misc_feature
<223> OTHER INFORMATION: Conserved catalytic domain IV of GH70, GTFO
      enzyme

<400> SEQUENCE: 21

Tyr Ser Phe Ile Arg Ala His Asp Asn Asn Ser Gln
1               5                   10

<210> SEQ ID NO 22
<211> LENGTH: 12
<212> TYPE: PRT
<213> ORGANISM: Lactobacillus reuteri
<220> FEATURE:
<221> NAME/KEY: MISC_FEATURE
<223> OTHER INFORMATION: Conserved catalytic domain I of GH70, GTF180
      enzyme

<400> SEQUENCE: 22

Gly Leu Gln Ala Ile Ala Asp Trp Val Pro Asp Gln
1               5                   10

<210> SEQ ID NO 23
<211> LENGTH: 19
<212> TYPE: PRT
<213> ORGANISM: Lactobacillus reuteri
<220> FEATURE:
<221> NAME/KEY: MISC_FEATURE
<223> OTHER INFORMATION: Conserved catalytic domain II of GH70, GTF180
```

```
            enzyme

<400> SEQUENCE: 23

Phe Asp Gly Ile Arg Val Asp Ala Val Asp Asn Val Asp Val Asp Leu
1               5                   10                  15

Leu Ser Ile

<210> SEQ ID NO 24
<211> LENGTH: 13
<212> TYPE: PRT
<213> ORGANISM: Lactobacillus reuteri
<220> FEATURE:
<221> NAME/KEY: MISC_FEATURE
<223> OTHER INFORMATION: Conserved catalytic domain III of GH70, GTF180
      enzyme

<400> SEQUENCE: 24

His Ile Asn Ile Leu Glu Asp Trp Gly Trp Asp Asp Pro
1               5                   10

<210> SEQ ID NO 25
<211> LENGTH: 12
<212> TYPE: PRT
<213> ORGANISM: Lactobacillus reuteri
<220> FEATURE:
<221> NAME/KEY: MISC_FEATURE
<223> OTHER INFORMATION: Conserved catalytic domain IV of GH70, GTF180
      enzyme

<400> SEQUENCE: 25

Tyr Asn Phe Val Arg Ala His Asp Ser Asn Ala Gln
1               5                   10

<210> SEQ ID NO 26
<211> LENGTH: 12
<212> TYPE: PRT
<213> ORGANISM: Lactobacillus reuteri
<220> FEATURE:
<221> NAME/KEY: MISC_FEATURE
<223> OTHER INFORMATION: Conserved catalytic domain I of GH70, GTFML1
      enzyme

<400> SEQUENCE: 26

Gly Ile Gln Ala Met Ala Asp Trp Val Pro Asp Gln
1               5                   10

<210> SEQ ID NO 27
<211> LENGTH: 19
<212> TYPE: PRT
<213> ORGANISM: Lactobacillus reuteri
<220> FEATURE:
<221> NAME/KEY: MISC_FEATURE
<223> OTHER INFORMATION: Conserved catalytic domain II of GH70, GTFML1
      enzyme

<400> SEQUENCE: 27

Phe Asp Ser Ile Arg Val Asp Ala Val Asp Asn Val Asp Ala Asp Leu
1               5                   10                  15

Leu Asp Ile

<210> SEQ ID NO 28
<211> LENGTH: 13
<212> TYPE: PRT
<213> ORGANISM: Lactobacillus reuteri
<220> FEATURE:
<221> NAME/KEY: MISC_FEATURE
<223> OTHER INFORMATION: Conserved catalytic domain III of GH70, GTFML1
```

-continued enzyme

<400> SEQUENCE: 28

His Ile Asn Ile Leu Glu Asp Trp Gly Gly Gln Asp Pro
1               5                   10

<210> SEQ ID NO 29
<211> LENGTH: 12
<212> TYPE: PRT
<213> ORGANISM: Lactobacillus reuteri
<220> FEATURE:
<221> NAME/KEY: MISC_FEATURE
<223> OTHER INFORMATION: Conserved catalytic domain IV of GH70, GTFML1
      enzyme

<400> SEQUENCE: 29

Tyr Ser Phe Ile Arg Ala His Asp Asn Gly Ser Gln
1               5                   10

<210> SEQ ID NO 30
<211> LENGTH: 12
<212> TYPE: PRT
<213> ORGANISM: Leuconostoc citreum
<220> FEATURE:
<221> NAME/KEY: MISC_FEATURE
<223> OTHER INFORMATION: Conserved catalytic domain I of GH70, DSRE CD2
      enzyme

<400> SEQUENCE: 30

Asn Met Gln Val Met Ala Asp Val Val Asp Asn Gln
1               5                   10

<210> SEQ ID NO 31
<211> LENGTH: 19
<212> TYPE: PRT
<213> ORGANISM: Leuconostoc citreum
<220> FEATURE:
<221> NAME/KEY: misc_feature
<223> OTHER INFORMATION: Conserved catalytic domain II of GH70, DSRE CD2
      enzyme

<400> SEQUENCE: 31

Phe Asp Ser Ile Arg Ile Asp Ala Val Asp Phe Ile His Asn Asp Thr
1               5                   10                  15

Ile Gln Arg

<210> SEQ ID NO 32
<211> LENGTH: 13
<212> TYPE: PRT
<213> ORGANISM: Leuconostoc citreum
<220> FEATURE:
<221> NAME/KEY: misc_feature
<223> OTHER INFORMATION: Conserved catalytic domain III of GH70, DSRE
      CD2 enzyme

<400> SEQUENCE: 32

His Ile Ser Leu Val Glu Ala Gly Leu Asp Ala Gly Thr
1               5                   10

<210> SEQ ID NO 33
<211> LENGTH: 12
<212> TYPE: PRT
<213> ORGANISM: Leuconostoc citreum
<220> FEATURE:
<221> NAME/KEY: misc_feature
<223> OTHER INFORMATION: Conserved catalytic domain IV of GH70, DSRE CD2
      enzyme

```
<400> SEQUENCE: 33

Tyr Ser Ile Ile His Ala His Asp Lys Gly Val Gln
1               5                   10

<210> SEQ ID NO 34
<211> LENGTH: 12
<212> TYPE: PRT
<213> ORGANISM: Leuconostoc citreum
<220> FEATURE:
<221> NAME/KEY: misc_feature
<223> OTHER INFORMATION: Conserved catalytic domain I of GH70, BRSA
      enzyme

<400> SEQUENCE: 34

Gly Met Gln Val Met Ala Asp Val Val Ala Asn Gln
1               5                   10

<210> SEQ ID NO 35
<211> LENGTH: 19
<212> TYPE: PRT
<213> ORGANISM: Leuconostoc citreum
<220> FEATURE:
<221> NAME/KEY: misc_feature
<223> OTHER INFORMATION: Conserved catalytic domain II of GH70, BRSA
      enzyme

<400> SEQUENCE: 35

Phe Asp Ser Ile Arg Ile Asp Ala Val Asp Phe Val Ser Asn Asp Leu
1               5                   10                  15

Ile Gln Arg

<210> SEQ ID NO 36
<211> LENGTH: 13
<212> TYPE: PRT
<213> ORGANISM: Leuconostoc citreum
<220> FEATURE:
<221> NAME/KEY: misc_feature
<223> OTHER INFORMATION: Conserved catalytic domain III of GH70, BRSA
      enzyme

<400> SEQUENCE: 36

His Leu Ser Leu Val Glu Ala Gly Leu Asp Ala Gly Thr
1               5                   10

<210> SEQ ID NO 37
<211> LENGTH: 12
<212> TYPE: PRT
<213> ORGANISM: Leuconostoc citreum
<220> FEATURE:
<221> NAME/KEY: misc_feature
<223> OTHER INFORMATION: Conserved catalytic domain IV of GH70, BRSA
      enzyme

<400> SEQUENCE: 37

Tyr Ser Ile Ile His Ala His Asp Lys Asp Ile Gln
1               5                   10

<210> SEQ ID NO 38
<211> LENGTH: 12
<212> TYPE: PRT
<213> ORGANISM: Lactobacillus reuteri
<220> FEATURE:
<221> NAME/KEY: misc_feature
<223> OTHER INFORMATION: Conserved catalytic domain I of GH70, 4,6
      alpha-GTB enzyme

<400> SEQUENCE: 38
```

```
Gly Leu Lys Val Gln Glu Asp Ile Val Met Asn Gln
1               5                   10
```

<210> SEQ ID NO 39
<211> LENGTH: 19
<212> TYPE: PRT
<213> ORGANISM: Lactobacillus reuteri
<220> FEATURE:
<221> NAME/KEY: misc_feature
<223> OTHER INFORMATION: Conserved catalytic domain II of GH70, 4,6
      alpha-GTB enzyme

<400> SEQUENCE: 39

```
Phe Asp Gly Phe Arg Val Asp Ala Ala Asp Asn Ile Asp Ala Asp Val
1               5                   10                  15

Leu Asp Gln
```

<210> SEQ ID NO 40
<211> LENGTH: 13
<212> TYPE: PRT
<213> ORGANISM: Lactobacillus reuteri
<220> FEATURE:
<221> NAME/KEY: misc_feature
<223> OTHER INFORMATION: Conserved catalytic domain III of GH70, 4,6
      alpha-GTB enzyme

<400> SEQUENCE: 40

```
His Leu Ser Tyr Asn Glu Gly Tyr His Ser Gly Ala Ala
1               5                   10
```

<210> SEQ ID NO 41
<211> LENGTH: 15
<212> TYPE: PRT
<213> ORGANISM: Lactobacillus reuteri
<220> FEATURE:
<221> NAME/KEY: misc_feature
<223> OTHER INFORMATION: Conserved catalytic domain IV of GH70, 4,6
      alpha-GTB enzyme

<400> SEQUENCE: 41

```
Trp Ser Phe Val Thr Asn His Asp Gln Arg Lys Asn Leu Ile Asn
1               5                   10                  15
```

<210> SEQ ID NO 42
<211> LENGTH: 12
<212> TYPE: PRT
<213> ORGANISM: Lactobacillus reuteri
<220> FEATURE:
<221> NAME/KEY: misc_feature
<223> OTHER INFORMATION: Conserved catalytic domain I of GH70, 4,6
      alpha-GTML4 enzyme

<400> SEQUENCE: 42

```
Gly Leu Lys Val Gln Glu Asp Ile Val Met Asn Gln
1               5                   10
```

<210> SEQ ID NO 43
<211> LENGTH: 19
<212> TYPE: PRT
<213> ORGANISM: Lactobacillus reuteri
<220> FEATURE:
<221> NAME/KEY: misc_feature
<223> OTHER INFORMATION: Conserved catalytic domain II of GH70, 4,6
      alpha-GTML4 enzyme

<400> SEQUENCE: 43

```
Phe Asp Gly Phe Arg Val Asp Ala Ala Asp Asn Ile Asp Ala Asp Val
1               5                   10                  15
```

Leu Asp Gln

<210> SEQ ID NO 44
<211> LENGTH: 13
<212> TYPE: PRT
<213> ORGANISM: Lactobacillus reuteri
<220> FEATURE:
<221> NAME/KEY: misc_feature
<223> OTHER INFORMATION: Conserved catalytic domain III of GH70, 4,6
      alpha-GTML4 enzyme

<400> SEQUENCE: 44

His Leu Ser Tyr Asn Glu Gly Tyr His Ser Gly Ala Ala
1               5                   10

<210> SEQ ID NO 45
<211> LENGTH: 15
<212> TYPE: PRT
<213> ORGANISM: Lactobacillus reuteri
<220> FEATURE:
<221> NAME/KEY: misc_feature
<223> OTHER INFORMATION: Conserved catalytic domain IV of GH70, 4,6
      alpha-GTML4 enzyme

<400> SEQUENCE: 45

Trp Ser Phe Val Thr Asn His Asp Gln Arg Lys Asn Leu Ile Asn
1               5                   10                  15

<210> SEQ ID NO 46
<211> LENGTH: 12
<212> TYPE: PRT
<213> ORGANISM: Lactobacillus reuteri
<220> FEATURE:
<221> NAME/KEY: misc_feature
<223> OTHER INFORMATION: Conserved catalytic domain I of GH70, 4,6
      alpha-GTW enzyme

<400> SEQUENCE: 46

Gly Leu Lys Val Gln Glu Asp Leu Val Met Asn Gln
1               5                   10

<210> SEQ ID NO 47
<211> LENGTH: 19
<212> TYPE: PRT
<213> ORGANISM: Lactobacillus reuteri
<220> FEATURE:
<221> NAME/KEY: misc_feature
<223> OTHER INFORMATION: Conserved catalytic domain II of GH70, 4,6
      alpha-GTW enzyme

<400> SEQUENCE: 47

Phe Asp Gly Phe Arg Val Asp Ala Ala Asp Asn Ile Asp Ala Asp Val
1               5                   10                  15

Leu Asp Gln

<210> SEQ ID NO 48
<211> LENGTH: 13
<212> TYPE: PRT
<213> ORGANISM: Lactobacillus reuteri
<220> FEATURE:
<221> NAME/KEY: misc_feature
<223> OTHER INFORMATION: Conserved catalytic domain III of GH70, 4,6
      alpha-GTW enzyme

<400> SEQUENCE: 48

His Leu Val Tyr Asn Glu Gly Tyr His Ser Gly Ala Ala
1               5                   10

<210> SEQ ID NO 49
<211> LENGTH: 15
<212> TYPE: PRT
<213> ORGANISM: Lactobacillus reuteri
<220> FEATURE:
<221> NAME/KEY: misc_feature
<223> OTHER INFORMATION: Conserved catalytic domain IV of GH70, 4,6 alpha-GTW enzyme

<400> SEQUENCE: 49

Trp Ser Phe Val Thr Asn His Asp Gln Arg Lys Asn Val Ile Asn
1               5                   10                  15

<210> SEQ ID NO 50
<211> LENGTH: 12
<212> TYPE: PRT
<213> ORGANISM: Exiguobacterium acetylicum
<220> FEATURE:
<221> NAME/KEY: misc_feature
<223> OTHER INFORMATION: Conserved catalytic domain I of GH70, alpha-GT-E enzyme

<400> SEQUENCE: 50

Asn Ile Lys Val Gln Met Asp Leu Val Pro Asn Gln
1               5                   10

<210> SEQ ID NO 51
<211> LENGTH: 19
<212> TYPE: PRT
<213> ORGANISM: Exiguobacterium acetylicum
<220> FEATURE:
<221> NAME/KEY: misc_feature
<223> OTHER INFORMATION: Conserved catalytic domain II of GH70, alpha-GT-E enzyme

<400> SEQUENCE: 51

Phe Asp Gly Phe Arg Ile Asp Ala Ala Ser His Tyr Asp Thr Ala Ile
1               5                   10                  15

Leu Lys Ala

<210> SEQ ID NO 52
<211> LENGTH: 13
<212> TYPE: PRT
<213> ORGANISM: Exiguobacterium acetylicum
<220> FEATURE:
<221> NAME/KEY: misc_feature
<223> OTHER INFORMATION: Conserved catalytic domain III of GH70, alpha-GT-E enzyme

<400> SEQUENCE: 52

Tyr Leu Ser Tyr Ile Glu Ser Tyr Lys Thr Glu Gln Asn
1               5                   10

<210> SEQ ID NO 53
<211> LENGTH: 15
<212> TYPE: PRT
<213> ORGANISM: Exiguobacterium acetylicum
<220> FEATURE:
<221> NAME/KEY: misc_feature
<223> OTHER INFORMATION: Conserved catalytic domain IV of GH70, alpha-GT-E enzyme

<400> SEQUENCE: 53

Trp Ser Phe Val Asn Asn His Asp Gln Glu Lys Asn Arg Val Asn
1               5                   10                  15

```
<210> SEQ ID NO 54
<211> LENGTH: 12
<212> TYPE: PRT
<213> ORGANISM: Bacillus coagulans
<220> FEATURE:
<221> NAME/KEY: misc_feature
<223> OTHER INFORMATION: Conserved catalytic domain I of GH70, alpha-
      GT-S enzyme

<400> SEQUENCE: 54

Gly Leu Lys Val Gln Glu Asp Leu Val Pro Asn Gln
1               5                   10

<210> SEQ ID NO 55
<211> LENGTH: 19
<212> TYPE: PRT
<213> ORGANISM: Bacillus coagulans
<220> FEATURE:
<221> NAME/KEY: misc_feature
<223> OTHER INFORMATION: Conserved catalytic domain II of GH70, alpha-
      GT-S enzyme

<400> SEQUENCE: 55

Phe Asp Gly Phe Arg Ile Asp Ala Ala Gly His Tyr Asp Lys Gln Val
1               5                   10                  15

Leu Leu Asp

<210> SEQ ID NO 56
<211> LENGTH: 13
<212> TYPE: PRT
<213> ORGANISM: Bacillus coagulans
<220> FEATURE:
<221> NAME/KEY: misc_feature
<223> OTHER INFORMATION: Conserved catalytic domain III of GH70, alpha-
      GT-S enzyme

<400> SEQUENCE: 56

His Leu Ser Tyr Ile Glu Ser Tyr Gln Ser Ala Gly Thr
1               5                   10

<210> SEQ ID NO 57
<211> LENGTH: 15
<212> TYPE: PRT
<213> ORGANISM: Bacillus coagulans
<220> FEATURE:
<221> NAME/KEY: misc_feature
<223> OTHER INFORMATION: Conserved catalytic domain IV of GH70, alpha-
      GT-S enzyme

<400> SEQUENCE: 57

Trp Ser Phe Val Asn Asn His Asp Gln Glu Lys Asn Arg Val Asn
1               5                   10                  15

<210> SEQ ID NO 58
<211> LENGTH: 12
<212> TYPE: PRT
<213> ORGANISM: Bacillus coagulans
<220> FEATURE:
<221> NAME/KEY: misc_feature
<223> OTHER INFORMATION: Conserved catalytic domain I of GH70, alpha-
      GT-L enzyme

<400> SEQUENCE: 58

Gly Leu Lys Val Gln Glu Asp Leu Val Pro Asn Gln
1               5                   10

<210> SEQ ID NO 59
<211> LENGTH: 19
```

```
<212> TYPE: PRT
<213> ORGANISM: Bacillus coagulans
<220> FEATURE:
<221> NAME/KEY: misc_feature
<223> OTHER INFORMATION: Conserved catalytic domain II of GH70, alpha-
      GT-L enzyme

<400> SEQUENCE: 59

Phe Asp Gly Phe Arg Ile Asp Ala Ala Ser His Tyr Asp Lys Gln Val
1               5                   10                  15

Leu Leu Asp

<210> SEQ ID NO 60
<211> LENGTH: 13
<212> TYPE: PRT
<213> ORGANISM: Bacillus coagulans
<220> FEATURE:
<221> NAME/KEY: misc_feature
<223> OTHER INFORMATION: Conserved catalytic domain III of GH70, alpha-
      GT-L enzyme

<400> SEQUENCE: 60

His Leu Ser Tyr Ile Glu Thr Tyr Glu Ser Ala Gly Thr
1               5                   10

<210> SEQ ID NO 61
<211> LENGTH: 15
<212> TYPE: PRT
<213> ORGANISM: Bacillus coagulans
<220> FEATURE:
<221> NAME/KEY: misc_feature
<223> OTHER INFORMATION: Conserved catalytic domain IV of GH70, alpha-
      GT-L enzyme

<400> SEQUENCE: 61

Trp Ser Phe Val Asn Asn His Asp Gln Glu Lys Asn Arg Val Asn
1               5                   10                  15

<210> SEQ ID NO 62
<211> LENGTH: 93
<212> TYPE: DNA
<213> ORGANISM: Artificial Sequence
<220> FEATURE:
<223> OTHER INFORMATION: terminator sequence

<400> SEQUENCE: 62
ggttaccttg aatgtatata aacattctca aagggatttc taataaaaaa cgctcggttg    60
ccgccgggcg tttttatgc atcgatggaa ttc                                  93

<210> SEQ ID NO 63
<211> LENGTH: 21
<212> TYPE: DNA
<213> ORGANISM: Artificial Sequence
<220> FEATURE:
<223> OTHER INFORMATION: linker sequence

<400> SEQUENCE: 63
ggatcctgac tgcctgagct t                                              21
```